(12) United States Patent
Baram et al.

(10) Patent No.: US 11,274,288 B2
(45) Date of Patent: Mar. 15, 2022

(54) COMPOSITIONS AND METHODS FOR PROMOTING HOMOLOGY DIRECTED REPAIR MEDIATED GENE EDITING

(71) Applicant: EMENDOBIO INC., Wilmington, DE (US)

(72) Inventors: David Baram, Nir Zvi (IL); Lior Izhar, Tel-Aviv (IL); Noam Diamant, Ein-Vered (IL); Rafi Emmanuel, Ramla (IL)

(73) Assignee: EMENDOBIO INC., Wilmington, DE (US)

( * ) Notice: Subject to any disclaimer, the term of this patent is extended or adjusted under 35 U.S.C. 154(b) by 798 days.

(21) Appl. No.: 16/077,190

(22) PCT Filed: Feb. 15, 2017

(86) PCT No.: PCT/US2017/017932
§ 371 (c)(1),
(2) Date: Aug. 10, 2018

(87) PCT Pub. No.: WO2017/142923
PCT Pub. Date: Aug. 24, 2017

(65) Prior Publication Data
US 2021/0207119 A1    Jul. 8, 2021

Related U.S. Application Data

(60) Provisional application No. 62/410,627, filed on Oct. 20, 2016, provisional application No. 62/397,288, filed on Sep. 20, 2016, provisional application No. 62/295,517, filed on Feb. 16, 2016, provisional application No. 62/295,518, filed on Feb. 16, 2016.

(51) Int. Cl.
*C12N 9/96* (2006.01)
*C12N 9/22* (2006.01)

(52) U.S. Cl.
CPC .............. *C12N 9/96* (2013.01); *C12N 9/22* (2013.01); *C07K 2319/00* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 8,993,233 B2 * | 3/2015 | Zhang | C12N 15/01 435/6.1 |
| 2015/0071898 A1 * | 3/2015 | Liu | C12N 15/907 424/94.3 |
| 2015/0156996 A1 | 6/2015 | Fahrenkrug et al. | |
| 2016/0002615 A1 | 1/2016 | Smith et al. | |

OTHER PUBLICATIONS

Davis et al., "DNA Nicks Promote Efficient and Safe Targeted Gene Correction", PLoS ONE, 2011, vol. 6.
Cheung, "Palindrome Regeneration by Template Strand-Switching Mechanism at the Origin of DNA Replication of Porcine Circovirus via the Rolling-Circle Melting-Pot Replication Model", J Virol, 2004, vol. 78.
Zyrina et al., "N.BspD6I DNA nickase strongly stimulates template-independent synthesis of non-palindromic repetitive DNA by Bst DNA polymerase", Biol Chem. 2007, vol. 388.
Wang et al., "Targeted gene addition to a predetermined site in the human genome using a ZFN-based nicking enzyme", Genome Res., 2012, vol. 22.
Gutschner et al., "Post-translational Regulation of Cas9 during G1 Enhances Homology-Directed Repair," Cell Rep., Feb. 2016., vol. 14.
Written Opinion, dated Jun. 12, 2017 in connection with PCT International Application No. PCT/US2017/017932.
International Search Report dated Jun. 12, 2017 in connection with PCT International Application No. PCT/US2017/017932.

* cited by examiner

*Primary Examiner* — Anand U Desai
(74) *Attorney, Agent, or Firm* — Gary J. Gershik

(57) ABSTRACT

The present invention relates to compositions and methods for increasing the rate of nuclease-mediated site specific insertions of donor DNA sequence to the genome via recombination. More specifically, the method utilizes a non-naturally occurring nuclease-homology directed repair (HDR) protein chimeras for genome editing applications. Physically tethering the activity of a DNA nuclease to an HDR protein results in significant increase in the fraction of nuclease induced DNA breaks that are repaired by homologous recombination and provides higher accuracy and specificity of genome editing.

20 Claims, 4 Drawing Sheets

Specification includes a Sequence Listing.

Fig. 3
A.
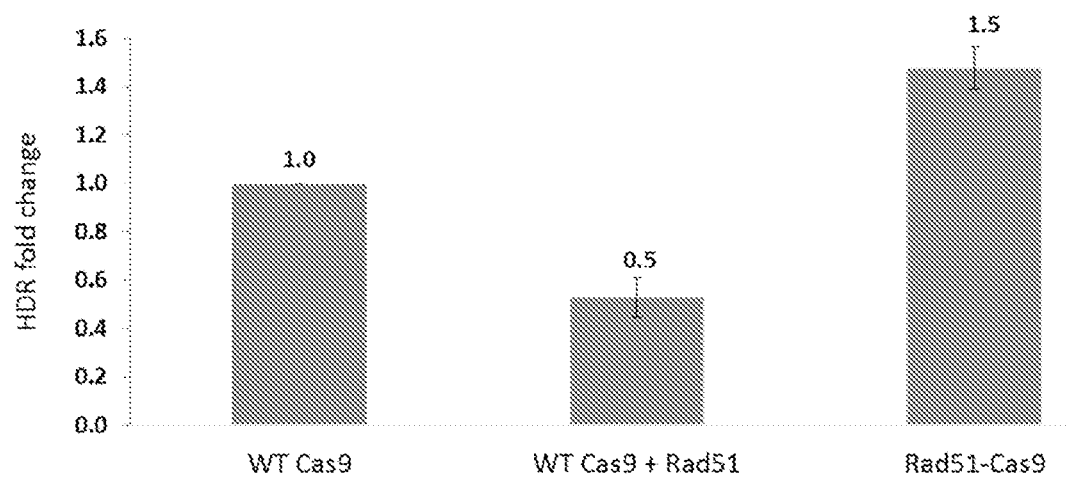
B.
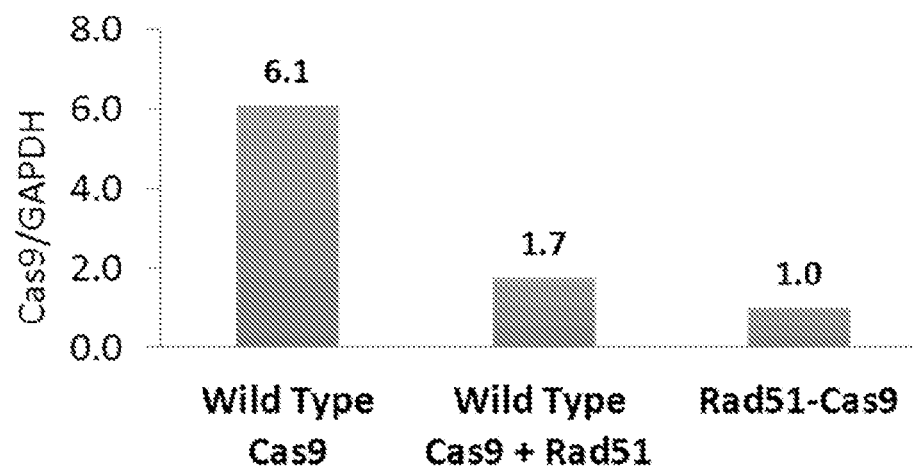

SEQUENCE LISTING

```
<160> NUMBER OF SEQ ID NOS: 16

<210> SEQ ID NO 1
<211> LENGTH: 7763
<212> TYPE: DNA
<213> ORGANISM: Artificial Sequence
<220> FEATURE:
<223> OTHER INFORMATION: synthesized, pLETI16V5-IGFP2

<400> SEQUENCE: 1
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg ggtctctctg     240
gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac ccttttagtc agtgtggaaa atctctagca gtggcgcccg     420
aacagggact tgaaagcgaa agggaaacca gaggagctct ctcgacgcag gactcggctt     480
gctgaagcgc gcacggcaag aggcgagggg cggcgactgg tgagtacgcc aaaaattttg     540 actgcggag gctagaagga gagagatggg tgcgagagcg tcagtattaa gcgggggaga     600
attagatcgc gatgggaaaa aattcggtta aggccagggg gaaagaaaaa atataaatta     660
aaacatatag tatgggcaag cagggagcta gaacgattcg cagttaatcc tggcctgtta     720
```

```
gaaacatcag aaggctgtag acaaatactg ggacagctac aaccatccct tcagacagga      780
tcagaagaac ttagatcatt atataataca gtagcaaccc tctattgtgt gcatcaaagg      840
atagagataa aagacaccaa ggaagcttta gacaagatag aggaagagca aaacaaaagt      900
aagaccaccg cacagcaagc ggccgctgat cttcagacct ggaggaggag atatgaggga      960
caattggaga agtgaattat ataaatataa agtagtaaaa attgaaccat taggagtagc     1020
acccaccaag gcaaagagaa gagtggtgca gagagaaaaa agagcagtgg gaataggagc     1080
tttgttcctt gggttcttgg agcagcagg aagcactatg ggcgcagcgt caatgacgct      1140
gacggtacag gccagacaat tattgtctgg tatagtgcag cagcagaaca atttgctgag     1200
ggctattgag gcgcaacagc atctgttgca actcacagtc tggggcatca agcagctcca     1260
ggcaagaatc ctggctgtgg aaagatacct aaaggatcaa cagctcctgg ggatttgggg     1320
ttgctctgga aaactcattt gcaccactgc tgtgccttgg aatgctagtt ggagtaataa     1380
atctctggaa cagatttgga atcacacgac ctggatggag tgggacagag aaattaacaa     1440
ttacacaagc ttaatacact ccttaattga agaatcgcaa aaccagcaag aaaagaatga     1500
acaagaatta ttggaattag ataaatgggc aagtttgtgg aattggttta acataacaaa     1560
ttggctgtgg tatataaaat tattcataat gatagtagga ggcttggtag gtttaagaat     1620
agtttttgct gtactttcta tagtgaatag agttaggcag ggatattcac cattatcgtt     1680
tcagacccac ctcccaaccc cgaggggacc cgacaggccc gaaggaatag aagaagaagg     1740
tggagagaga gacagagaca gatccattcg attagtgaac ggatctcgac ggtatcgata     1800
agcttgggag ttccgcgtta cataacttac ggtaaatggc ccgcctggct gaccgcccaa     1860
cgacccccgc ccattgacgt caataatgac gtatgttccc atagtaacgc caatagggac     1920
tttccattga cgtcaatggg tggagtattt acggtaaact gcccacttgg cagtacatca     1980
agtgtatcat atgccaagta cgccccctat tgacgtcaat gacggtaaat ggcccgcctg     2040
gcattatgcc cagtacatga ccttatggga ctttcctact tggcagtaca tctacgtatt     2100
agtcatcgct attaccatgg tgatgcggtt ttggcagtac atcaatgggc gtggatagcg     2160
gtttgactca cggggatttc caagtctcca ccccattgac gtcaatggga gtttgttttg     2220
gcaccaaaat caacgggact ttccaaaatg tcgtaacaac tccgccccat tgacgcaaat     2280
gggcggtagg cgtgtacggt gggaggtcta tataagcaga gctcgtttag tgaaccgtca     2340
gatcgcctgg agacgccatc cacgctgttt tgacctccat agaagacacc gactctagag     2400
gatccactag tccagtgtgg tggaattctg cagatatcaa caagtttgta caaaaaagca     2460
ggcttcgcca ccatggtgag caagggcgag gagctgttca ccggggtggt gcccatcctg     2520
gtcgagctgg acggcgacgt aaacggccac aagttcagcg tgtccggcta gggataacag     2580
ggtaatacct acggcaagct gaccctgaag ttcatctgca ccaccggcaa gctgcccgtg     2640
ccctggccca cctcgtgac cacccctgacc tacggcgtgc agtgcttcag ccgctacccc     2700
gaccacatga agcagcacga cttcttcaag tccgccatgc ccgaaggcta cgtccaggag     2760
cgcaccatct tcttcaagga cgacggcaac tacaagaccc gcgccgaggt gaagttcgag     2820
ggcgacaccc tggtgaaccg catcgagctg aagggcatcg acttcaagga ggacggcaac     2880
atcctggggc acaagctgga gtacaactac aacagccaca acgtctatat catggccgac     2940
aagcagaaga acggcatcaa ggtgaacttc aagatccgcc acaacatcga ggacggcagc     3000
gtgcagctcg ccgaccacta ccagcagaac acccccatcg gcgacggccc cgtgctgctg     3060
cccgacaacc actacctgag cacccagtcc gccctgagca agacccccaa cgagaagcgc     3120
```

```
gatcacatgg tcctgctgga gttcgtgacc gccgccggga tcactctcgg catggacgag    3180
ctgtacaagt aaagcaccca gctttcttgt acaaagtggt tgatatccag cacagtggcg    3240
gccgctcgag tctagagggc ccgcggttcg aaggtaagcc tatccctaac cctctcctcg    3300
gtctcgattc tacgcgtacc ggttagtaat gagtttggaa ttaattctgt ggaatgtgtg    3360
tcagttaggg tgtggaaagt ccccaggctc cccagcaggc agaagtatgc aaagcatgca    3420
tctcaattag tcagcaacca ggtgtggaaa gtccccaggc tccccagcag gcagaagtat    3480
gcaaagcatg catctcaatt agtcagcaac catagtcccg cccctaactc cgcccatccc    3540
gcccctaact ccgcccagtt ccgcccattc tccgccccat ggctgactaa ttttttttat    3600
ttatgcagag gccgaggccg cctctgcctc tgagctattc cagaagtagt gaggaggctt    3660
ttttggaggc ctaggctttt gcaaaaagct cccgggagct gtatatccaa ttttcggatc    3720
tgatcagcac gtgttgacaa ttaatcatcg gcatagtata tcggcatagt ataatacgac    3780
aaggtgagga actaaaccat ggccaagcct ttgtctcaag aagaatccac cctcattgaa    3840
agagcaacgg ctacaatcaa cagcatcccc atctctgaag actacagcgt cgccagcgca    3900
gctctctcta gcgacggccg catcttcact ggtgtcaatg tatatcattt tactggggga    3960
ccttgtgcag aactcgtggt gctgggcact gctgctgctg cggcagctgg caacctgact    4020
tgtatcgtcg cgatcggaaa tgagaacagg ggcatcttga gccctgcgg acggtgccga    4080
caggtgcttc tcgatctgca tcctgggatc aaagccatag tgaaggacag tgatggacag    4140
ccgacggcag ttgggattcg tgaattgctg ccctctggtt atgtgtggga gggctaagca    4200
caattcgagc tcggtacctt taagaccaat gacttacaag gcagctgtag atcttagcca    4260
cttttttaaaa gaaaggggg gactggaagg gctaattcac tcccaacgaa gacaagatct    4320
gctttttgct tgtactgggt ctctctggtt agaccagatc tgagcctggg agctctctgg    4380
ctaactaggg aacccactgc ttaagcctca ataaagcttg ccttgagtgc ttcaagtagt    4440
gtgtgcccgt ctgttgtgtg actctggtaa ctagagatcc ctcagaccct tttagtcagt    4500
gtggaaaatc tctagcagta gtagttcatg tcatcttatt attcagtatt tataacttgc    4560
aaagaaatga atatcagaga gtgagaggaa cttgtttatt gcagcttata atggttacaa    4620
ataaagcaat agcatcacaa atttcacaaa taaagcattt ttttcactgc attctagttg    4680
tggtttgtcc aaactcatca atgtatctta tcatgtctgg ctctagctat cccgccccta    4740
actccgccca tcccgcccct aactccgccc agttccgccc attctccgcc ccatggctga    4800
ctaattttt tttatttatgc agaggccgag gccgcctcgg cctctgagct attccagaag    4860
tagtgaggag gcttttttgg aggcctaggg acgtacccaa ttcgccctat agtgagtcgt    4920
attacgcgcg ctcactggcc gtcgttttac aacgtcgtga ctgggaaaac cctggcgtta    4980
cccaacttaa tcgccttgca gcacatcccc ctttcgccag ctggcgtaat agcgaagagg    5040
cccgcaccga tcgcccttcc caacagttgc gcagcctgaa tggcgaatgg gacgcgccct    5100
gtagcggcgc attaagcgcg gcgggtgtgg tggttacgcg cagcgtgacc gctacacttg    5160
ccagcgccct agcgcccgct cctttcgctt tcttcccttc ctttctcgcc acgttcgccg    5220
gctttccccg tcaagctcta aatcggggc tcccttagg gttccgattt agtgctttac    5280
ggcacctcga ccccaaaaaa cttgattagg gtgatggttc acgtagtggg ccatcgccct    5340
gatagacggt ttttcgccct ttgacgttgg agtccacgtt ctttaatagt ggactcttgt    5400
tccaaactgg aacaacactc aaccctatct cggtctattc ttttgattta agggattt    5460
```

```
tgccgatttc ggcctattgg ttaaaaaatg agctgattta caaaaatttt aacgcgaatt    5520
ttaacaaaat attaacgctt acaatttagg tggcactttt cggggaaatg tgcgcggaac    5580
ccctatttgt ttattttttct aaatacattc aaatatgtat ccgctcatga caataaacc   5640 ctgataaatg cttcaataat attgaaaaag gaagagtatg agtattcaac atttccgtgt   5700
cgcccttatt ccctttttg cggcattttg ccttcctgtt tttgctcacc cagaaacgct    5760
ggtgaaagta aaagatgctg aagatcagtt gggtgcacga gtgggttaca tcgaactgga   5820
tctcaacagc ggtaagatcc ttgagagttt tcgccccgaa gaacgttttc caatgatgag   5880
cactttaaaa gttctgctat gtggcgcggt attatcccgt attgacgccg gcaagagca    5940 actcggtcgc cgcatacact attctcagaa tgacttggtt gagtactcac cagtcacaga   6000
aaagcatctt acgatggca tgacagtaag agaattatgc agtgctgcca taaccatgag   6060
tgataacact gcggccaact tacttctgac aacgatcgga ggaccgaagg agctaaccgc   6120
ttttttgcac aacatggggg atcatgtaac tcgccttgat cgttgggaac cggagctgaa   6180
tgaagccata ccaaacgacg agcgtgacac cacgatgcct gtagcaatgg caacaacgtt   6240
gcgcaaacta ttaactggcg aactacttac tctagcttcc cggcaacaat taatagactg   6300
gatggaggcg gataaagttg caggaccact tctgcgctcg gcccttccgg ctggctggtt   6360
tattgctgat aaatctggag ccggtgagcg tgggtctcgc ggtatcattg cagcactggg   6420
gccagatggt aagccctccc gtatcgtagt tatctacacg acggggagtc aggcaactat   6480
ggatgaacga atagacaga tcgctgagat aggtgcctca ctgattaagc attggtaact   6540
gtcagaccaa gtttactcat atatacttta gattgattta aaacttcatt tttaatttaa   6600
aaggatctag gtgaagatcc tttttgataa tctcatgacc aaaatccctt aacgtgagtt   6660
ttcgttccac tgagcgtcag accccgtaga aaagatcaaa ggatcttctt gagatccttt   6720
ttttctgcgc gtaatctgct gcttgcaaac aaaaaaacca ccgctaccag cggtggtttg   6780
tttgccggat caagagctac caactctttt tccgaaggta actggcttca gcagagcgca   6840
gataccaaat actgttcttc tagtgtagcc gtagttaggc caccacttca agaactctgt   6900
agcaccgcct acatacctcg ctctgctaat cctgttacca gtggctgctg ccagtggcga   6960
taagtcgtgt cttaccgggt tggactcaag acgatagtta ccggataagg cgcagcggtc   7020
gggctgaacg ggggttcgt gcacacagcc cagcttggag cgaacgacct acaccgaact    7080
gagataccta cagcgtgagc tatgagaaag cgccacgctt cccgaaggga aaaggcgga    7140 caggtatccg gtaagcggca gggtcggaac aggagagcgc acgagggagc ttccaggggg   7200
aaacgcctgg tatctttata gtcctgtcgg gtttcgccac ctctgacttg agcgtcgatt   7260
tttgtgatgc tcgtcagggg ggcggagcct atggaaaaac gccagcaacg cggccttttt   7320
acggttcctg gccttttgct ggccttttgc tcacatgttc tttcctgcgt tatcccctga   7380
ttctgtggat aaccgtatta ccgcctttga gtgagctgat accgctcgcc gcagccgaac   7440
gaccgagcgc agcgagtcag tgagcgagga agcggaagag cgcccaatac gcaaaccgcc   7500
tctccccgcg cgttggccga ttcattaatg cagctggcac gacaggtttc ccgactggaa   7560
agcgggcagt gagcgcaacg caattaatgt gagttagctc actcattagg caccccaggc   7620
tttacacttt atgcttccgg ctcgtatgtt gtgtggaatt gtgagcggat aacaatttca   7680
cacaggaaac agctatgacc atgattacgc caagcgcgca attaaccctc actaaggga    7740 acaaaagctg gagctgcaag ctt                                           7763
```

<210> SEQ ID NO 2
<211> LENGTH: 720
<212> TYPE: DNA
<213> ORGANISM: Artificial Sequence
<220> FEATURE:
<223> OTHER INFORMATION: synthesized, Inactive GFP

<400> SEQUENCE: 2

```
atggtgagca agggcgagga gctgttcacc ggggtggtgc ccatcctggt cgagctggac        60
ggcgacgtaa acggccacaa gttcagcgtg tccggctagg gataacaggg taatacctac       120
ggcaagctga ccctgaagtt catctgcacc accggcaagc tgcccgtgcc ctggcccacc       180
ctcgtgacca ccctgaccta cggcgtgcag tgcttcagcc gctaccccga ccacatgaag       240
cagcacgact tcttcaagtc cgccatgccc gaaggctacg tccaggagcg caccatcttc       300
ttcaaggacg acggcaacta caagacccgc gccgaggtga agttcgaggg cgacaccctg       360
gtgaaccgca tcgagctgaa gggcatcgac ttcaaggagg acggcaacat cctggggcac       420
aagctggagt acaactacaa cagccacaac gtctatatca tggccgacaa gcagaagaac       480
ggcatcaagg tgaacttcaa gatccgccac aacatcgagg acggcagcgt gcagctcgcc       540
gaccactacc agcagaacac ccccatcggc gacggccccg tgctgctgcc cgacaaccac       600
tacctgagca cccagtccgc cctgagcaaa gaccccaacg agaagcgcga tcacatggtc       660
ctgctggagt tcgtgaccgc cgccgggatc actctcggca tggacgagct gtacaagtaa       720
```

<210> SEQ ID NO 3
<211> LENGTH: 20
<212> TYPE: DNA
<213> ORGANISM: Artificial Sequence
<220> FEATURE:
<223> OTHER INFORMATION: synthesized, gRNA Sequence Targeting Inactive
      GFP Gene

<400> SEQUENCE: 3

```
gtgtccggct agggataaca                                                    20
```

<210> SEQ ID NO 4
<211> LENGTH: 88
<212> TYPE: DNA
<213> ORGANISM: Artificial Sequence
<220> FEATURE:
<223> OTHER INFORMATION: synthesized, DD-GFP-C-88SS DONOR DNA OLIGO

<400> SEQUENCE: 4

```
ggacggcgac gtaaacggcc acaagttcag cgtgtccggc gagggcgagg gcgatgccac        60
ctacggcaag ctgaccctga agttcatc                                           88
```

<210> SEQ ID NO 5
<211> LENGTH: 4206
<212> TYPE: DNA
<213> ORGANISM: Artificial Sequence
<220> FEATURE:
<223> OTHER INFORMATION: synthesized, HA TAG-CAS9

<400> SEQUENCE: 5

```
atgtacccat acgatgttcc agattacgct ggtaccgagc tcggatccga caagaagtat        60
agcatcggcc tggatatcgg cacaaactcc gtgggctggg ccgtgatcac cgacgagtac       120
aaggtgccaa gcaagaagtt taaggtgctg ggcaacaccg atagacactc catcaagaag       180
aatctgatcg gcgccctgct gttcgactct ggcgagacag ccgaggccac acggctgaag       240
agaaccgccc ggagaaggta tacacgccgg aagaatagga tctgctacct gcaggagatc       300
```

```
ttcagcaacg agatggccaa ggtggacgat tctttctttc accgcctgga ggagagcttc    360
ctggtggagg aggataagaa gcacgagcgg caccctatct tggcaacat cgtggacgag      420 gtggcctatc acgagaagta cccaacaatc tatcacctga ggaagaagct ggtggactcc    480
accgataagg ccgacctgcg cctgatctat ctggccctgg cccacatgat caagttccgg    540
ggccactttc tgatcgaggg cgatctgaac ccagacaata gcgatgtgga caagctgttc    600
atccagctgg tgcagaccta caatcagctg tttgaggaga ccccatcaa tgcctctgga     660 gtggacgcaa aggcaatcct gagcgccaga ctgtccaagt ctagaaggct ggagaacctg    720
atcgcccagc tgccaggcga agaagaac ggcctgtttg caatctgat cgccctgtcc       780 ctgggcctga cacccaactt caagtctaat tttgatctgg ccgaggacgc caagctgcag    840
ctgtccaagg acacctatga cgatgacctg gataacctgc tggcccagat cggcgatcag    900
tacgccgacc tgttcctggc cgccaagaat ctgtctgacg ccatcctgct gagcgatatc    960
ctgcgcgtga acaccgagat cacaaaggcc cccctgagcg cctccatgat caagagatat   1020
gacgagcacc accaggatct gaccctgctg aaggccctgg tgaggcagca gctgcctgag   1080
aagtacaagg atcttctt tgatcagagc aagaatggat acgcaggata tatcgacgga     1140
ggagcatccc aggaggagtt ctacaagttt atcaagccta tcctggagaa gatggacggc   1200
acagaggagc tgctggtgaa gctgaatcgg gaggacctgc tgaggaagca gcgcaccttt   1260
gataacggca gcatccctca ccagatccac ctgggagagc tgcacgcaat cctgcgccgg   1320
caggaggact tctacccatt tctgaaggat aaccgggaga gatcgagaa gatcctgaca    1380 ttcagaatcc cctactatgt gggacctctg gcccggggca atagcagatt tgcctggatg   1440
acccgcaagt ccgaggagac aatcacaccc tggaacttcg aggaggtggt ggataagggc   1500
gcctctgccc agagcttcat cgagcggatg accaattttg acaagaacct gcctaatgag   1560
aaggtgctgc caaagcactc tctgctgtac gagtatttca ccgtgtataa cgagctgaca   1620
aaggtgaagt acgtgaccga gggcatgaga aagcctgcct tcctgagcgg cgagcagaag   1680
aaggccatcg tggacctgct gtttaagacc aataggaagg tgacagtgaa gcagctgaag   1740
gaggactatt tcaagaagat cgagtgtttt gattctgtgg agatcagcgg cgtggaggac   1800
aggtttaacg cctccctggg cacctaccac gatctgctga agatcatcaa ggataaggac   1860
ttcctggaca cgaggagaa tgaggatatc ctggaggaca tcgtgctgac cctgacactg   1920
tttgaggata gggagatgat cgaggagcgc ctgaagacat atgcccacct gttcgatgac    1980
aaagtgatga agcagctgaa gagaaggcgc tacaccggat ggggccggct gagcagaaag    2040
ctgatcaatg gcatccgcga caagcagtct ggcaagacaa tcctggactt tctgaagagc    2100
gatggcttcg ccaaccggaa cttcatgcag ctgatccacg atgactccct gaccttcaag    2160
gaggatatcc agaaggcaca ggtgtctgga cagggcgaca gcctgcacga gcacatcgcc    2220
aacctggccg gctctcctgc catcaagaag ggcatcctgc agaccgtgaa ggtggtggac    2280
gagctggtga aagtgatggg caggcacaag ccagagaaca tcgtgatcga gatggcccgc    2340
gagaatcaga ccacacagaa gggccagaag aactcccggg agagaatgaa gagaatcgag    2400
gagggcatca aggagctggg ctctcagatc ctgaaggagc accccgtgga gaacacacag    2460
ctgcagaatg agaagctgta tctgtactat ctgcagaatg ccgggatat gtacgtggac    2520 caggagctgg atatcaacag actgtctgat tatgacgtgg atcacatcgt gccacagtcc    2580
ttcctgaagg atgactctat cgacaataag gtgctgacca ggagcgacaa gaaccgcggc    2640
```

```
aagtccgata atgtgccctc tgaggaggtg gtgaagaaga tgaagaacta ctggaggcag    2700
ctgctgaatg ccaagctgat cacacagagg aagtttgata acctgaccaa ggcagagagg    2760
ggaggcctgt ccgagctgga caaggccggc ttcatcaagc ggcagctggt ggagacaaga    2820
cagatcacaa agcacgtggc ccagatcctg gattctagaa tgaacacaaa gtacgatgag    2880
aatgacaagc tgatcaggga ggtgaaagtg atcaccctga agtccaagct ggtgtctgac    2940
tttaggaagg atttccagtt ttataaggtg cgcgagatca acaattatca ccacgcccac    3000
gacgcctacc tgaacgccgt ggtgggcaca gccctgatca gaagtacccc taagctggag    3060
tccgagttcg tgtacggcga ctataaggtg tacgatgtgc gcaagatgat cgccaagtct    3120
gagcaggaga tcggcaaggc caccgccaag tatttctttt acagcaacat catgaatttc    3180
tttaagaccg agatcacact ggccaatggc gagatcagga gcgcccact gatcgagaca    3240 aacggcgaga caggcgagat cgtgtgggac aagggcaggg attttgccac cgtgcgcaag    3300
gtgctgagca tgccccaagt gaatatcgtg aagaagaccg aggtgcagac aggcggcttc    3360
tccaaggagt ctatcctgcc taagcggaac tccgataagc tgatcgccag aaagaaggac    3420
tgggacccca gaagtatgg cggcttcgac agccctacag tggcctactc cgtgctggtg    3480
gtggccaagg tggagaaggg caagagcaag aagctgaagt ccgtgaagga gctgctgggc    3540
atcaccatca tggagcgcag ctccttcgag aagaatccta tcgatttct ggaggccaag    3600 ggctataagg aggtgaagaa ggacctgatc atcaagctgc caaagtactc tctgtttgag    3660
ctggagaacg gaaggaagag aatgctggca agcgccggag agctgcagaa gggcaatgag    3720 ctggcccctgc cctccaagta cgtgaacttc ctgtatctgg cctcccacta cgagaagctg    3780
aagggctctc ctgaggataa cgagcagaag cagctgtttg tggagcagca aagcactat    3840 ctggacgaga tcatcgagca gatcagcgag ttctccaaga gagtgatcct ggccgacgcc    3900
aatctggata aggtgctgtc cgcctacaac aagcaccggg ataagccaat cagagagcag    3960
gccgagaata tcatccacct gtttaccctg acaaacctgg gagcaccagc agccttcaag    4020 tatttttgaca ccacaatcga taggaagcgg tacaccagca caaggaggt gctggacgcc    4080 acactgatcc accagtccat caccggcctg tacgagacac ggatcgacct gtctcagctg    4140
ggaggcgata gcggccgc agcaaccaag aaggcaggac aggccaagaa gaagaaggaa    4200
ttctaa                                                              4206
```

<210> SEQ ID NO 6
<211> LENGTH: 6963
<212> TYPE: DNA
<213> ORGANISM: Artificial Sequence
<220> FEATURE:
<223> OTHER INFORMATION: synthesized, CTIP(ON)-CAS9-HA

<400> SEQUENCE: 6

```
atgaacatct cgggaagcag ctgtggaagc cctaactctg cagatacatc tagtgacttt      60
aaggaccttt ggacaaaaact aaaagaatgt catgatagag aagtacaagg tttacaagta     120
aaagtaacca agctaaaaca ggaacgaatc ttagatgcac aaagactaga agagttcttc     180
accaaaaatc aacagctgag ggaacagcag aaagtcctc atgaaaccat taagttttta     240
gaagatcggt taagagcagg cttatgtgat cgctgtgcag taactgaaga acatatgcgg     300
aaaaaacagc aagagtttga aaatatccgg cagcagaatc ttaaacttat tacagaactt     360
atgaatgaaa ggaatactct acaggaagaa ataaaaagc tttctgaaca actccagcag     420
aaaattgaga tgatcaaca gcatcaagca gctgagcttg aatgtgagga agacgttatt     480
```

```
ccagattcac cgataacagc cttctcattt tctggcgtta accggctacg aagaaaggag    540
aacccccatg tccgatacat agaacaaaca catactaaat tggagcactc tgtgtgtgca    600
aatgaaatga gaaagttttc caagtcttca actcatccac aacataatcc taatgaaaat    660
gaaattctag tagctgacac ttatgaccaa gatcaatctc caatggccaa agcacatgga    720
acaagcagct ataccctga taagtcatct tttaatttag ctacagttgt tgctgaaaca     780
cttggacttg gtgttcaaga agaatctgaa actcaaggtc ccatgagccc ccttggtgat    840
gagctctacc actgtctgga aggaaatcac aagaaacagc cttttgagga atctacaaga    900
aatactgaag atagtttaag attttcagat tctacttcaa agactcctcc tcaagaagaa    960
ttacctacgc gagtgtcatc tcctgtattt ggagctacct ctagtatcaa agtggttta   1020 gatttgaata caagtttgga cccttctctt ttacagcctg gaaaaaaaa acatctgaaa   1080 acactccctt ttagcaacac ttgtatatct agattagaaa aaactagatc aaaatctgaa   1140
gatagtgccc ttttcacaca tcacagtctt gggtctgaag tgaacaagat cattatccag   1200
tcatctaata acagatact tataaataaa aatataagtg aatccctagg tgaacagaat    1260
aggactgagt acgtaaaga ttctaacact gatagacatt tggagcccct gaaatcattg    1320
ggaggccgaa catccaaaag gaagaaaact gaggaagaaa gtgaacatga agtaagctgc   1380
ccccaagctt cttttgataa agaaaatgct ttcccttttc caatggataa tcagtttttcc  1440 atgaatggag actgtgtgat ggataaacct ctggatctgt ctgatcgatt ttcagctatt   1500
cagcgtcaag agaaaagcca aggaagtgag acttctaaaa acaaatttag gcaagtgact   1560
ctttatgagg ctttgaggac cattccaaag ggcttttcct caagccgtaa ggcctcagat   1620
ggcaactgca cgttgcccaa agattcccca ggggagccct gttcacagga atgcatcatc   1680
cttcagccct tgaataaatg ctctccagac aataaaccat cattacaaat aaaagaagaa   1740
aatgctgtct ttaaaattcc tctacgtcca cgtgaaagtt tggagactga gaatgtttta   1800
gatgacataa ggagtgctgg ttctcatgag ccaataaaaa tacaaaccag gtcagaccat   1860
ggaggatgtg aacttgcatc agttcttcag ttaaatccat gtagaactgg taaaataaag   1920
tctctacaaa acaaccaaga tgtatccttt gaaaatatcc agtggagtat agatccggga   1980
gcagaccttt ctcagtataa aatggatgtt actgtaatag atacaaagga tggcagtcag   2040
tcaaaattag gaggagagac agtggacatg gactgtacat tggttagtga aaccgttctc   2100
ttaaaaatga gaagcaaga gcagaaggga gaaaaaagtt caaatgaaga aagaaaaatg   2160
aatgatagct tggaagatat gtttgatcgg acaacacatg aagagtatga atcctgtttg   2220
gcagacagtt tctcccaagc agcagatgaa gaggaggaat tgtctactgc cacaaagaaa   2280
ctacacactc atggtgataa acaagacaaa gtcaagcaga aagcgtttgt ggagccgtat   2340
tttaaaggtg atgaaagaga gactagcttg caaaattttc ctcatattga ggtggttcgg   2400
aaaaaagagg agagaagaaa actgcttggg cacacgtgta aggaatgtga aatttattat   2460
gcagatatgc cagcagaaga aagagaaaag aaattggctt cctgctcaag acaccgattc   2520
cgctacattc cacccaacga tccagagaat ttttgggaag ttggttttcc ttccgatcag   2580
acttgtatgg aaagaggtta tattaaggaa gatcttgatc cttgtcctcg tccaaaaaga   2640
cgtcagcctt acaacgcaat attttctcca aaaggcaagg agcagaagac aggatccggc   2700
agcaccagcg gcagcggcaa gcccggcagc ggcgagggca gcaccaaggg cgaattcgac   2760
aagaagtaca gcatcggcct ggatatcggc acaaactccg tgggctgggc cgtgatcacc   2820
```

```
gacgagtaca aggtgcccag caagaagttt aaggtgctgg gcaacaccga tagacactcc    2880
atcaagaaga atctgatcgg cgccctgctg ttcgactctg gcgagacagc agaggcaaca    2940
aggctgaaga ggaccgcacg gagaaggtat acacgccgga agaataggat ctgctacctg    3000
caggagatct tcagcaacga gatggccaag gtggacgatt ctttctttca ccgcctggag    3060
gagagcttcc tggtggagga ggataagaag cacgagcggc accctatctt tggcaacatc    3120
gtggacgagg tggcctatca cgagaagtac ccaacaatct atcacctgag gaagaagctg    3180
gtggactcca ccgataaggc cgacctgcgc ctgatctatc tggccctggc ccacatgatc    3240
aagttccggg gccactttct gatcgagggc gatctgaacc ccgacaatag cgatgtggac    3300
aagctgttca tccagctggt gcagacctac aatcagctgt ttgaggagaa ccctatcaat    3360
gcctctggag tggacgcaaa ggcaatcctg agcgccaggc tgtccaagtc tagaaggctg    3420
gagaacctga tcgcccagct gcccggcgag aagaagaacg gcctgtttgg caatctgatc    3480
gccctgtccc tgggcctgac acctaacttc aagtctaatt ttgatctggc cgaggacgcc    3540
aagctgcagc tgtccaagga cacctatgac gatgacctgg ataacctgct ggcccagatc    3600
ggcgatcagt acgccgacct gttcctggcc gccaagaatc tgtctgacgc catcctgctg    3660
agcgatatcc tgcgcgtgaa caccgagatc acaaaggccc ctctgagcgc ctccatgatc    3720
aagagatatg acgagcacca ccaggatctg accctgctga aggccctggt gaggcagcag    3780
ctgccagaga agtacaagga gatcttcttt gatcagagca gaatggata cgcaggatat    3840 atcgacggag gagcatccca ggaggagttc tacaagttta tcaagccaat cctggagaag    3900
atggacggca cagaggagct gctggtgaag ctgaatcggg aggacctgct gcggaagcag    3960
agaacctttg ataacggcag catcccacac cagatccacc tgggagagct gcacgcaatc    4020
ctgcgccggc aggaggactt ctaccccttt ctgaaggata accggagaa gatcgagaag    4080 atcctgacat tcagaatccc atactatgtg ggaccactgg cccggggcaa tagcagattt    4140
gcctggatga cccgcaagtc cgaggagaca atcacaccct ggaacttcga ggaggtggtg    4200
gataagggcg cctctgccca gagcttcatc gagcggatga ccaattttga caagaacctg    4260
cctaatgaga aggtgctgcc aaagcactct ctgctgtacg agtatttcac cgtgtataac    4320
gagctgacaa aggtgaagta cgtgaccgag ggcatgagaa agcctgcctt cctgagcggc    4380
gagcagaaga aggccatcgt ggacctgctg tttaagacca ataggaaggt gacagtgaag    4440
cagctgaagg aggactattt caagaagatc gagtgttttg attccgtgga gatctctggc    4500
gtggaggacc gctttaacgc ctccctgggc acctaccacg atctgctgaa gatcatcaag    4560
gataaggact tcctggacaa cgaggagaat gaggatatcc tggaggacat cgtgctgacc    4620
ctgacactgt ttgaggatag ggagatgatc gaggagcgcc tgaagacata tgcccacctg    4680
ttcgatgaca aagtgatgaa gcagctgaag agaaggcgct acaccggatg gggcaggctg    4740
agccgcaagc tgatcaatgg catccgcgac aagcagtctg caagacaat cctggacttt    4800 ctgaagagcg atggcttcgc caaccggaac ttcatgcagc tgatccacga tgactccctg    4860
accttcaagg aggatatcca gaaggcacag gtgtctggac agggcgacag cctgcacgag    4920
cacatcgcca acctggccgg ctctccagcc atcaagaagg gcatcctgca gaccgtgaag    4980
gtggtggatg agctggtgaa agtgatgggc aggcacaagc ccgagaacat cgtgatcgag    5040
atggcccgcg agaatcagac cacacagaag ggccagaaga actcccggga gagaatgaag    5100
agaatcgagg agggcatcaa ggagctgggc tctcagatcc tgaaggagca ccctgtggag    5160
aacacacagc tgcagaatga gaagctgtat ctgtactatc tgcagaatgg ccgggatatg    5220
```

```
tacgtggacc aggagctgga tatcaacaga ctgtctgatt atgacgtgga tcacatcgtg    5280
ccccagtcct tcctgaagga tgactctatc gacaataagg tgctgaccag gagcgacaag    5340
aaccgcggca gtccgataa tgtgccttct gaggaggtgg tgaagaagat gaagaactac    5400
tggaggcagc tgctgaatgc caagctgatc acacagagga gtttgataa cctgaccaag    5460 gcagagaggg gaggcctgtc cgagctggac aaggccggct tcatcaagcg gcagctggtg    5520
gagacaagac agatcacaaa gcacgtggcc cagatcctgg attctagaat gaacacaaag    5580
tacgatgaga atgacaagct gatcagggag gtgaaagtga tcaccctgaa gagcaagctg    5640
gtgtccgact ttaggaagga tttccagttt tataaggtgc gcgagatcaa caattatcac    5700
cacgcccacg acgcctacct gaacgccgtg gtgggcacag ccctgatcaa gaagtaccct    5760
aagctggaga gcgagttcgt gtacggcgac tataaggtgt acgatgtgcg gaagatgatc    5820
gccaagtctg agcaggagat cggcaaggcc accgccaagt atttctttta cagcaacatc    5880
atgaatttct ttaagaccga gatcacactg gccaatggcg agatcaggaa gcgcccactg    5940
atcgagacaa acggcgagac aggcgagatc gtgtgggaca agggcaggga ttttgccacc    6000
gtgcgcaagg tgctgagcat gcctcaagtg aatatcgtga agaagaccga ggtgcagaca    6060
ggcggcttct ccaaggagtc tatcctgcca aagcggaact ccgataagct gatcgccaga    6120
aagaaggact gggaccccaa gaagtatggc ggcttcgaca cccccacagt ggcctactcc    6180
gtgctggtgg tggccaaggt ggagaagggc aagagcaaga agctgaagtc cgtgaaggag    6240
ctgctgggca tcaccatcat ggagcggagc agcttcgaga gaaacccaat cgatttcctg    6300
gaggccaagg gctataagga ggtgaagaag gacctgatca tcaagctgcc caagtactct    6360
ctgtttgagc tggagaacgg aaggaagaga atgctggcaa gcgccggaga gctgcagaag    6420
ggcaatgagc tggccctgcc ttccaagtac gtgaacttcc tgtatctggc ctcccactac    6480
gagaagctga agggctctcc agaggataac gagcagaagc agctgtttgt ggagcagcac    6540
aagcactatc tggacgagat catcgagcag atcagcgagt tctccaagag agtgatcctg    6600
gccgacgcca atctggataa ggtgctgtcc gcctacaaca gcaccgggga caagccccatc    6660 agagagcagg ccgagaatat catccacctg ttcaccctga caaacctggg agcacctgca    6720
gccttcaagt attttgacac cacaatcgat aggaagcggt acaccagcac aaaggaggtg    6780
ctggatgcca cactgatcca ccagtccatc accggcctgt acgagacacg gatcgacctg    6840
tctcagctgg gaggcgataa gcggcccgca gcaaccaaga aggcaggaca ggccaagaag    6900
aagaaggacc tggagctcga gtctagaggg ccctacccat acgatgttcc agattacgct    6960
tga                                                                  6963
```

<210> SEQ ID NO 7
<211> LENGTH: 6966
<212> TYPE: DNA
<213> ORGANISM: Artificial Sequence
<220> FEATURE:
<223> OTHER INFORMATION: HA-CAS9-CTIP(ON)

<400> SEQUENCE: 7

```
atgtacccat acgatgttcc agattacgct ggtaccgagc tcggatccga caagaagtat      60
agcatcggcc tggatatcgg cacaaactcc gtgggctggg ccgtgatcac cgacgagtac    120
aaggtgccaa gcaagaagtt taaggtgctg ggcaacaccg atagacactc catcaagaag    180
aatctgatcg gcgcccctgct gttcgactct ggcgagacag ccgaggccac acggctgaag    240
```

```
agaaccgccc ggagaaggta tacacgccgg aagaatagga tctgctacct gcaggagatc    300
ttcagcaacg agatggccaa ggtggacgat tctttctttc accgcctgga ggagagcttc    360
ctggtggagg aggataagaa gcacgagcgg caccctatct ttggcaacat cgtggacgag    420
gtggcctatc acgagaagta cccaacaatc tatcacctga ggaagaagct ggtggactcc    480
accgataagg ccgacctgcg cctgatctat ctggccctgg cccacatgat caagttccgg    540
ggccactttc tgatcgaggg cgatctgaac ccagacaata gcgatgtgga caagctgttc    600
atccagctgg tgcagaccta caatcagctg tttgaggaga cccccatcaa tgcctctgga    660
gtggacgcaa aggcaatcct gagcgccaga ctgtccaagt ctagaaggct ggagaacctg    720
atcgcccagc tgccaggcga aaagaagaac ggcctgtttg gcaatctgat cgccctgtcc    780
ctgggcctga cacccaactt caagtctaat tttgatctgg ccgaggacgc caagctgcag    840
ctgtccaagg acacctatga cgatgacctg gataacctgc tggcccagat cggcgatcag    900
tacgccgacc tgttcctggc cgccaagaat ctgtctgacg ccatcctgct gagcgatatc    960
ctgcgcgtga acaccgagat cacaaaggcc cccctgagcg cctccatgat caagagatat   1020
gacgagcacc accaggatct gaccctgctg aaggccctgg tgaggcagca gctgcctgag   1080
aagtacaagg agatcttctt tgatcagagc aagaatggac acgcaggata tatcgacgga   1140
ggagcatccc aggaggagtt ctacaagttt atcaagccta tcctggagaa gatggacggc   1200
acagaggagc tgctggtgaa gctgaatcgg gaggacctgc tgaggaagca gcgcacccttt  1260 gataacggca gcatccctca ccagatccac ctgggagagc tgcacgcaat cctgcgccgg   1320
caggaggact tctacccatt tctgaaggat aaccgggaga gatcgagaa gatcctgaca    1380 ttcagaatcc cctactatgt gggaccctctg gcccggggca atagcagatt tgcctggatg   1440
acccgcaagt ccgaggagac aatcacaccc tggaacttcg aggaggtggt ggataagggc   1500
gcctctgccc agagcttcat cgagcggatg accaattttg acaagaacct gcctaatgag   1560
aaggtgctgc caaagcactc tctgctgtac gagtatttca ccgtgtataa cgagctgaca   1620
aaggtgaagt acgtgaccga gggcatgaga aagcctgcct tcctgagcgg cgagcagaag   1680
aaggccatcg tggacctgct gtttaagacc aataggaagg tgacagtgaa gcagctgaag   1740
gaggactatt tcaagaagat cgagtgtttt gattctgtgg agatcagcgg cgtggaggac   1800
aggtttaacg cctccctggg cacctaccac gatctgctga agatcatcaa ggataaggac   1860
ttcctggaca cgaggagaa tgaggatatc ctggaggaca tcgtgctgac cctgacactg   1920
tttgaggata gggagatgat cgaggagcgc ctgaagacat atgcccacct gttcgatgac   1980
aaagtgatga agcagctgaa gagaaggcgc tacaccggat ggggccggct gagcagaaag   2040
ctgatcaatg gcatccgcga caagcagtct ggcaagacaa tcctggactt tctgaagagc   2100
gatggcttcg ccaaccggaa cttcatgcag ctgatccacg atgactccct gaccttcaag   2160
gaggatatcc agaaggcaca ggtgtctgga caggcgaca gcctgcacga gcacatcgcc   2220
aacctggccg gctctcctgc catcaagaag ggcatcctgc agaccgtgaa ggtggtggac   2280
gagctggtga agtgatggg caggcacaag ccagagaaca tcgtgatcga gatggcccgc   2340
gagaatcaga ccacacagaa gggccagaag aactcccggg agagaatgaa gagaatcgag   2400
gagggcatca aggagctggg ctctcagatc ctgaaggagc accccgtgga gaacacacag   2460
ctgcagaatg agaagctgta tctgtactat ctgcagaatg ccgggatat gtacgtggac   2520 caggagctgg atatcaacag actgtctgat tatgacgtgg atcacatcgt gccacagtcc   2580
ttcctgaagg atgactctat cgacaataag gtgctgacca ggagcgacaa gaaccgcggc   2640
```

```
aagtccgata atgtgccctc tgaggaggtg gtgaagaaga tgaagaacta ctggaggcag    2700
ctgctgaatg ccaagctgat cacacagagg aagtttgata acctgaccaa ggcagagagg    2760
ggaggcctgt ccgagctgga caaggccggc ttcatcaagc ggcagctggt ggagacaaga    2820
cagatcacaa agcacgtggc ccagatcctg gattctagaa tgaacacaaa gtacgatgag    2880
aatgacaagc tgatcaggga ggtgaaagtg atcaccctga agtccaagct ggtgtctgac    2940
tttaggaagg atttccagtt ttataaggtg cgcgagatca acaattatca ccacgcccac    3000
gacgcctacc tgaacgccgt ggtgggcaca gccctgatca agaagtaccc taagctggag    3060
tccgagttcg tgtacggcga ctataaggtg tacgatgtgc gcaagatgat cgccaagtct    3120
gagcaggaga tcggcaaggc caccgccaag tatttctttt acagcaacat catgaatttc    3180
tttaagaccg agatcacact ggccaatggc gagatcagga agcgcccact gatcgagaca    3240
aacggcgaga caggcgagat cgtgtgggac aagggcaggg attttgccac cgtgcgcaag    3300
gtgctgagca tgccccaagt gaatatcgtg aagaagaccg aggtgcagac aggcggcttc    3360
tccaaggagt ctatcctgcc taagcggaac tccgataagc tgatcgccag aaagaaggac    3420
tgggacccca gaagtatgg cggcttcgac agccctacag tggcctactc cgtgctggtg    3480
gtggccaagg tggagaaggg caagagcaag aagctgaagt ccgtgaagga gctgctgggc    3540
atcaccatca tggagcgcag ctccttcgag aagaatccta tcgattttct ggaggccaag    3600
ggctataagg aggtgaagaa ggacctgatc atcaagctgc caaagtactc tctgtttgag    3660
ctggagaacg gaaggaagag aatgctggca agcgccggag agctgcagaa gggcaatgag    3720
ctggccctgc cctccaagta cgtgaacttc ctgtatctgg cctcccacta cgagaagctg    3780
aagggctctc ctgaggataa cgagcagaag cagctgtttg tggagcagca aagcactat    3840 ctggacgaga tcatcgagca gatcagcgag ttctccaaga gagtgatcct ggccgacgcc    3900
aatctggata aggtgctgtc cgcctacaac aagcaccggg ataagccaat cagagagcag    3960
gccgagaata tcatccacct gtttaccctg acaaacctgg gagcaccagc agccttcaag    4020
tattttgaca ccacaatcga taggaagcgg tacaccagca caaggaggt gctggacgcc    4080 acactgatcc accagtccat caccggcctg tacgagacac ggatcgacct gtctcagctg    4140
ggaggcgata gcggcccgc agcaaccaag aaggcaggac aggccaagaa gaagaaggaa    4200
ttcggcagca ccagcggcag cggcaagccc ggcagcggcg agggcagcac caagggcctc    4260
gagatgaaca tctcgggaag cagctgtgga agccctaact ctgcagatac atctagtgac    4320
tttaaggacc tttggacaaa actaaaagaa tgtcatgata gaagtaca aggtttacaa    4380 gtaaagtaa ccaagctaaa acaggaacga atcttagatg cacaaagact agaagagttc    4440
ttcaccaaaa atcaacagct gagggaacag cagaaagtcc ttcatgaaac cattaaagtt    4500
ttagaagatc ggttaagagc aggcttatgt gatcgctgtg cagtaactga agaacatatg    4560
cggaaaaaac agcaagagtt tgaaaatatc cggcagcaga atcttaaact tattacagaa    4620
cttatgaatg aaaggaatac tctacaggaa gaaaataaaa agctttctga caactccag    4680 cagaaaattg agaatgatca acagcatcaa gcagctgagc ttgaatgtga ggaagacgtt    4740
attccagatt caccgataac agccttctca ttttctggcg ttaaccggct acgaagaag    4800 gagaaccccc atgtccgata catagaacaa acacatacta aattggagca ctctgtgtgt    4860
gcaaatgaaa tgagaaaagt ttccaagtct tcaactcatc cacaacataa tcctaatgaa    4920
aatgaaattc tagtagctga cacttatgac caagatcaat ctccaatggc caaagcacat    4980
```

-continued

```
ggaacaagca gctatacccc tgataagtca tcttttaatt tagctacagt tgttgctgaa      5040
acacttggac ttggtgttca agaagaatct gaaactcaag gtcccatgag ccccttggt      5100 gatgagctct accactgtct ggaaggaaat cacaagaaac agccttttga ggaatctaca      5160
agaaatactg aagatagttt aagattttca gattctactt caaagactcc tcctcaagaa      5220
gaattaccta cgcgagtgtc atctcctgta tttggagcta cctctagtat caaaagtggt      5280
ttagatttga atacaagttt ggacccttct cttttacagc ctgggaaaaa aaacatctg      5340 aaaacactcc cttttagcaa cacttgtata tctagattag aaaaaactag atcaaaatct      5400
gaagatagtg ccctttttcac acatcacagt cttgggtctg aagtgaacaa gatcattatc      5460
cagtcatcta ataaacagat acttataaat aaaaatataa gtgaatccct aggtgaacag      5520
aataggactg agtacggtaa agattctaac actgatagac atttggagcc cctgaaatca      5580
ttgggaggcc gaacatccaa aaggaagaaa actgaggaag aaagtgaaca tgaagtaagc      5640
tgcccccaag cttcttttga taagaaaat gctttcccctt ttccaatgga taatcagttt      5700
tccatgaatg gagactgtgt gatggataaa cctctggatc tgtctgatcg attttcagct      5760
attcagcgtc aagagaaaag ccaaggaagt gagacttcta aaaacaaatt taggcaagtg      5820
actctttatg aggctttgag gaccattcca aagggctttt cctcaagccg taaggcctca      5880
gatggcaact gcacgttgcc caaagattcc ccaggggagc cctgttcaca ggaatgcatc      5940
atccttcagc ccttgaataa atgctctcca gacaataaac catcattaca aataaaagaa      6000
gaaaatgctg tctttaaaat tcctctacgt ccacgtgaaa gtttggagac tgagaatgtt      6060
ttagatgaca taaggagtgc tggttctcat gagccaataa aaatacaaac caggtcagac      6120
catggaggat gtgaacttgc atcagttctt cagttaaatc catgtagaac tggtaaaata      6180
aagtctctac aaaacaacca agatgtatcc tttgaaaata tccagtggag tatagatccg      6240
ggagcagacc tttctcagta taaaatggat gttactgtaa tagatacaaa ggatggcagt      6300
cagtcaaaat taggaggaga gacagtggac atggactgta cattggttag tgaaaccgtt      6360
ctcttaaaaa tgaagaagca agagcagaag ggagaaaaaa gttcaaatga agaaagaaaa      6420
atgaatgata gcttggaaga tatgtttgat cggacaacac atgaagagta tgaatcctgt      6480
ttggcagaca gtttctccca gcagcagat gaagaggagg aattgtctac tgccacaaag      6540
aaactacaca ctcatggtga taaacaagac aaagtcaagc agaaagcgtt tgtggagccg      6600
tattttaaag gtgatgaaag agagactagc ttgcaaaatt ttcctcatat tgaggtggtt      6660
cggaaaaaag aggagagaag aaaactgctt gggcacacgt gtaaggaatg tgaaatttat      6720
tatgcagata tgccagcaga agaaagagaa aagaaattgg cttcctgctc aagacaccga      6780
ttccgctaca ttccacccaa cgatccagag aattttgggg aagttggttt tccttccgat      6840
cagacttgta tggaaagagg ttatattaag gaagatcttg atccttgtcc tcgtccaaaa      6900
agacgtcagc cttacaacgc aatattttct ccaaaaggca aggagcagaa gacagggccc      6960
gtttaa                                                                6966
```

<210> SEQ ID NO 8
<211> LENGTH: 6399
<212> TYPE: DNA
<213> ORGANISM: Artificial Sequence
<220> FEATURE:
<223> OTHER INFORMATION: synthesized, HA-CAS9-MRE11

<400> SEQUENCE: 8

```
atgtacccat acgatgttcc agattacgct ggtaccgagc tcggatccga caagaagtat       60
```

```
agcatcggcc tggatatcgg cacaaactcc gtgggctggg ccgtgatcac cgacgagtac    120
aaggtgccaa gcaagaagtt taaggtgctg ggcaacaccg atagacactc catcaagaag    180
aatctgatcg gcgccctgct gttcgactct ggcgagacag ccgaggccac acggctgaag    240
agaaccgccc ggagaaggta tacacgccgg aagaatagga tctgctacct gcaggagatc    300
ttcagcaacg agatggccaa ggtggacgat tctttctttc accgcctgga ggagagcttc    360
ctggtggagg aggataagaa gcacgagcgg caccctatct tggcaacat cgtggacgag     420 gtggcctatc acgagaagta cccaacaatc tatcacctga ggaagaagct ggtggactcc    480
accgataagg ccgacctgcg cctgatctat ctggccctgg cccacatgat caagttccgg    540
ggccactttc tgatcgaggg cgatctgaac ccagacaata gcgatgtgga caagctgttc    600
atccagctgt gcagacccta caatcagctg tttgaggaga cccccatcaa tgcctctgga    660
gtggacgcaa aggcaatcct gagcgccaga ctgtccaagt ctagaaggct ggagaacctg    720
atcgcccagc tgccaggcga aaagaagaac ggcctgtttg gcaatctgat cgccctgtcc    780
ctgggcctga cacccaactt caagtctaat tttgatctgg ccgaggacgc caagctgcag    840
ctgtccaagg acacctatga cgatgacctg gataacctgc tggcccagat cggcgatcag    900
tacgccgacc tgttcctggc cgccaagaat ctgtctgacg ccatcctgct gagcgatatc    960
ctgcgcgtga acaccgagat cacaaaggcc cccctgagcg cctccatgat caagagatat   1020
gacgagcacc accaggatct gaccctgctg aaggccctgg tgaggcagca gctgcctgag   1080
aagtacaagg atcttctt tgatcagagc aagaatggat acgcaggata tatcgacgga   1140
ggagcatccc aggaggagtt ctacaagttt atcaagccta tcctggagaa gatggacggc   1200
acagaggagc tgctggtgaa gctgaatcgg gaggacctgc tgaggaagca gcgcacccttt   1260 gataacggca gcatccctca ccagatccac ctgggagagc tgcacgcaat cctgcgccgg   1320
caggaggact tctacccatt tctgaaggat aaccgggaga gatcgagaa gatcctgaca   1380 ttcagaatcc cctactatgt gggacctctg gcccggggca atagcagatt tgcctggatg   1440
acccgcaagt ccgaggagac aatcacaccc tggaacttcg aggaggtggt ggataagggc   1500
gcctctgccc agagcttcat cgagcggatg accaattttg acaagaacct gcctaatgag   1560
aaggtgctgc caaagcactc tctgctgtac gagtatttca ccgtgtataa cgagctgaca   1620
aaggtgaagt acgtgaccga gggcatgaga aagcctgcct tcctgagcgg cgagcagaag   1680
aaggccatcg tggacctgct gtttaagacc aataggaagg tgacagtgaa gcagctgaag   1740
gaggactatt tcaagaagat cgagtgtttt gattctgtgg agatcagcgg cgtggaggac   1800
aggtttaacg cctccctggg cacctaccac gatctgctga gatcatcaa ggataaggac   1860 ttcctggaca cgaggagaa tgaggatatc ctggaggaca tcgtgctgac cctgacactg   1920
tttgaggata gggagatgat cgaggagcgc ctgaagacat atgcccacct gttcgatgac   1980
aaagtgatga agcagctgaa gagaaggcgc tacaccggat ggggccggct gagcagaaag   2040
ctgatcaatg gcatccgcga caagcagtct ggcaagacaa tcctggactt tctgaagagc   2100
gatggcttcg ccaaccggaa cttcatgcag ctgatccacg atgactccct gaccttcaag   2160
gaggatatcc agaaggcaca ggtgtctgga cagggcgaca gcctgcacga gcacatcgcc   2220
aacctggccg gctctcctgc catcaagaag ggcatcctgc agaccgtgaa ggtggtggac   2280
gagctggtga agtgatggg caggcacaag ccagagaaca tcgtgatcga gatggcccgc   2340
gagaatcaga ccacacagaa gggccagaag aactcccggg agagaatgaa gagaatcgag   2400
```

```
gagggcatca aggagctggg ctctcagatc ctgaaggagc accccgtgga gaacacacag    2460
ctgcagaatg agaagctgta tctgtactat ctgcagaatg ccgggatat gtacgtggac    2520
caggagctgg atatcaacag actgtctgat tatgacgtgg atcacatcgt gccacagtcc    2580
ttcctgaagg atgactctat cgacaataag gtgctgacca ggagcgacaa gaaccgcggc    2640
aagtccgata atgtgccctc tgaggaggtg gtgaagaaga tgaagaacta ctggaggcag    2700
ctgctgaatg ccaagctgat cacacagagg aagtttgata acctgaccaa ggcagagagg    2760
ggaggcctgt ccgagctgga caaggccggc ttcatcaagc ggcagctggt ggagacaaga    2820
cagatcacaa agcacgtggc ccagatcctg gattctagaa tgaacacaaa gtacgatgag    2880
aatgacaagc tgatcaggga ggtgaaagtg atcaccctga agtccaagct ggtgtctgac    2940
tttaggaagg atttccagtt ttataaggtg cgcgagatca caattatca ccacgcccac     3000
gacgcctacc tgaacgccgt ggtgggcaca gccctgatca gaagtaccc taagctggag    3060
tccgagttcg tgtacggcga ctataaggtg tacgatgtgc gcaagatgat cgccaagtct    3120
gagcaggaga tcggcaaggc caccgccaag tatttctttt acagcaacat catgaatttc    3180
tttaagaccg agatcacact ggccaatggc gagatcagga gcgcccact gatcgagaca    3240
aacggcgaga caggcgagat cgtgtgggac aagggcaggg attttgccac cgtgcgcaag    3300
gtgctgagca tgccccaagt gaatatcgtg aagaagaccg aggtgcagac aggcggcttc    3360
tccaaggagt ctatcctgcc taagcggaac tccgataagc tgatcgccag aaagaaggac    3420
tgggacccca agaagtatgg cggcttcgac agccctacag tggcctactc cgtgctggtg    3480
gtggccaagg tggagaaggg caagagcaag aagctgaagt ccgtgaagga gctgctgggc    3540
atcaccatca tggagcgcag ctccttcgag aagaatccta tcgattttct ggaggccaag    3600
ggctataagg aggtgaagaa ggacctgatc atcaagctgc caaagtactc tctgtttgag    3660
ctggagaacg gaaggaagag aatgctggca agcgccggag agctgcagaa gggcaatgag    3720
ctggcccctg cctccaagta cgtgaacttc ctgtatctgg cctcccacta cgagaagctg    3780
aagggctctc ctgaggataa cgagcagaag cagctgtttg tggagcagca caagcactat    3840
ctggacgaga tcatcgagca gatcagcgag ttctccaaga gagtgatcct ggccgacgcc    3900
aatctggata aggtgctgtc cgcctacaac aagcaccggg ataagccaat cagagagcag    3960
gccgagaata tcatccacct gtttacccgt acaaacctgg gagcaccagc agccttcaag    4020
tattttgaca ccacaatcga taggaagcgg tacaccagca caaaggaggt gctggacgcc    4080
acactgatcc accagtccat caccggcctg tacgagacac ggatcgacct gtctcagctg    4140
ggaggcgata agcggcccgc agcaaccaag aaggcaggac aggccaagaa gaagaaggaa    4200
ttcggcagca ccagcggcag cggcaagccc ggcagcggcg agggcagcac caagggcctc    4260
gagatgagta ctgcagatgc acttgatgat gaaaacacat taaaatatt agttgcaaca    4320
gatattcatc ttggatttat ggagaaagat gcagtcagag aaatgatac gtttgtaaca    4380
ctcgatgaaa ttttaagact tgcccaggaa aatgaagtgg attttatttt gttaggtggt    4440
gatcttttc atgaaaataa gccctcaagg aaaacattac atacctgcct cgagttatta    4500
agaaaatatt gtatgggtga tcggcctgtc cagtttgaaa ttctcagtga tcagtcagtc    4560
aactttggtt ttagtaagtt tccatgggtg aactatcaag atggcaacct caacatttca    4620
attccagtgt ttagtattca tggcaatcat gacgatccca caggggcaga tgcacttttgt    4680
gccttggaca tttaagttg tgctggattt gtaaatcact ttggacgttc aatgtctgtg    4740
gagaagatag acattagtcc ggttttgctt caaaaaggaa gcacaaagat tgcgctatat    4800
```

```
ggtttaggat ccattccaga tgaaaggctc tatcgaatgt ttgtcaataa aaaagtaaca    4860
atgttgagac caaaggaaga tgagaactct tggtttaact tatttgtgat tcatcagaac    4920
aggagtaaac atggaagtac taacttcatt ccagaacaat ttttggatga cttcattgat    4980
cttgttatct ggggccatga acatgagtgt aaaatagctc aaccaaaaa tgaacaacag     5040 ctgttttata tctcacaacc tggaagctca gtggttactt ctctttcccc aggagaagct    5100
gtaaagaaac atgttggttt gctgcgtatt aagggagga agatgaatat gcataaaatt    5160
cctcttcaca cagtgcggca gttttttcatg gaggatattg ttctagctaa tcatccagac   5220
atttttaacc cagataatcc taaagtaacc caagccatac aaagcttctg tttggagaag    5280
attgaagaaa tgcttgaaaa tgctgaacgg gaacgtctgg gtaattctca ccagccagag    5340
aagcctcttg tacgactgcg agtggactat agtggaggtt ttgaaccttt cagtgttctt    5400
cgctttagcc agaaatttgt ggatcgggta gctaatccaa aagacattat ccattttttc    5460
aggcatagag aacaaaagga aaaaacagga gaagagatca actttgggaa acttatcaca    5520
aagccttcag aaggaacaac tttaagggta gaagatcttg taaaacagta ctttcaaacc    5580
gcagagaaga atgtgcagct ctcactgcta acagaaagag ggatgggtga agcagtacaa    5640
gaatttgtgg acaaggagga gaaagatgcc attgaggaat tagtgaaata ccagttggaa    5700
aaaacacagc gatttcttaa agaacgtcat attgatgccc tcgaagacaa aatcgatgag    5760
gaggtacgtc gtttcagaga accagacaa aaaaatacta atgaagaaga tgatgaagtc     5820
cgtgaggcta tgaccagggc cagagcactc agatctcagt cagaggagtc tgcttctgcc    5880
tttagtgctg atgaccttat gagtatagat ttagcagaac agatggctaa tgactctgat    5940
gatagcatct cagcagcaac caacaaagga agaggccgag gaagaggtcg aagaggtgga    6000
agagggcaga attcagcatc gagaggaggg tctcaaagag gaagagcaga cactggtctg    6060
gagacttcta cccgtagcag gaactcaaag actgctgtgt cagcatctag aaatatgtct    6120
attatagatg cctttaaatc tacaagacag cagccttccc gaaatgtcac tactaagaat    6180
tattcagagg tgattgaggt agatgaatca gatgtggaag aagacatttt tcctaccact    6240
tcaaagacag atcaaaggtg gtccagcaca tcatccagca aaatcatgtc ccagagtcaa    6300
gtatcgaaag gggttgattt tgaatcaagt gaggatgatg atgatgatcc ttttatgaac    6360
actagttctt taagaagaaa tagaagaggg cccgttttaa                          6399
```

<210> SEQ ID NO 9
<211> LENGTH: 5289
<212> TYPE: DNA
<213> ORGANISM: Artificial Sequence
<220> FEATURE:
<223> OTHER INFORMATION: synthesized, RAD51-CAS9-HA

<400> SEQUENCE: 9

```
atggctatgc agatgcagct ggaggcaaac gcagatactt ccgtcgagga ggaatcattc      60
ggcccacagc ccatttcaag actggagcag tgcggcatca acgccaatga cgtgaagaag    120
ctggaggagg caggattcca caccgtggag gcagtggcat acgcacctaa gaaggagctg    180
atcaacatca agggcatctc cgaggccaag gccgataaga tcctggcaga ggcagcaaag    240
ctggtgccaa tgggcttcac cacagccaca gagtttcacc agcggagaag cgagatcatc    300
cagatcacca caggctccaa ggagctggat aagctgctgc agggcggcat cgagacaggc    360
tctatcacag agatgttcgg cgagtttcgc accggcaaga cacagatctg ccacacccctg   420
```

```
gccgtgacat gtcagctgcc aatcgacagg ggaggaggag agggcaaggc catgtatatc    480
gataccgagg gcacattcag gccagagcgc ctgctggcag tggcagagag atacggcctg    540
agcggctccg acgtgctgga taacgtggcc tatgccaggg cctttaatac cgaccaccag    600
acacagctgc tgtaccaggc ctctgccatg atggtggaga gcagatatgc actgctgatc    660
gtggacagcg ccaccgccct gtacaggaca gattattccg gcagaggcga gctgtctgcc    720
aggcagatgc acctggcccg gttcctgaga atgctgctgc ggctggccga tgagtttggc    780
gtggccgtgg tcatcaccaa ccaggtggtg gcacaggtgg acggagcagc aatgtttgca    840
gccgatccca agaagcctat cggcggcaat atcatcgccc acgcctctac acaaggctg     900 tacctgagga agggaagggg agagacacgg atctgcaaga tctatgacag cccctgtctg    960
ccagaggctg aagcaatgtt cgccatcaac gctgacgggg tgggagacgc caaggacgga   1020
tccggcagca ccagcggcag cggcaagccc ggcagcggcg agggcagcac caagggcgaa   1080
ttcgacaaga agtacagcat cggcctggat atcggcacaa actccgtggg ctgggccgtg   1140
atcaccgacg agtacaaggt gcccagcaag aagtttaagg tgctgggcaa caccgataga   1200
cactccatca agaagaatct gatcggcgcc ctgctgttcg actctggcga gacagcagag   1260
gcaacaaggc tgaagaggac cgcacggaga aggtatacac gccggaagaa taggatctgc   1320
tacctgcagg agatcttcag caacgagatg gccaaggtgg acgattcttt ctttcaccgc   1380
ctggaggaga gcttcctggt ggaggaggat aagaagcacg agcggcaccc tatctttggc   1440
aacatcgtgg acgaggtggc ctatcacgag aagtacccaa caatctatca cctgaggaag   1500
aagctggtgg actccaccga taaggccgac ctgcgcctga tctatctggc cctggcccac   1560
atgatcaagt tccggggcca ctttctgatc gagggcgatc tgaaccccga caatagcgat   1620
gtggacaagc tgttcatcca gctggtgcag acctacaatc agctgtttga ggagaaccct   1680
atcaatgcct ctggagtgga cgcaaaggca atcctgagcg ccaggctgtc caagtctaga   1740
aggctggaga acctgatcgc ccagctgccc ggcgagaaga gaacggcct gtttggcaat   1800 ctgatcgccc tgtccctggg cctgacacct aacttcaagt ctaatttga tctggccgag   1860 gacgccaagc tgcagctgtc caaggacacc tatgacgatg acctggataa cctgctggcc   1920
cagatcggcg atcagtacgc cgacctgttc ctggccgcca agaatctgtc tgacgccatc   1980
ctgctgagcg atatcctgcg cgtgaacacc gagatcacaa aggcccctct gagcgcctcc   2040
atgatcaaga gatatgacga gcaccaccag gatctgaccc tgctgaaggc cctggtgagg   2100
cagcagctgc cagagaagta caaggagatc ttctttgatc agagcaagaa tggatacgca   2160
ggatatatcg acggaggagc atcccaggag gagttctaca gtttatcaa gccaatcctg   2220 gagaagatgg acggcacaga ggagctgctg gtgaagctga atcgggagga cctgctgcgg   2280
aagcagagaa ccttgataa cggcagcatc ccacaccaga tccacctggg agagctgcac   2340
gcaatcctgc gccggcagga ggacttctac ccctttctga aggataaccg ggagaagatc   2400
gagaagatcc tgacattcag aatcccatac tatgtgggac cactggcccg ggcaatagc   2460 agatttgcct ggatgacccg caagtccgag gagacaatca cccctggaa cttcgaggag   2520 gtggtggata agggcgcctc tgcccagagc ttcatcgagc ggatgaccaa ttttgacaag   2580
aacctgccta atgagaaggt gctgccaaag cactctctgc tgtacgagta tttcaccgtg   2640
tataacgagc tgacaaaggt gaagtacgtg accgagggca tgagaaagcc tgccttcctg   2700
agcggcgagc agaagaaggc catcgtggac ctgctgttta agaccaatag gaaggtgaca   2760
gtgaagcagc tgaaggagga ctatttcaag aagatcgagt gttttgattc cgtggagatc   2820
```

```
tctggcgtgg aggaccgctt taacgcctcc ctgggcacct accacgatct gctgaagatc    2880
atcaaggata aggacttcct ggacaacgag gagaatgagg atatcctgga ggacatcgtg    2940
ctgaccctga cactgtttga ggataggag atgatcgagg agcgcctgaa gacatatgcc     3000
cacctgttcg atgacaaagt gatgaagcag ctgaagagaa ggcgctacac cggatggggc    3060
aggctgagcc gcaagctgat caatggcatc cgcgacaagc agtctggcaa gacaatcctg    3120
gactttctga gagcgatgg cttcgccaac cggaacttca tgcagctgat ccacgatgac    3180
tccctgacct tcaaggagga tatccagaag gcacaggtgt ctggacaggg cgacagcctg    3240
cacgagcaca tcgccaacct ggccggctct ccagccatca gaagggcat cctgcagacc     3300 gtgaaggtgg tggatgagct ggtgaaagtg atgggcaggc acaagcccga gaacatcgtg    3360
atcgagatgc ccgcgagaa tcagaccaca cagaagggcc agaagaactc ccgggagaga     3420
atgaagagaa tcgaggaggg catcaaggag ctgggctctc agatcctgaa ggagcaccct    3480
gtggagaaca cacagctgca gaatgagaag ctgtatctgt actatctgca gaatggccgg    3540
gatatgtacg tggaccagga gctggatatc aacagactgt ctgattatga cgtggatcac    3600
atcgtgcccc agtccttcct gaaggatgac tctatcgaca taaggtgct gaccaggagc     3660 gacaagaacc gcggcaagtc cgataatgtg ccttctgagg aggtggtgaa gagatgaag     3720 aactactgga ggcagctgct gaatgccaag ctgatcacac agaggaagtt tgataacctg    3780
accaaggcag agaggggagg cctgtccgag ctggacaagg ccggcttcat caagcggcag    3840
ctggtggaga caagacagat cacaaagcac gtggcccaga tcctggattc tagaatgaac    3900
acaaagtacg atgagaatga caagctgatc agggaggtga aagtgatcac cctgaagagc    3960
aagctggtgt ccgactttag gaaggatttc cagtttttata aggtgcgcga gatcaacaat    4020
tatcaccacg cccacgacgc ctacctgaac gccgtggtgg gcacagccct gatcaagaag    4080
taccctaagc tggagagcga gttcgtgtac ggcgactata aggtgtacga tgtgcggaag    4140
atgatcgcca agtctgagca ggagatcggc aaggccaccg ccaagtattt cttttacagc    4200
aacatcatga tttctttaa gaccgagatc acactggcca atggcgagat caggaagcgc    4260
ccactgatcg agacaaacgg cgagacaggc gagatcgtgt gggacaaggg cagggatttt    4320
gccaccgtgc gcaaggtgct gagcatgcct caagtgaata tcgtgaagaa gaccgaggtg    4380
cagacaggcg gcttctccaa ggagtctatc ctgccaaagc ggaactccga taagctgatc    4440
gccagaaaga aggactggga cccccaagaag tatggcggct cgacagccc cacagtggcc     4500 tactccgtgc tggtggtggc caaggtggag aagggcaaga gcaagaagct gaagtccgtg    4560
aaggagctgc tgggcatcac catcatggag cggagcagct tcgagaagaa cccaatcgat    4620
tttctggagg ccaagggcta taaggagtg aagaaggacc tgatcatcaa gctgcccaag      4680
tactctctgt ttgagctgga gaacggaagg aagagaatgc tggcaagcgc cggagagctg    4740
cagaagggca atgagctggc cctgccttcc aagtacgtga acttcctgta tctggcctcc    4800
cactacgaga agctgaaggg ctctccagag gataacgagc agaagcagct gtttgtggag    4860
cagcacaagc actatctgga cgagatcatc gagcagatca gcgagttctc caagagagtg    4920
atcctggccg acgccaatct ggataaggtg ctgtccgcct acaacaagca ccgggacaag    4980
cccatcagag agcaggccga gaatatcatc cacctgttca ccctgacaaa cctgggagca    5040
cctgcagcct tcaagtattt tgacaccaca atcgatagga agcggtacac cagcacaaag    5100
gaggtgctgg atgccacact gatccaccag tccatcaccg gcctgtacga gacacggatc    5160
```

```
gacctgtctc agctgggagg cgataagcgg cccgcagcaa ccaagaaggc aggacaggcc   5220
aagaagaaga aggacctgga gctcgagtct agagggccct acccatacga tgttccagat   5280
tacgcttga                                                           5289
```

```
<210> SEQ ID NO 10
<211> LENGTH: 1050
<212> TYPE: DNA
<213> ORGANISM: Artificial Sequence
<220> FEATURE:
<223> OTHER INFORMATION: synthesized, HA-RAD51

<400> SEQUENCE: 10
```

```
gccaccatgt acccatacga tgttccagat tacgctgcta tgcagatgca gctggaggca     60
aacgcagata cttccgtcga ggaggaatca ttcggcccac agcccatttc aagactggag    120
cagtgcggca tcaacgccaa tgacgtgaag aagctggagg aggcaggatt ccacaccgtg    180
gaggcagtgg catacgcacc taagaaggag ctgatcaaca tcaagggcat ctccgaggcc    240
aaggccgata agatcctggc agaggcagca agctggtgc caatgggctt caccacagcc    300
acagagtttc accagcggag aagcgagatc atccagatca ccacaggctc aaggagctg    360 gataagctgc tgcagggcgg catcgagaca ggctctatca gagatgtt cggcgagttt    420 cgcaccggca agacacagat ctgccacacc ctggccgtga catgtcagct gccaatcgac    480
aggggaggag gagagggcaa ggccatgtat atcgataccg agggcacatt caggccagag    540
cgcctgctgg cagtggcaga gagatacggc ctgagcggct ccgacgtgct ggataacgtg    600
gcctatgcca gggccttaa taccgaccac agacacagc tgctgtacca ggcctctgcc    660
atgatggtgg agagcagata tgcactgctg atcgtggaca cgccaccgc cctgtacagg    720 acagattatt ccggcagagg cgagctgtct gccaggcaga tgcacctggc ccggttcctg    780
agaatgctgc tgcggctggc cgatgagttt ggcgtggccg tggtcatcac caaccaggtg    840
gtggcacagg tggacggagc agcaatgttt gcagccgatc ccaagaagcc tatcggcggc    900
aatatcatcg cccacgcctc taccacaagg ctgtacctga ggaagggaag gggagagaca    960
cggatctgca agatctatga cagccccgt ctgccagagg ctgaagcaat gttcgccatc   1020
aacgctgacg gggtgggaga cgccaaggac                                   1050
```

```
<210> SEQ ID NO 11
<211> LENGTH: 5373
<212> TYPE: DNA
<213> ORGANISM: Artificial Sequence
<220> FEATURE:
<223> OTHER INFORMATION: synthesized, Rad51-Linker2-Cas9-HA

<400> SEQUENCE: 11
```

```
atggctatgc agatgcagct ggaggcaaac gcagatactt ccgtcgagga ggaatcattc     60
ggcccacagc ccatttcaag actggagcag tgcggcatca acgccaatga cgtgaagaag    120
ctggaggagg caggattcca caccgtggag gcagtggcat acgcacctaa gaaggagctg    180
atcaacatca gggcatctc cgaggccaag gccgataaga tcctggcaga ggcagcaaag    240
ctggtgccaa tgggcttcac cacagccaca gagtttcacc agcggagaag cgagatcatc    300
cagatcacca caggctccaa ggagctggat aagctgctgc agggcggcat cgagacaggc    360
tctatcacag atgttcgg cgagtttcgc accggcaaga cacagatctg ccacaccctg    420
gccgtgacat gtcagctgcc aatcgacagg ggaggaggag agggcaaggc catgtatatc    480
gataccgagg gcacattcag gccagagcgc ctgctggcag tggcagagag atacggcctg    540
```

```
agcggctccg acgtgctgga taacgtggcc tatgccaggg cctttaatac cgaccaccag    600
acacagctgc tgtaccaggc ctctgccatg atggtggaga gcagatatgc actgctgatc    660
gtggacagcg ccaccgccct gtacaggaca gattattccg gcagaggcga gctgtctgcc    720
aggcagatgc acctggcccg gttcctgaga atgctgctgc ggctggccga tgagtttggc    780
gtggccgtgg tcatcaccaa ccaggtggtg gcacaggtgg acggagcagc aatgtttgca    840
gccgatccca gaagcctat cggcggcaat atcatcgccc acgcctctac acaaggctg     900 tacctgagga agggaagggg agagacacgg atctgcaaga tctatgacag cccctgtctg    960
ccagaggctg aagcaatgtt cgccatcaac gctgacgggg tggagacgc caaggacgga   1020 tccgccgagg ccgcggcgaa agaagctgca gccaaggaag ccgccgctaa agaagctgcc   1080
gcgaaggcgc tcgaggcgga agctgctgca aaggaggcag ctgcgaaaga agcagcggca   1140
aaggaagccg cagcaaaagc tgaattcgac aagaagtaca gcatcggcct ggatatcggc   1200
acaaactccg tgggctgggc cgtgatcacc gacgagtaca aggtgcccag caagaagttt   1260
aaggtgctgg gcaacaccga tagacactcc atcaagaaga atctgatcgg cgccctgctg   1320
ttcgactctg gcgagacagc agaggcaaca aggctgaaga gaccgcacg gagaaggtat   1380 acacgccgga agaataggat ctgctacctg caggagatct tcagcaacga gatggccaag   1440
gtggacgatt ctttctttca ccgcctggag gagagcttcc tggtggagga ggataagaag   1500
cacgagcggc accctatctt tggcaacatc gtggacgagg tggcctatca cgagaagtac   1560
ccaacaatct atcacctgag gaagaagctg gtggactcca ccgataaggc cgacctgcgc   1620
ctgatctatc tggccctggc ccacatgatc aagttccggg gccactttct gatcgagggc   1680
gatctgaacc ccgacaatag cgatgtggac aagctgttca tccagctggt gcagacctac   1740
aatcagctgt ttgaggagaa ccctatcaat gcctctggag tggacgcaaa ggcaatcctg   1800
agcgccaggc tgtccaagtc tagaaggctg gagaacctga tcgcccagct gcccggcgag   1860
aagaagaacg gcctgtttgg caatctgatc gccctgtccc tgggcctgac acctaacttc   1920
aagtctaatt ttgatctggc cgaggacgcc aagctgcagc tgtccaagga cacctatgac   1980
gatgacctgg ataacctgct ggcccagatc ggcgatcagt acgccgacct gttcctggcc   2040
gccaagaatc tgtctgacgc catcctgctg agcgatatcc tgcgcgtgaa caccgagatc   2100
acaaaggccc tctgagcgc ctccatgatc aagagatatg acgagcacca ccaggatctg   2160
accctgctga aggccctggt gaggcagcag ctgccagaga agtacaagga gatcttcttt   2220
gatcagagca agaatggata cgcaggatat atcgacggag gagcatccca ggaggagttc   2280
tacaagttta tcaagccaat cctggagaag atggacggca cagaggagct gctggtgaag   2340
ctgaatcggg aggacctgct gcggaagcag agaacctttg ataacggcag catcccacac   2400
cagatccacc tgggagagct gcacgcaatc ctgcgccggc aggaggactt ctaccccttt   2460
ctgaaggata accgggagaa gatcgagaag atcctgacat tcagaatccc atactatgtg   2520
ggaccactgg cccggggcaa tagcagattt gcctggatga cccgcaagtc cgaggagaca   2580
atcacaccct ggaacttcga ggaggtggtg gataagggcg cctctgccca gagcttcatc   2640
gagcggatga ccaattttga caagaacctg cctaatgaga aggtgctgcc aaaagcactct   2700 ctgctgtacg agtatttcac cgtgtataac gagctgacaa aggtgaagta cgtgaccgag   2760
ggcatgagaa agcctgcctt cctgagcggc gagcagaaga aggccatcgt ggacctgctg   2820
tttaagacca ataggaaggt gacagtgaag cagctgaagg aggactattt caagaagatc   2880
```

```
gagtgttttg attccgtgga gatctctggc gtggaggacc gctttaacgc ctccctgggc    2940
acctaccacg atctgctgaa gatcatcaag gataaggact tcctggacaa cgaggagaat    3000
gaggatatcc tggaggacat cgtgctgacc ctgacactgt ttgaggatag ggagatgatc    3060
gaggagcgcc tgaagacata tgcccacctg ttcgatgaca agtgatgaa gcagctgaag     3120 agaaggcgct acaccggatg gggcaggctg agccgcaagc tgatcaatgg catccgcgac    3180
aagcagtctg gcaagacaat cctggacttt ctgaagagcg atggcttcgc caaccggaac    3240
ttcatgcagc tgatccacga tgactccctg accttcaagg aggatatcca gaaggcacag    3300
gtgtctggac agggcgacag cctgcacgag cacatcgcca acctggccgg ctctccagcc    3360
atcaagaagg gcatcctgca gaccgtgaag gtggtggatg agctggtgaa agtgatgggc    3420
aggcacaagc ccgagaacat cgtgatcgag atggcccgcg agaatcagac cacacagaag    3480
ggccagaaga actcccggga gagaatgaag agaatcgagg agggcatcaa ggagctgggc    3540
tctcagatcc tgaaggagca ccctgtggag aacacacagc tgcagaatga gaagctgtat    3600
ctgtactatc tgcagaatgg ccgggatatg tacgtggacc aggagctgga tatcaacaga    3660
ctgtctgatt atgacgtgga tcacatcgtg ccccagtcct tcctgaagga tgactctatc    3720
gacaataagg tgctgaccag gagcgacaag aaccgcggca gtccgataa tgtgccttct    3780 gaggaggtgg tgaagaagat gaagaactac tggaggcagc tgctgaatgc caagctgatc    3840
acacagagga agtttgataa cctgaccaag gcagagaggg gaggcctgtc cgagctggac    3900
aaggccggct tcatcaagcg gcagctggtg gagacaagac agatcacaaa gcacgtggcc    3960
cagatcctgg attctagaat gaacacaaag tacgatgaga tgacaagct gatcagggag     4020 gtgaaagtga tcaccctgaa gagcaagctg gtgtccgact ttaggaagga tttccagttt    4080
tataaggtgc gcgagatcaa caattatcac cacgcccacg acgcctacct gaacgccgtg    4140
gtgggcacag ccctgatcaa gaagtaccct aagctggaga gcgagttcgt gtacggcgac    4200
tataaggtgt acgatgtgcg gaagatgatc gccaagtctg agcaggagat cggcaaggcc    4260
accgccaagt atttcttta cagcaacatc atgaatttct ttaagaccga gatcacactg    4320
gccaatggcg agatcaggaa gcgcccactg atcgagacaa acggcgagac aggcgagatc    4380
gtgtgggaca agggcaggga ttttgccacc gtgcgcaagg tgctgagcat gcctcaagtg    4440
aatatcgtga agaagaccga ggtgcagaca ggcggcttct ccaaggagtc tatcctgcca    4500
aagcggaact ccgataagct gatcgccaga aagaaggact gggaccccaa gaagtatggc    4560
ggcttcgaca gccccacagt ggcctactcc gtgctggtgg tggccaaggt ggagaagggc    4620
aagagcaaga agctgaagtc cgtgaaggag ctgctgggca tcaccatcat ggagcggagc    4680
agcttcgaga agaacccaat cgattttctg gaggccaagg gctataagga ggtgaagaag    4740
gacctgatca tcaagctgcc caagtactct ctgtttgagc tggagaacgg aaggaagaga    4800
atgctggcaa gcgccggaga gctgcagaag ggcaatgagc tggccctgcc ttccaagtac    4860
gtgaacttcc tgtatctggc ctcccactac gagaagctga agggctctcc agaggataac    4920
gagcagaagc agctgtttgt ggagcagcac aagcactatc tggacgagat catcgagcag    4980
atcagcgagt tctccaagag agtgatcctg gccgacgcca atctggataa ggtgctgtcc    5040
gcctacaaca agcaccggga caagcccatc agagagcagg ccgagaatat catccacctg    5100 ttcacctga caaacctggg agcacctgca gccttcaagt attttgacac cacaatcgat    5160
aggaagcggt acaccagcac aaaggaggtg ctggatgcca cactgatcca ccagtccatc    5220
accggcctgt acgagacacg gatcgacctg tctcagctgg gaggcgataa gcggccgca    5280
```
gcaaccaaga aggcaggaca ggccaagaag aagaaggacc tggagctcga gtctagaggg    5340
ccctacccat acgatgttcc agattacgct tga                                 5373

<210> SEQ ID NO 12
<211> LENGTH: 5334
<212> TYPE: DNA
<213> ORGANISM: Artificial Sequence
<220> FEATURE:
<223> OTHER INFORMATION: synthesized, Rad51-Linker3-Cas9-HA

<400> SEQUENCE: 12

| | | | | | |
|---|---|---|---|---|---|
| atggctatgc | agatgcagct | ggaggcaaac | gcagatactt | ccgtcgagga | ggaatcattc | 60 |
| ggcccacagc | ccatttcaag | actggagcag | tgcggcatca | acgccaatga | cgtgaagaag | 120 |
| ctggaggagg | caggattcca | caccgtggag | gcagtggcat | acgcacctaa | gaaggagctg | 180 |
| atcaacatca | agggcatctc | cgaggccaag | gccgataaga | tcctggcaga | ggcagcaaag | 240 |
| ctggtgccaa | tgggcttcac | cacagccaca | gagtttcacc | agcggagaag | cgagatcatc | 300 |
| cagatcacca | caggctccaa | ggagctggat | aagctgctgc | agggcggcat | cgagacaggc | 360 |
| tctatcacag | agatgttcgg | cgagtttcgc | accggcaaga | cacagatctg | ccacaccctg | 420 |
| gccgtgacat | gtcagctgcc | aatcgacagg | ggaggaggag | agggcaaggc | catgtatatc | 480 |
| gataccgagg | gcacattcag | gccagagcgc | ctgctggcag | tggcagagag | atacggcctg | 540 |
| agcggctccg | acgtgctgga | taacgtggcc | tatgccaggg | cctttaatac | cgaccaccag | 600 |
| acacagctgc | tgtaccaggc | ctctgccatg | atggtggaga | gcagatatgc | actgctgatc | 660 |
| gtggacagcg | ccaccgccct | gtacaggaca | gattattccg | gcagaggcga | gctgtctgcc | 720 |
| aggcagatgc | acctggcccg | gttcctgaga | atgctgctgc | ggctggccga | tgagtttggc | 780 |
| gtggccgtgg | tcatcaccaa | ccaggtggtg | gcacaggtgg | acggagcagc | aatgtttgca | 840 |
| gccgatccca | gaagcctat | cggcggcaat | atcatcgccc | acgcctctac | acaaggctg | 900 |
| tacctgagga | agggaagggg | agagacacgg | atctgcaaga | tctatgacag | cccctgtctg | 960 |
| ccagaggctg | aagcaatgtt | cgccatcaac | gctgacgggg | tgggagacgc | caaggacgga | 1020 |
| tccggagccg | cgcctgcagc | cgctccagca | aaacaagaag | ctgcagcccc | ggcaccggcc | 1080 |
| gctaaagcag | aggcaccggc | tgcagctccc | gcggccaaag | cagaattcga | caagaagtac | 1140 |
| agcatcggcc | tggatatcgg | cacaaactcc | gtgggctggg | ccgtgatcac | cgacgagtac | 1200 |
| aaggtgccca | gcaagaagtt | taaggtgctg | ggcaacaccg | atagacactc | catcaagaag | 1260 |
| aatctgatcg | gcgccctgct | gttcgactct | ggcgagacag | cagaggcaac | aaggctgaag | 1320 |
| aggaccgcac | ggagaaggta | tacacgccgg | aagaatagga | tctgctacct | gcaggagatc | 1380 |
| ttcagcaacg | agatggccaa | ggtggacgat | tctttctttc | accgcctgga | ggagagcttc | 1440 |
| ctggtggagg | aggataagaa | gcacgagcgg | caccctatct | ttggcaacat | cgtggacgag | 1500 |
| gtggcctatc | acgagaagta | cccaacaatc | tatcacctga | ggaagaagct | ggtggactcc | 1560 |
| accgataagg | ccgacctgcg | cctgatctat | ctggccctgg | cccacatgat | caagttccgg | 1620 |
| ggccactttc | tgatcgaggg | cgatctgaac | cccgacaata | gcgatgtgga | caagctgttc | 1680 |
| atccagctgg | tgcagaccta | caatcagctg | tttgaggaga | cccctatcaa | tgcctctgga | 1740 |
| gtggacgcaa | aggcaatcct | gagcgccagg | ctgtccaagt | ctagaaggct | ggagaacctg | 1800 |
| atcgcccagc | tgcccggcga | gaagaagaac | ggcctgtttg | gcaatctgat | cgccctgtcc | 1860 |
| ctgggcctga | cacctaactt | caagtctaat | tttgatctgg | ccgaggacgc | caagctgcag | 1920 |

```
ctgtccaagg acacctatga cgatgacctg gataacctgc tggcccagat cggcgatcag    1980
tacgccgacc tgttcctggc cgccaagaat ctgtctgacg ccatcctgct gagcgatatc    2040
ctgcgcgtga acaccgagat cacaaaggcc cctctgagcg cctccatgat caagagatat    2100
gacgagcacc accaggatct gaccctgctg aaggccctgg tgaggcagca gctgccagag    2160
aagtacaagg agatcttctt tgatcagagc aagaatggat acgcaggata tatcgacgga    2220
ggagcatccc aggaggagtt ctacaagttt atcaagccaa tcctggagaa gatggacggc    2280
acagaggagc tgctggtgaa gctgaatcgg gaggacctgc tgcggaagca gagaaccttt    2340
gataacggca gcatcccaca ccagatccac ctgggagagc tgcacgcaat cctgcgccgg    2400
caggaggact tctaccccctt tctgaaggat aaccgggaga gatcgagaa gatcctgaca    2460 ttcagaatcc catactatgt gggaccactg gccggggca atagcagatt tgcctggatg    2520
acccgcaagt ccgaggagac aatcacaccc tggaacttcg aggaggtggt ggataagggc    2580
gcctctgccc agagcttcat cgagcggatg accaattttg acaagaacct gcctaatgag    2640
aaggtgctgc caaagcactc tctgctgtac gagtatttca ccgtgtataa cgagctgaca    2700
aaggtgaagt acgtgaccga gggcatgaga aagcctgcct tcctgagcgg cgagcagaag    2760
aaggccatcg tggacctgct gtttaagacc aataggaagg tgacagtgaa gcagctgaag    2820
gaggactatt tcaagaagat cgagtgtttt gattccgtgg agatctctgg cgtggaggac    2880
cgctttaacg cctcccctggg cacctaccac gatctgctga gatcatcaa ggataaggac    2940 ttcctggaca cgaggagaa tgaggatatc ctggaggaca tcgtgctgac cctgacactg    3000
tttgaggata gggagatgat cgaggagcgc ctgaagacat atgcccacct gttcgatgac    3060
aaagtgatga agcagctgaa gagaaggcgc tacaccggat ggggcaggct gagccgcaag    3120
ctgatcaatg gcatccgcga caagcagtct ggcaagacaa tcctggactt tctgaagagc    3180
gatggcttcg ccaaccggaa cttcatgcag ctgatccacg atgactccct gaccttcaag    3240
gaggatatcc agaaggcaca ggtgtctgga cagggcgaca gcctgcacga gcacatcgcc    3300
aacctggccg gctctccagc catcaagaag ggcatcctgc agaccgtgaa ggtggtggat    3360
gagctggtga agtgatgggg caggcacaag cccgagaaca tcgtgatcga gatggcccgc    3420
gagaatcaga ccacacagaa gggccagaag aactcccggg agagaatgaa gagaatcgag    3480
gagggcatca aggagctggg ctctcagatc ctgaaggagc accctgtgga aacacacag    3540 ctgcagaatg agaagctgta tctgtactat ctgcagaatg gccgggatat gtacgtggac    3600
caggagctgg atatcaacag actgtctgat tatgacgtgg atcacatcgt gccccagtcc    3660
ttcctgaagg atgactctat cgacaataag gtgctgacca ggagcgacaa gaaccgcggc    3720
aagtccgata tgtgccttc tgaggaggtg gtgaagaaga tgaagaacta ctggaggcag    3780
ctgctgaatg ccaagctgat cacacagagg aagtttgata acctgaccaa ggcagagagg    3840
ggaggcctgt ccgagctgga caaggccggc ttcatcaagc ggcagctggt ggagacaaga    3900
cagatcacaa agcacgtggc ccagatcctg gattctagaa tgaacacaaa gtacgatgag    3960
aatgacaagc tgatcaggga ggtgaaagtg atcacccctga agagcaagct ggtgtccgac    4020
tttaggaagg atttccagtt ttataaggtg cgcgagatca caattatca ccacgccac    4080 gacgcctacc tgaacgccgt ggtgggcaca gccctgatca agaagtaccc taagctggag    4140
agcgagttcg tgtacggcga ctataaggtg tacgatgtgc ggaagatgat cgccaagtct    4200
gagcaggaga tcgcaaggc caccgccaag tatttcttt acagcaacat catgaatttc    4260
tttaagaccg agatcacact ggccaatggc gagatcagga gcgcccact gatcgagaca    4320
```

```
aacggcgaga caggcgagat cgtgtgggac aagggcaggg attttgccac cgtgcgcaag    4380
gtgctgagca tgcctcaagt gaatatcgtg aagaagaccg aggtgcagac aggcggcttc    4440
tccaaggagt ctatcctgcc aaagcggaac tccgataagc tgatcgccag aaagaaggac    4500
tgggacccca agaagtatgg cggcttcgac agccccacag tggcctactc cgtgctggtg    4560
gtggccaagg tggagaaggg caagagcaag aagctgaagt ccgtgaagga gctgctgggc    4620
atcaccatca tggagcggag cagcttcgag aagaacccaa tcgattttct ggaggccaag    4680
ggctataagg aggtgaagaa ggacctgatc atcaagctgc caagtactc tctgtttgag    4740 ctggagaacg gaaggaagag aatgctggca agcgccggag agctgcagaa gggcaatgag    4800
ctggccctgc cttccaagta cgtgaacttc ctgtatctgg cctcccacta cgagaagctg    4860
aagggctctc cagaggataa cgagcagaag cagctgtttg tggagcagca caagcactat    4920
ctggacgaga tcatcgagca gatcagcgag ttctccaaga gagtgatcct ggccgacgcc    4980
aatctggata aggtgctgtc cgcctacaac aagcaccggg acaagcccat cagagagcag    5040
gccgagaata tcatccacct gttcacgctg acaaacctgg agcacctgc agccttcaag    5100 tattttgaca ccacaatcga taggaagcgg tacaccagca caaaggaggt gctggatgcc    5160
acactgatcc accagtccat caccggcctg tacgagacac ggatcgacct gtctcagctg    5220
ggaggcgata gcggcccgc agcaaccaag aaggcaggac aggccaagaa gaagaaggac    5280
ctggagctcg agtctagagg gccctaccca tacgatgttc cagattacgc ttga          5334
```

<210> SEQ ID NO 13
<211> LENGTH: 5313
<212> TYPE: DNA
<213> ORGANISM: Artificial Sequence
<220> FEATURE:
<223> OTHER INFORMATION: synthesized, HA-Cas9-P2A-Rad51

<400> SEQUENCE: 13

```
gccaccatgt acccatacga tgttccagat tacgctggta ccgagctcgg atccgacaag     60
aagtatagca tcggcctgga tatcggcaca aactccgtgg ctgggccgt gatcaccgac    120 gagtacaagg tgccaagcaa gaagtttaag gtgctgggca caccgatag acactccatc    180 aagaagaatc tgatcggcgc cctgctgttc gactctggcg agacagccga ggccacacgg    240
ctgaagagaa ccgcccggag aaggtataca cgccggaaga ataggatctg ctacctgcag    300
gagatcttca gcaacgagat ggccaaggtg gacgattctt tctttcaccg cctggaggag    360
agcttcctgg tggaggagga taagaagcac gagcggcacc ctatctttgg caacatcgtg    420
gacgaggtgg cctatcacga gaagtaccca acaatctatc acctgaggaa gaagctggtg    480
gactccaccg ataaggccga cctgcgcctg atctatctgg ccctggccca catgatcaag    540
ttccggggcc actttctgat cgagggcgat ctgaacccag acaatagcga tgtggacaag    600
ctgttcatcc agctggtgca gacctacaat cagctgtttg aggagaaccc catcaatgcc    660
tctggagtgg acgcaaaggc aatcctgagc gccagactgt ccaagtctag aaggctggag    720
aacctgatcg cccagctgcc aggcgagaag aagaacggcc tgtttggcaa tctgatcgcc    780
ctgtccctgg gcctgacacc caacttcaag tctaattttg atctggccga ggacgccaag    840
ctgcagctgt ccaaggacac ctatgacgat gacctggata acctgctggc ccagatcggc    900
gatcagtacg ccgacctgtt cctggccgcc aagaatctgt ctgacgccat cctgctgagc    960
gatatcctgc gcgtgaacac cgagatcaca aaggccccc tgagcgcctc catgatcaag   1020
```

```
agatatgacg agcaccacca ggatctgacc ctgctgaagg ccctggtgag gcagcagctg    1080
cctgagaagt acaaggagat cttctttgat cagagcaaga atggatacgc aggatatatc    1140
gacggaggag catcccagga ggagttctac aagtttatca agcctatcct ggagaagatg    1200
gacggcacag aggagctgct ggtgaagctg aatcgggagg acctgctgag gaagcagcgc    1260
acctttgata cggcagcat ccctcaccag atccacctgg gagagctgca cgcaatcctg    1320
cgccggcagg aggacttcta cccatttctg aaggataacc gggagaagat cgagaagatc    1380
ctgacattca gaatccccta ctatgtggga cctctggccc ggggcaatag cagatttgcc    1440
tggatgaccc gcaagtccga ggagacaatc acaccctgga acttcgagga ggtggtggat    1500
aagggcgcct ctgcccagag cttcatcgag cggatgacca attttgacaa gaacctgcct    1560
aatgagaagg tgctgccaaa gcactctctg ctgtacgagt atttcaccgt gtataacgag    1620
ctgacaaagg tgaagtacgt gaccgagggc atgagaaagc ctgccttcct gagcggcgag    1680
cagaagaagg ccatcgtgga cctgctgttt aagaccaata ggaaggtgac agtgaagcag    1740
ctgaaggagg actatttcaa gaagatcgag tgttttgatt ctgtggagat cagcggcgtg    1800
gaggacaggt ttaacgcctc cctgggcacc taccacgatc tgctgaagat catcaaggat    1860
aaggacttcc tggacaacga ggagaatgag gatatcctgg aggacatcgt gctgaccctg    1920
acactgtttg aggatagga gatgatcgag gagcgcctga agacatatgc ccacctgttc    1980
gatgacaaag tgatgaagca gctgaagaga aggcgctaca ccggatgggg ccggctgagc    2040
agaaagctga tcaatggcat ccgcgacaag cagtctggca agacaatcct ggactttctg    2100
aagagcgatg gcttcgccaa ccggaacttc atgcagctga tccacgatga ctccctgacc    2160
ttcaaggagg atatccagaa ggcacaggtg tctggacagg cgacagcct gcacgagcac    2220 atcgccaacc tggccggctc tcctgccatc aagaagggca tcctgcagac cgtgaaggtg    2280
gtggacgagc tggtgaaagt gatgggcagg cacaagccag agaacatcgt gatcgagatg    2340
gcccgcgaga tcagaccac acagaagggc cagaagaact cccgggagag aatgaagaga    2400
atcgaggagg gcatcaagga gctgggctct cagatcctga aggagcaccc cgtggagaac    2460
acacagctgc agaatgagaa gctgtatctg tactatctgc agaatggccg ggatatgtac    2520
gtggaccagg agctggatat caacagactg tctgattatg acgtggatca catcgtgcca    2580
cagtccttcc tgaaggatga ctctatcgac aataaggtgc tgaccaggag cgacaagaac    2640
cgcggcaagt ccgataatgt gccctctgag gaggtggtga agaagatgaa gaactactgg    2700
aggcagctgc tgaatgccaa gctgatcaca cagaggaagt tgataaacct gaccaaggca    2760
gagaggggag gcctgtccga gctggacaag gccggcttca tcaagcggca gctggtggag    2820
acaagacaga tcacaaagca cgtggcccag atcctggatt ctagaatgaa cacaaagtac    2880
gatgagaatg acaagctgat cagggaggtg aaagtgatca ccctgaagtc caagctggtg    2940
tctgacttta aggaaggatt ccagttttat aaggtgcgcg agatcaacaa ttatcaccac    3000
gcccacgacg cctacctgaa cgccgtggtg ggcacagccc tgatcaagaa gtaccctaag    3060
ctggagtccg agttcgtgta cggcgactat aaggtgtacg atgtgcgcaa gatgatcgcc    3120
aagtctgagc aggagatcgg caaggccacc gccaagtatt tctttacag caacatcatg    3180 aatttctttaagaccgagat cacactggcc aatggcgaga tcaggaagcg cccactgatc    3240
gagacaaacg gcgagacagg cgagatcgtg tgggacaagg cagggatttt gccaccgtg    3300 cgcaaggtgc tgagcatgcc ccaagtgaat atcgtgaaga gaccgaggt gcagacaggc    3360 ggcttctcca aggagtctat cctgcctaag cggaactccg ataagctgat cgccagaaag    3420
```

```
aaggactggg accccaagaa gtatggcggc ttcgacagcc ctacagtggc ctactccgtg    3480
ctggtggtgg ccaaggtgga agggcaag agcaagaag tgaagtccgt gaaggagctg      3540
ctgggcatca ccatcatgga gcgcagctcc ttcgagaaga atcctatcga ttttctggag   3600
gccaagggct ataaggaggt gaagaaggac ctgatcatca agctgccaaa gtactctctg   3660
tttgagctgg agaacggaag gaagagaatg ctggcaagcg ccggagagct gcagaagggc   3720
aatgagctgc ccctgccctc caagtacgtg aacttcctgt atctggcctc ccactacgag   3780
aagctgaagg gctctcctga ggataacgag cagaagcagc tgtttgtgga gcagcacaag   3840
cactatctgg acgagatcat cgagcagatc agcgagttct ccaagagagt gatcctggcc   3900
gacgccaatc tggataaggt gctgtccgcc tacaacaagc accgggataa gccaatcaga   3960
gagcaggccg agaatatcat ccacctgttt accctgacaa acctgggagc cagcagcc    4020 ttcaagtatt ttgacaccac aatcgatagg aagcggtaca ccagcacaaa ggaggtgctg   4080
gacgccacac tgatccacca gtccatcacc ggcctgtacg agacacggat cgacctgtct   4140
cagctgggag gcgataagcg gccccgcagca accaagaagg caggacaggc caagaagaag  4200
aaggaattcg gcggcagcgg cgccaccaac ttcagcctgc tgaagcaggc cggcgacgtg   4260
gaggagaacc ccggcccct cgagatggct atgcagatgc agctggaggc aaacgcagat    4320
acttccgtcg aggaggaatc attcggccca cagcccattt caagactgga gcagtgcggc   4380
atcaacgcca atgacgtgaa gaagctggag gaggcaggat tccacaccgt ggaggcagtg   4440
gcatacgcac ctaagaagga gctgatcaac atcaagggca tctccgaggc caaggccgat   4500
aagatcctgg cagaggcagc aaagctggtg ccaatgggct tcaccacagc cacagagttt  4560
caccagcgga aagcgagat catccagatc accacaggct ccaaggagct ggataagctg   4620
ctgcagggcg gcatcgagac aggctctatc acagagatgt tcggcgagtt tcgcaccggc   4680
aagacacaga tctgccacac cctggccgtg acatgtcagc tgccaatcga caggggagga  4740
ggagagggca aggccatgta tatcgatacc gagggcacat tcaggccaga gcgcctgctg   4800
gcagtggcag agagatacgg cctgagcggc tccgacgtgc tggataacgt ggcctatgcc   4860 agggcctta taccgacca ccagacacag ctgctgtacc aggcctctgc catgatggtg     4920
gagagcagat atgcactgct gatcgtggac agcgccaccg ccctgtacag gacagattat   4980
tccggcagag gcgagctgtc tgccaggcag atgcacctgg cccggttcct gagaatgctg   5040
ctgcggctgg ccgatgagtt tggcgtggcc gtggtcatca ccaaccaggt ggtggcacag   5100
gtggacggag cagcaatgtt tgcagccgat cccaagaagc ctatcggcgg caatatcatc   5160
gcccacgcct ctaccacaag gctgtacctg aggaagggaa ggggagagac acggatctgc   5220
aagatctatg acagccctg tctgccagag gctgaagcaa tgttcgccat caacgctgac   5280
ggggtgggag acgccaagga cgggcccgtt taa                                5313
```

<210> SEQ ID NO 14
<211> LENGTH: 18
<212> TYPE: PRT
<213> ORGANISM: Artificial Sequence
<220> FEATURE:
<223> OTHER INFORMATION: synthesized, Linker 1

<400> SEQUENCE: 14

Gly Ser Thr Ser Gly Ser Gly Lys Pro Gly Ser Gly Glu Gly Ser Thr
1               5                   10                  15

Lys Gly

```
<210> SEQ ID NO 15
<211> LENGTH: 46
<212> TYPE: PRT
<213> ORGANISM: Artificial Sequence
<220> FEATURE:
<223> OTHER INFORMATION: synthesized, Linker 2_Rigid_helix

<400> SEQUENCE: 15

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Ala Lys Glu Ala
                20                  25                  30

Ala Ala Lys Glu Ala Ala Ala Lys Glu Ala Ala Ala Lys Ala
            35                  40                  45

<210> SEQ ID NO 16
<211> LENGTH: 33
<212> TYPE: PRT
<213> ORGANISM: Artificial Sequence
<220> FEATURE:
<223> OTHER INFORMATION: synthesized, Linker 3

<400> SEQUENCE: 16

Gly Ala Ala Pro Ala Ala Ala Pro Ala Lys Gln Glu Ala Ala Ala Pro
1               5                   10                  15

Ala Pro Ala Ala Lys Ala Glu Ala Pro Ala Ala Ala Pro Ala Ala Lys
                20                  25                  30

Ala
```

COMPOSITIONS AND METHODS FOR PROMOTING HOMOLOGY DIRECTED REPAIR MEDIATED GENE EDITING

CROSS-REFERENCE TO RELATED APPLICATIONS

This application is a § 371 national stage of PCT International Application No. PCT/US2017/017932, filed Feb. 15, 2017, claiming the benefit of U.S. Provisional Applications No. 62/410,627, filed Oct. 20, 2016; 62/397,288, filed Sep. 20, 2016; 62/295,518, filed Feb. 16, 2016; and 62/295,517, filed Feb. 16, 2016, the contents of each of which are hereby incorporated by reference into the application.

This application claims priority of U.S. Provisional Application Nos. 62/410,627, filed Oct. 20, 2016; 62/397,288, filed Sep. 20, 2016; 62/295,518, filed Feb. 16, 2016; and 62/295,517, filed Feb. 16, 2016, the contents of each of which are hereby incorporated by reference.

Throughout this application, various publications are referenced, including referenced in parenthesis. Full citations for publications referenced in parenthesis may be found listed at the end of the specification immediately preceding the claims. The disclosures of all referenced publications in their entireties are hereby incorporated by reference into this application in order to more fully describe the state of the art to which this invention pertains.

This application incorporates-by-reference nucleotide and/or amino acid sequences which are present in the file named "170215_6317_88438_A_PCT_Sequence_Listing_AWG.txt", which is 55.0 kilobytes in size, and which was created Feb. 15, 2017 in the IBM-PC machine format, having an operating system compatibility with MS-Windows, which is contained in the text file filed Feb. 15, 2017 as part of this application.

The present invention relates to compositions and methods for increasing the rate of nuclease-mediated site specific insertions of donor DNA sequence to the genome via recombination. More specifically, the method utilizes a non-naturally occurring nuclease-homology directed repair (HDR) protein chimeras for genome editing applications. Physically tethering the activity of a DNA nuclease to an HDR protein results in a significant increase in the fraction of nuclease induced DNA breaks that are repaired by homologous recombination and provides higher accuracy and specificity of genome editing.

BACKGROUND

Targeted genome modification is a powerful tool that can be used to reverse the effect of pathogenic genetic variations and therefore has the potential to provide new therapies for human genetic diseases. Current genome engineering tools, including engineered zinc finger nucleases (ZFNs), transcription activator-like effector nucleases (TALENs), and most recently, the RNA-guided DNA nucleases such as CRISPR/Cas, produce sequence-specific DNA breaks in a genome. The modification of the genomic sequence occurs at the next step and is the product of the activity of one of two cellular DNA repair mechanisms triggered in response to the newly formed DNA break. These mechanisms include: (1) non-homologous end joining (NHEJ) in which the two ends of the break are ligated together in a fast but inaccurate manner (i.e. frequently resulting in mutation of the DNA at the cleavage site in the form of small insertion or deletions) and (2) homology-directed repair (HDR) in which an intact homologous DNA donor is used to replace the DNA surrounding the cleavage site in an accurate manner. In addition, HDR can also mediate the precise insertion of external DNA at the break site.

A major drawback of current genome engineering tools is the lack of ability to control the division of labor between the cellular DNA repair mechanisms. As a result, the DNA breaks that are generated using these tools are repaired stochastically by either NHEJ or HDR. This stochastic nature of repair frequently leads to a futile outcome that significantly reduces the efficiency and accuracy of the process. For example, reversing the pathogenic effect of disease-causing genetic variations requires, in many cases, the insertion of a DNA element from an external source at the break site. This activity is mediated by HDR. However, using the currently available genome editing tools, the majority of breaks will be subjected to repair via NHEJ, which is the dominant process. In such cases, NHEJ not only outcompetes HDR on repairing the initial DNA breaks, but is also likely to result in mutation of the original sequence.

SUMMARY OF THE INVENTION

The present disclosure provides compositions and methods for increasing the efficiency and reducing the off-target effect of a nuclease (e.g., Cpf1, Cas9, ZFN, Meganucleases, TALENs, etc.) induced genome editing. The composition is a fusion protein, which contains a nuclease, or a functional domain thereof, fused to an HDR protein (HDRP), or a functional domain thereof. Introduction of the nuclease-HDRP fusion to cells along with a specific DNA donor and, if appropriate, a specific guide RNA (gRNA), results in elevated rates of repair, of the nuclease induced DNA breaks by HDR and insertion of the desired DNA sequence at the correct genomic locus.

In one embodiment, the present invention is a fusion protein, said fusion protein comprising a DNA binding DNA nuclease or a functional fragment thereof operably linked to an HDR protein or a functional fragment thereof.

In some embodiments, the DNA binding DNA nuclease is selected from the group consisting of Cas9, Cpf1, ZFP, TALEN and Meganuclease.

In some embodiments, the present invention is a method for genome editing in a cell comprising introducing to said cell:
 a. a composition comprising a fusion protein described herein;
 b. a gRNA molecule;
 c. a donor;
wherein said composition and gRNA bind a target sequence, and wherein said donor is inserted to said target sequence.

In some embodiments, the present invention is a method for genome editing in a cell comprising introducing to said cell:
 a. a composition comprising a fusion protein described herein;
 b. a donor;
wherein, said donor is inserted to said target sequence.

In some embodiments, the present invention is a method for genome editing in a cell comprising introducing to said cell:
 a. a composition comprising a fusion protein described herein;
 b. a gRNA molecule;
 c. a donor;

wherein, said composition and gRNA bind a target sequence; and wherein, said donor is copied to said target sequence.

In some embodiments, the present invention is a method for genome editing in a cell comprising introducing to a cell one or more vectors, said one or more vectors comprising:
a. a first nucleotide sequence encoding a composition comprising a fusion protein described herein;
b. a second nucleotide sequence encoding a gRNA molecule;
c. a third nucleotide sequence;
wherein said third nucleotide sequence is a recombination donor;
wherein, said nucleotide sequences are transcribed and translated in said cell; wherein, said composition and gRNA bind a target sequence; and wherein, said donor is inserted to said target sequence.

In some embodiments, the present invention is a method for genome editing in a cell comprising introducing to a cell one or more vectors, said one or more vectors comprising:
a. a first nucleotide sequence encoding said a composition comprising a fusion protein described herein;
b. a second nucleotide sequence;
wherein said second nucleotide sequence is a recombination donor;
wherein, said nucleotide sequences are transcribed and translated in said cell;
wherein, said composition is capable of binding a target sequence; and wherein, said donor is inserted or copied to said target sequence.

In some embodiments, the present invention is a method for genome editing in a cell comprising introducing to a cell the composition comprising a fusion protein described herein and a donor, wherein said composition is capable of binding a target sequence, and wherein said donor is inserted or copied to said target sequence.

In some embodiments, the HDR protein or functional fragment thereof is fused to the N-terminal of a DNA binding DNA nuclease. In other embodiments, the HDR protein or functional fragment thereof is fused to the C-terminal of a DNA binding DNA nuclease. In some embodiments, a linker connects the HDR protein portion of the fusion protein to the DNA binding DNA nuclease portion of the protein. Thus, the DNA binding DNA nuclease may be upstream or downstream of the HDR protein relative to the linker.

In some embodiments, more than one HDR protein or functional fragment thereof is fused to a DNA binding DNA nuclease at any position.

In some embodiments, the nuclease is derived from any available natural source.

In other embodiments, the nuclease is an engineered protein or a synthetic protein.

In some embodiments, the nuclease is selected from the list comprising zinc finger nucleases (ZFNs), TALENs (including TALENs comprising Fok1-TALE DNA binding domain fusions, Mega TALs and compact TALENs), meganucleases and nucleases derived from CRISPR systems.

In some embodiments, the method of genome editing results in at least 10% increase in the rate of targeted insertion events in a cell population as compared to the targeted insertion rate in a similar cell population subjected to genome editing using only the DNA binding DNA nuclease or a functional fragment thereof.

In some embodiments, the method of genome editing results in at least 50% increase in the rate of targeted insertion events in a cell population as compared to the targeted insertion rate in a similar cell population subjected to genome editing using only the DNA binding DNA nuclease or a functional fragment thereof.

In some embodiments, the method of genome editing results in an at least 10%, at least 20%, at least 30%, at least 40%, at least 50%, at least 60%, at least 70%, at least 80%, at least 90%, or at least 100% increase in the rate of targeted insertion events in a cell population as compared to the targeted insertion rate in a similar cell population subjected to genome editing using only the DNA binding DNA nuclease or a functional fragment thereof.

In some embodiments, the method of genome editing results in a more than 10%, more than 20%, more than 30%, more than 40%, more than 50%, more than 60%, more than 70%, more than 80%, more than 90%, or more than 100% increase in the rate of targeted insertion events in a cell population as compared to the targeted insertion rate in a similar cell population subjected to genome editing using only the DNA binding DNA nuclease or a functional fragment thereof.

In some embodiments the method of genome editing results in at least 10% reduction of off-target excision of the genome as compared to the insertion rate using a similar nuclease alone.

In some embodiments, the method of genome editing results in at least 50% reduction of off-target excision of the genome as compared to the insertion rate using a similar nuclease alone.

In some embodiments, the method of genome editing in at least 100% reduction of off-target excision of the genome as compared to the insertion rate using a similar nuclease alone.

The present invention provides a composition comprising a fusion protein, the fusion protein comprising:
a. a DNA binding DNA nuclease or a functional fragment thereof; and
b. a homology directed repair (HDR) protein or a functional fragment thereof.

In some embodiments, wherein said DNA binding DNA nuclease is selected from the group consisting of: ZFN, TALEN and Meganuclease.

In some embodiments, the DNA binding DNA nuclease is a RNA-guided DNA nuclease.

In some embodiments, the RNA-guided DNA nuclease is selected from the group consisting of: Cas9, Cpf1, and homologues thereof.

In some embodiments, the DNA binding DNA nuclease is a modified or altered DNA binding DNA nuclease.

In some embodiments, the DNA binding DNA nuclease is a nickase.

In some embodiments, wherein said HDR protein is selected from the group consisting of: Rad50, Rad51, Rad54, BRCA1, BRCA2, Mre11, Nbs1, CtIP, PALB2, SHFM1 and Exd2.

In some embodiments, further comprising a linker, wherein said linker is attached to said DNA binding DNA nuclease and to said HDRP.

In some embodiments, wherein said linker is a polypeptide attached by polypeptide bonds to said nuclease and to said HDRP. Any polypeptide linker known in the art is contemplated as a potential linker in a nuclease-HDRP fusion protein of the present invention. The linker may be rigid or flexible. The linker may have a length of 1, 2, 3, 4, 5, 10, 15, 20, 30, 40, 50, 60, 70, 80, 90, 100, 200, 500 amino acids or more. The linker may range in length from 1-10, 1-50, 1-100, 10-50, 10-100, 25-50, 30-50 amino acids.

In some embodiments, wherein said linker has a protein sequence selected from the group consisting of SEQ ID NO: 14, SEQ ID NO: 15 and SEQ ID NO: 16.

In some embodiments, wherein the DNA binding DNA nuclease is upstream of the HDR protein.

In some embodiments, wherein the DNA binding DNA nuclease is downstream of the HDR protein.

The present invention provides for a polynucleotide encoding the composition of any one of the fusion proteins described herein.

In some embodiments, the polynucleotide is DNA.

In some embodiments, the polynucleotide is RNA.

In some embodiments, the polynucleotide is modified. Modifications to polynucleotides include 3'-polyadenylation or 5'-capping of mRNAs. Modifications to polynucleotides may be synthetic and encompass polynucleotides which contain nucleotides comprising bases other than the naturally occurring adenine, cytosine, thymine, uracil, or guanine bases. Modifications to polynucleotides include polynucleotides which contain synthetic, non-naturally occurring nucleosides e.g., locked nucleic acids. An example of a modified polynucleotide is an mRNA containing 1-methyl pseudo-uridine.

In some embodiments, the polynucleotide is a modified polynucleotide.

In some embodiments, the modified polynucleotide contains a 1-methyl pseudo-uridine.

The present invention also provides a method for genome editing comprising introducing to a cell the fusion protein described herein, or a polynucleotide encoding the fusion protein as described herein, so as to induce genome editing.

In some embodiments, the method further comprises introducing to the cell an exogenous donor DNA.

In some embodiments, the exogenous donor DNA is single-stranded DNA. In some embodiments, the exogenous donor DNA may be double-stranded DNA. In some embodiments, the exogenous donor DNA may be linear or circular.

In some embodiments, the genome editing results in an at least 10%, more preferably at least 40%, more preferably at least 50%, more preferably at least 100% increase in the rate of DNA insertion compared to the DNA-binding DNA nuclease alone.

In some embodiments, wherein the genome editing results in an at least 10%, more preferably at least 40%, more preferably at least 50%, more preferably at least 100% reduction in off-target excision compared to the DNA-binding DNA nuclease alone.

The present invention also provides a method for increasing the rate of homology directed recombination at a target site in the genome of a cell, the method comprising delivering to the cell the fusion protein described herein, or a polynucleotide encoding the fusion protein as described herein, wherein the rate of homology directed recombination at the target site in the cell is compared to the rate of homology directed recombination at the target site in a cell expressing the DNA-binding DNA alone.

In some embodiments, the method further comprises delivering to the cell an exogenous donor DNA which is inserted at the target site in the genome of the cell.

In some embodiments, the exogenous donor DNA is single-stranded DNA. In some embodiments, the exogenous donor DNA may be double-stranded DNA. In some embodiments, the exogenous donor DNA may be linear or circular.

In some embodiments, the rate of homology directed recombination is increased by at least 10%, more preferably at least 40%, more preferably at least 50%, more preferably at least 100% compared to the DNA-binding DNA nuclease alone.

In some embodiments, off-target excision is reduced by at least 10%, more preferably at least 40%, more preferably at least 50%, more preferably at least 100% increase compared to the DNA-binding DNA nuclease alone.

In some embodiments, the cell is a eukaryotic cell.

In some embodiments, the cell is a mammalian cell.

In some embodiments, the cell is a plant cell.

In some embodiments, the method further comprises introducing to the cell an additional HDR protein, or a polynucleotide encoding the additional HDR protein.

In some embodiments, the polynucleotide is a modified polynucleotide.

In some embodiments, the modified polynucleotide contains a 1-methyl pseudo-uridine.

In some embodiments, the invention provides a host cell having a genome edit by the methods described herein.

In some embodiments, the invention provides a transgenic organism formed by the methods described herein.

In some embodiments, fusion protein compositions described herein used in the manufacture of a medicament.

In some embodiments, the invention provides a pharmaceutical composition comprising the fusion protein composition described herein.

In some embodiments, the invention provides a method of treating a genetic disease in a patient comprising administering to the patient the pharmaceutical composition comprising the fusion protein composition as described above.

In some embodiments, the invention provides a polynucleotide encoding the fusion protein compositions described herein used in the manufacture of a medicament.

In some embodiments, the invention provides a pharmaceutical composition comprising a polynucleotide encoding the fusion protein compositions described herein.

In some embodiments, the invention provides a method of treating a genetic disease in a patient comprising administering to the patient the pharmaceutical composition comprising the polynucleotide as described above.

Each embodiment disclosed herein is contemplated as being applicable to each of the other disclosed embodiments. Thus, all combinations of the various elements described herein are within the scope of the invention.

BRIEF DESCRIPTION OF THE FIGURES

FIG. 3: Comparison of Cas9-HDRP fusion protein to Cas9 and HDRP co-expression. The experimental design described above was used to determine differences in HDR mediated repair efficiency in cells expressing either Cas9 alone (SEQ ID NO: 5), Rad51-Cas9 fusion protein (SEQ ID NO: 9), or co-expressing unfused Cas9 (SEQ ID NO: 5) and Rad51 (SEQ ID NO: 10) as separate proteins. Rad51-Cas9 fusion protein has a higher HDR mediated repair efficiency compared to either Cas9 protein alone or co-expression of Cas9 and Rad51 proteins (unfused) (FIG. 3A). Notably, Rad51-Cas9 fusion protein had lower protein expression levels compared to cells expressing Cas9 protein alone or co-expressing Cas9 and Rad51 proteins (unfused) (FIG. 3B).

Figure 1:
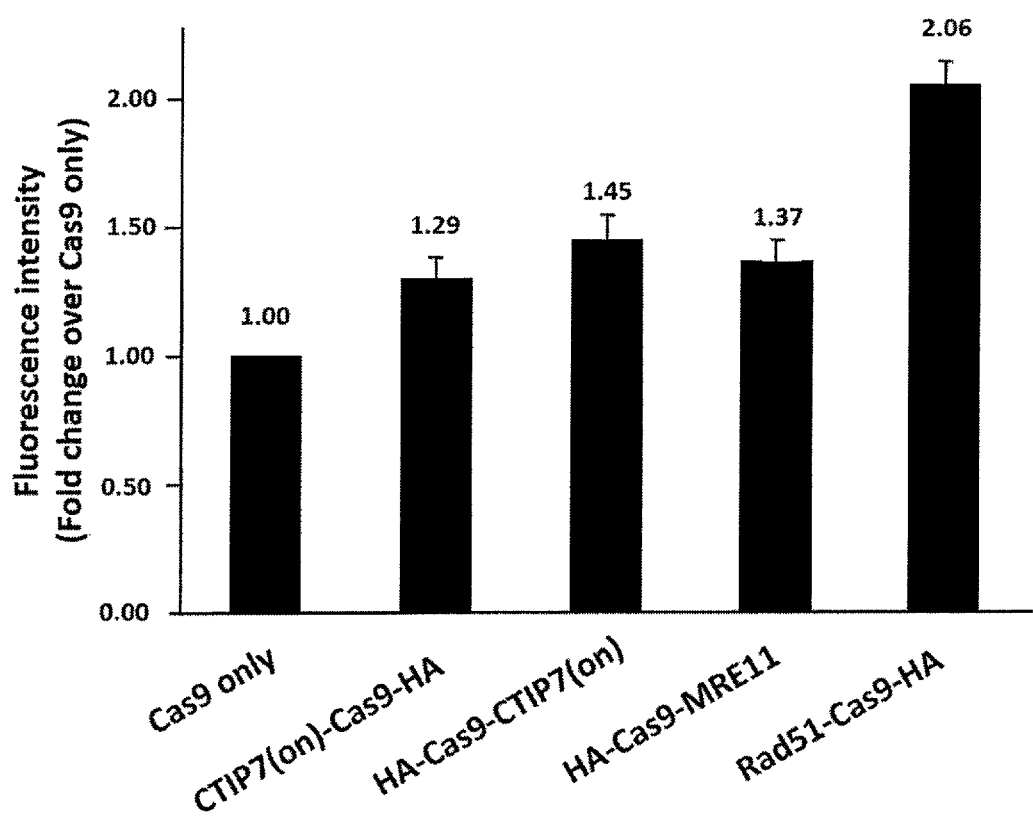
FIG. 1: An increase in frequency of HDR related gene editing events can be achieved by fusing Cas9 to HDR proteins. 293T-iGFP cells were transfected with a mix of the gRNA expression vector pGFP-GUID1, the DNA donor DD-GFP-C-88ss and either the Cas9 expression vector pCDNA3.1 HA-Cas9 (Cas9 only, left), N' terminal CTIP (on)-Cas9 fusion expression vector pCDNA3.1 CtIP(on)-Cas9-HA, C' terminal CTIP(on)-Cas9 fusion expression vector pCDNA3.1-HA-Cas9-CtIP(on), C' terminal MRE11-Cas9 fusion expression vector pCDNA3.1-HA-Cas9-MRE11, or the N' terminal Rad51-Cas9 fusion expression vector pCDNA3.1-RAD51-Cas9-HA. HDR mediated repair efficiency of the inactive GFP gene was determined by measuring fluorescence intensity using a flow cytometer 48 hr post transfection. The results are expressed as fold effect and were obtained by normalizing to the GFP positive fraction of cells transfected with the Cas9 only (pCDNA3.1 HA-Cas9) vector.
Figure 2:
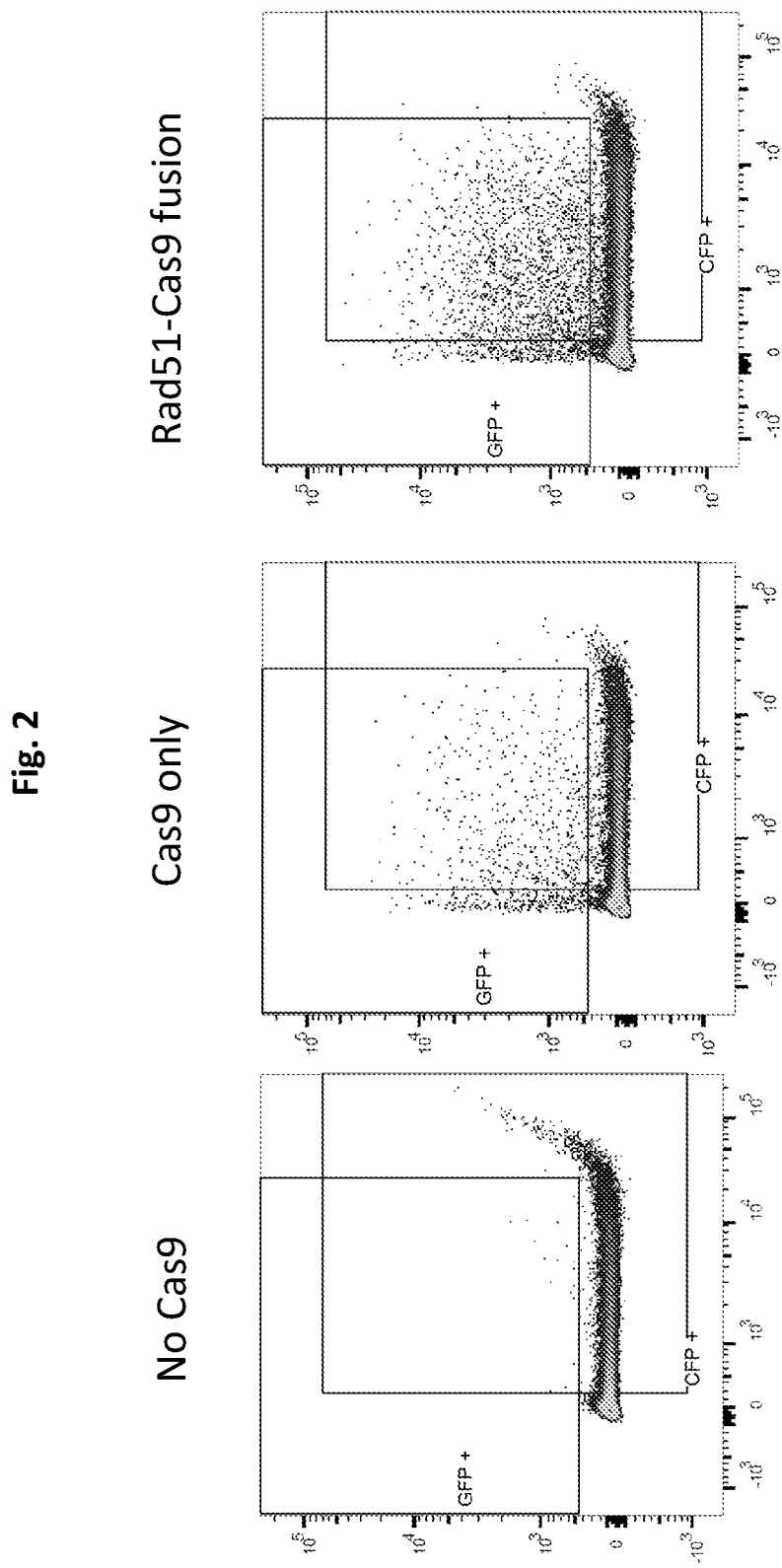
FIG. 2: Flow cytometry read-out of gene editing events. Flow cytometry plots for cells not transfected with Cas9 (No Cas9), cells transfected with Cas9 only, or cells transfected with a Cas9-Rad51 fusion protein are depicted.

The HDR efficacy resulting from transfection of cells with a construct which encodes for one of: Cas9 WT (SEQ ID NO: 5), fusion of Rad51-linker1-Cas9 (SEQ ID NO: 9), fusion of Rad51-linker2-Cas9 (SEQ ID NO: 11), fusion of Rad51-linker3-Cas9 (SEQ ID NO: 12), or co-expression of Rad51 and Cas9 by utilizing a P2A sequence (SEQ ID NO: 13) are compared.

DETAILED DESCRIPTION OF THE INVENTION

Described herein are compositions and methods for increasing the effectiveness of nuclease-mediated (e.g., Cpf1, Cas9, ZFNs and/or TALENs such as FokI-TALE fusions, mega TALs, or compact TALENs) genomic modification by fusing an HDR protein or a functional fragment thereof to a nuclease or a functional fragment thereof thereby promoting the repair of DNA breaks formed by the nuclease by the intrinsic cellular HDR pathway. The increase in the rate of repair of nuclease induced DNA breaks by HDR results in higher accuracy and specificity of genome editing. As shown in the Examples herein, expression of a nuclease-HDRP fusion protein in a cell results in enhanced HDR efficacy compared to co-expression of the nuclease and HDRP separately in a cell.

Terms

Unless otherwise defined, all technical and scientific terms used herein have the same meaning as commonly understood by a person of ordinary skill in the art to which this invention belongs.

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The tams can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acid.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to an identical protein (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity. A "DNA binding DNA nuclease" is any binding protein that is also capable of causing a DNA break or nick. Non-limiting examples of DNA binding DNA nucleases include ZFNs, TALENs and meganucleases. DNA binding DNA nucleases also encompass RNA-guided DNA nucleases, e.g., Cas9, Cpf1 and homologues thereof.

"Targeted insertion" as used herein refers to the result of a successful homologous recombination event wherein a desired portion of a donor DNA was inserted into a desired position in the genome of a cell. "Targeted insertion" also refers to the result of a successful homologous recombination event wherein a desired portion of a donor DNA sequence was copied into a desired position in the genome of a cell. The use of the nuclease-HDR protein chimera of the present invention for genome editing results in an increase of the rate of targeted insertions. This increase can be calculated by quantifying the percentage of cells in a cell population where a targeted insertion event has occurred as a result of nuclease mediated genome editing. Various assays have been described that enable the determination of targeted insertion rates using the genome editing systems described herein. Assay systems for measuring targeted insertion of ZFN mediated genome editing have been described in U.S. Pat. No. 7,951,925. Assay systems for measuring targeted insertion of Cas9 mediated genome editing have been described in U.S. Provisional 61/823,689. Assay systems for measuring targeted insertion of TALEN mediated genome editing have been described in U.S. Pat. No. 8,586,526. Assay systems for measuring targeted insertion of meganuclease mediated genome editing have been described in U.S. Patent Publication No. 20070117128. These assay and other assays that are known in the art may be used to quantify the increase in HR rate and the corresponding targeted insertion rate as mediated by the nuclease-HDRP fusion protein of the present invention.

The term "off-target excision of the genome" as used herein refers to the percentage of cells in a cell population where the DNA of a cell was excised by a nuclease at an undesired locus during or as a result of genome editing. The detection and quantification of off-target insertion events can be done by known methods.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" or "TALEN" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. As a non-limiting example, See, e.g., U.S. Pat. No. 8,586,526.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 8,586,526; 6,140,081; 6,453,242; and 6,534,261; see also WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. Nos. 8,586,526; 5,789,538; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084.

"DNA breaks" refer to both single strand breaks (SSB) and double strand breaks (DSB). SSB are breaks that occur in one of the DNA strands of the double helix. DSB are breaks in which both DNA strands of the double helix are severed.

"DNA Cleavage" refers to the breakage of the covalent backbone of a DNA molecule. DNA Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events at two adjacent loci in the genome. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize. An "engineered cleavage half-domain" is a cleavage half-domain that has been modified so as to form obligate heterodimers with another cleavage half-domain (e.g., another engineered cleavage half-domain). As non-limiting examples see, also, U.S. Pat. Nos. 7,914,796; 8,034,598; 8,623,618 and U.S. Patent Publication No. 2011/0201055.

The term "nucleotide sequence" refers to a nucleotide sequence of any length, which can be DNA or RNA; can be linear, circular or branched and can be either single-stranded or double stranded. The term "donor sequence" refers to a nucleotide sequence that is inserted or copied into a genome. A donor sequence can be of any length, for example between 2 and 10,000 nucleotides in length (or any integer value there between or there above), preferably between about 100 and 1,000 nucleotides in length (or any integer there between), more preferably between about 200 and 500 nucleotides in length.

A "target site" or "target sequence" is a nucleic acid sequence that defines a portion of a nucleic acid to which a DNA binding protein or a fragment thereof can specifically bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small Molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAF-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

The terms "fusion protein" or "chimeric protein" as used herein interchangeably refer to a molecule in which two or more subunit molecules are linked, preferably covalently. The subunit molecules can be the same chemical type of molecule, or can be different chemical types of molecules. Examples of the first type of fusion molecule include, but are not limited to, fusion proteins, for example, a fusion between a nuclease (cleavage) domain (e.g., endonuclease, meganuclease) and an HDR protein. The subunits of a fusion protein may be designed to be in any order, e.g., in the example described above, the nuclease domain may be upstream or downstream of the HDR subunit (on the N-terminal or C-terminal side, respectively) of the HDR subunit. Examples of the second type of fusion molecule include, but are not limited to, a fusion between triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are known in the art and are presented elsewhere in this disclosure.

A "gene," for the purposes of the present disclosure, includes a DNA region encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Plant" cells include, but are not limited to, cells of monocotyledonous (monocots) or dicotyledonous (dicots) plants. Non-limiting examples of monocots include cereal plants such as maize, rice, barley, oats, wheat, sorghum, rye, sugarcane, pineapple, onion, banana, and coconut. Non-limiting examples of dicots include tobacco, tomato, sunflower, cotton, sugarbeet, potato, lettuce, melon, soybean, canola (rapeseed), and alfalfa. Plant cells may be from any part of the plant.

"Eukaryotic" cells include, but are not limited to, fungal cells (such as yeast), plant cells, animal cells, mammalian cells and human cells. Cells may be isolated or not, or in culture or not.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively, linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a nuclease (Cas9, ZFP, TALE) is fused to an HDR protein the nuclease and HDR protein are in operative linkage if, in the fusion polypeptide, nuclease is able to cleave DNA, while the HDR protein is capable of performing its role in the HDR process. Similarly, with respect to a fusion polypeptide in which a DNA-binding domain is fused to an activation or repression domain, the DNA-binding domain and the activation or repression domain are in operative linkage if, in the fusion polypeptide, the DNA-binding domain portion is able to bind its target site and/or its binding site, while the activation domain is able to upregulate gene expression or the repression domain is able to downregulate gene expression.

A "functional fragment" or a "functional derivative" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. The ability of a protein to interact with another protein can be determined, for example, by co-immunoprecipitation, two-hybrid assays or complementation, both genetic and biochemical. See, for example, Fields et al. (1989) Nature 340:245-246; U.S. Pat. No. 5,585,245 and PCT WO 98/44350.

The term "nuclease" as used herein refers to an enzyme capable of cleaving the phosphodiester bonds between the nucleotide subunits of nucleic acid. A nuclease may be isolated or derived from a natural source. A nuclease may be altered or modified to change its activity. For instance, alternations or modifications to a nuclease may change its activity from double-strand break formation to single-strand break formation. The natural source may be any living organism. Alternatively, a nuclease may be a modified or a synthetic protein which retains the phosphodiester bond cleaving activity. The compositions and methods described herein increase nuclease-mediated gene modification. Thus, provided herein are nucleases, for example a fusion protein comprises a nuclease and an HDR protein. As such, gene modification can be achieved using a nuclease, for example an engineered nuclease. Engineered nuclease technology is based on the engineering of naturally occurring DNA-binding proteins.

"DNA-Binding Domains" as used herein refers to any DNA-binding domain can be fused to any of the nucleases used in the compositions and methods disclosed herein, including but not limited to CRISPR/CAS, a zinc finger DNA-binding domain, a TALE DNA binding domain, or a DNA-binding domain from a meganuclease.

DNA Repair by Homologous Recombination

The term "homology directed repair" (HDR) refers to a mechanism by which cells repair DNA damage (double strand DNA lesions and single strand nicks). The most common form of HDR is homologous recombination (HR).

Homologous recombination (HR) is mediated through the Rad52 family of proteins. Rad52 interacts and co-localizes with Rad51, induces Rad51 activity, binds preferentially to DSBs and protects them from exonuclease activity. The initial cellular response to DSBs is mediated through ATM (Ataxia Telangiectasia Mutated) and MRN Complex (Mre11-Rad50-NBS1). The ATM protein is a serine-threonine kinase and a member of the PIKK (Phosphoinositide 3-Kinase-Like Kinase) family, which also includes DNA-PK (DNA Protein Kinase) and ATR (AT and Rad3-related protein). These proteins are associated with DNA damage surveillance, control of cell cycle checkpoints, and cell growth regulation. In response to DSBs, ATM in effect "raises the alarm" to DNA damage, phosphorylating many downstream effector targets such as p53, H2AX, Mdm-2, BRCA11, c-Abl, Chk-2, 53BP1, and SMC-1 (Structural Maintenance Of Chromosome-1). This swift response acts to halt the cell cycle and stop DNA replication ATM; then facilitates DNA repair or triggers apoptosis based on the severity of the damage.

The MRN complex provides paradigm-shifting results of exceptional biomedical interest. MRN is among the earliest respondents to DSBs, and MRN mutations causes' human cancer predisposition diseases Nijmegen breakage syndrome and ATLD (Ataxia Telangiectasia-Like Disorder). MRNs 3-protein multidomain composition promotes its central architectural, structural, enzymatic, sensing, and signaling functions in DSB responses. To organize the MRN complex, the Mre11:exonuclease directly binds NBS1 (Nijmegen Breakage Syndrome 1) DNA, and Rad50. Rad50, which is a SMC related protein, employs it's ABC (ATP-Binding Cassette) ATPase, Zn hook, and coiled coils to bridge DSBs and facilitate DNA end processing by Mre11. Another mammalian protein that participates in the HDR process is the carboxy-terminal binding protein (CtBP)-interacting protein (CtIP). CtIP is known to function in 5' strand resection during homologous recombination independent of or in concert with the MRN complex. Recently EXD2 (also known as EXDL2) was characterized as an exonuclease essential for DSB resection and efficient HR. EXD2 is recruited to chromatin in a damage-dependent manner and confers resistance to DSB-inducing agents. EXD2 functionally interacts with the MRN complex to accelerate resection through its 3'-5' exonuclease activity, which efficiently processes double-stranded DNA substrates containing nicks (Broderick et al. Nat Cell Biol. 2016)

Subsequent steps of DSB repair through homologous recombination include DNA-end recognition, possibly by Rad52, and nucleolytic processing of the broken ends of DNA into 3-end single-stranded DNA. This single-stranded DNA is bound by the Rad51 protein which mediates crucial steps in the reaction, including the search for a homologous duplex template DNA and the formation of joint molecules between the broken DNA ends and the repair template. Rad51 is phosphorylated by c-Abl and this response contributes to the down-regulation of Rad51 activity in ATP-dependent DNA strand exchange reactions. Rad51 protein assembles with single-stranded DNA to form the helical nucleoprotein filament that promotes DNA strand exchange, a basic step of homologous recombination. Rad54 protein interacts with this Rad51 nucleoprotein filament and stimulates its DNA pairing activity, suggesting that Rad54 protein is a component of the nucleoprotein complex involved in the DNA homology search. The binding of Rad54 protein significantly stabilizes the Rad51 nucleoprotein filament formed on either single-stranded DNA or double-stranded DNA. The Rad54-stabilized nucleoprotein filament is more competent in DNA strand exchange and acts over a broader range of solution conditions. The co-assembly of an interacting partner with the Rad51; nucleoprotein filament represents a novel means of stabilizing the biochemical entity central to homologous recombination, and reveals a new function of Rad54 protein. The roles played by BRCA1 and BRCA2 in DSB repair by homologous recombination appear to be somewhat different. Despite the apparent dissimilarity in protein sequence and structure, both BRCA1 and BRCA2 have common biological functions. Their levels are highest during S phase, which is suggestive of functions during DNA replication. Both are localized to the nucleus in somatic cells, where they co-exist in characteristic subnuclear foci that redistribute following DNA damage. BRCA2 controls the intracellular transport and function of Rad51. In BRCA2-deficient cells, Rad51 (which does not contain a consensus nuclear localization signal) is inefficiently transported into the nucleus, which suggests that one function of BRCA2 is to move Rad51 from its site of synthesis to its site of activity. In addition, BRCA2 also appears to control the enzymatic activity of Rad51. Addition of peptides containing the Rad51-binding BRC repeat BRC3, BRC4 or BRC7 inhibits nucleoprotein filament formation. BRCA2 might not directly control Rad51 function, since the stoichiometry of their interaction is possibly low and does not appear to be greatly altered following DNA damage.

Once the homologous DNA has been identified, the subsequent step leads to Strand Invasion and D-loop formation. Damaged DNA strand invades the undamaged DNA duplex in a process referred to as DNA strand exchange. Upon joint-molecule formation and DNA synthesis, branched DNA structures called Holliday junctions can form as late intermediates in homologous recombination. Holliday junctions can slide, or branch-migrate, along the joined DNAs. Branch migration extends the heteroduplex DNA region between identical recombination partners and might thereby provide a mechanism to prevent recombination between repetitive sequences that are dispersed throughout the genome. A DNA Polymerase then extends the 3 end of the invading strand and subsequent ligation by DNA Ligase-I yields a hetero-duplexed DNA structure. Completion of recombination requires the Resolution of Holliday junctions, in order to separate the recombining partners. One well-characterized way of resolving Holliday junctions requires the enzymatic action of a Resolvase. This recombination intermediate is resolved and the precise, error-free correction of the DSB is complete.

The term "HDR protein or a functional fragment thereof" (HDRP) refers to any protein that is known in the art to participate in HDR. Proteins that exhibit any activity that may be related either directly or indirectly to the execution of HDR in cells are to be understood as HDR proteins. In that respect the present invention includes proteins that have known functions, in signaling to other proteins involved in HDR, recruiting other proteins to sites of DNA breaks or proteins that are involved in the repair process per se, are all included in the definition of an HDR protein.

In some embodiments, the HDR protein of the present invention is RAD51, a protein that forms a helical nucleoprotein filament on DNA and controls the homology search and strand pairing of DNA damage repair. Sequences for RAD51 polypeptides and nucleic acids encoding them for a number of species are known in the art, e.g. human RAD51 (NCBI Gene ID: 5888) polypeptide; NCBI Ref Seq: NP 001157741) and nucleic acid (NCBI Ref Seq: NM_001164269).

In some embodiments, the HDR protein of the present invention is BRCA1, an E3 ubiquitin-protein ligase that specifically mediates the formation of 'Lys-6'-linked polyubiquitin chains and plays a central role in DNA repair by facilitating cellular responses to DNA damage. Sequences for BRCA1 polypeptides and nucleic acids encoding them for a number of species are known in the art, e.g. human BRCA1 (NCBI Gene ID: 672) polypeptide (NCBI Ref Seq: NP_009225.1) and nucleic acid (NCBI Ref Seq: NM_007294.3).

In some embodiments, the HDR protein of the present invention is BRCA2, a tumor suppressor gene product that normally functions by binding single-stranded DNA at DNA damage sites and interacting with RAD51 to promote strand invasion. Sequences for BRCA2 polypeptides and nucleic acids encoding them for a number of species are known in the art, e.g. human BRCA2 (NCBI Gene ID: 675) polypeptide (NCBI Ref Seq: NP 000050) and nucleic acid (NCBI Ref Seq: NM 000059).

In some embodiments, the HDR protein of the present invention is Rad54 (ATRX). This protein belongs to the DEAD-like helicase superfamily, and shares similarity with Saccharomyces cerevisiae Rad54, a protein known to be involved in the homologous recombination and repair of DNA. This protein has been shown to play a role in homologous recombination related repair of DNA double-strand breaks. The binding of this protein to double-strand DNA induces a DNA topological change, which is thought to facilitate homologous DNA pairing, and stimulate DNA recombination. Sequences for Rad54 polypeptides and nucleic acids encoding them for a number of species are known in the art, e.g. human Rad54 (NCBI Gene ID: 546) polypeptide (NCBI Ref Seq: NP_000480.3) and nucleic acid (NCBI Ref Seq: NM_000489.4).

In some embodiments, the HDR protein of the present invention is SHFM1, a 26S proteasome complex subunit that interacts directly with BRCA2. Sequences for SHFM1 polypeptides and nucleic acids encoding them for a number of species are known in the art, e.g. human SHFM1 (NCBI Gene ID: 7979) polypeptide (NCBI Ref Seq: NP 006295) and nucleic acid (NCBI Ref Seq: NM 006304).

In some embodiments, the HDR protein of the present invention is PALB2, a DNA-binding protein that binds to single-strand DNA and facilitates accumulation of BRCA2 at the site of DNA damage. PALB2 also interacts with RAD51 to promote strand invasion. Sequences for PALB2 polypeptides and nucleic acids encoding them for a number of species are known in the art, e.g. human PALB2 (NCBI Gene ID: 79728) polypeptide (NCBI Ref Seq: NP 078951) and nucleic acid (NCBI Ref Seq: NM 024675).

In some embodiments, the HDR protein of the present invention is Rad50, a protein that forms a complex with MRE11 and NBS1. The protein complex binds, to DNA and displays numerous enzymatic activities that are required for nonhomologous joining of DNA ends. Sequences for Rad50 polypeptides and nucleic acids encoding them for a number of species are known in the art, e.g. human Rad50 (NCBI Gene ID: 10111) polypeptide (NCBI Ref Seq: NP_005723.2) and nucleic acid (NCBI Ref Seq: NM_005732.3).

In some embodiments, the HDR protein of the present invention is MRE11, a nuclear protein involved in homologous recombination, telomere length maintenance, and DNA double-strand break repair. By itself, the protein has 3' to 5' exonuclease activity and endonuclease activity. The protein forms a complex with the RAD50 homolog; this complex is required for nonhomologous joining of DNA ends and possesses increased single-stranded DNA endonuclease and 3' to 5' exonuclease activities. Sequences for XX polypeptides and nucleic acids encoding them for a number of species are known in the art, e.g. human Rad50 (NCBI Gene ID: 4361) polypeptide (NCBI Ref Seq: NP_005581.2) and nucleic acid (NCBI Ref Seq: NM_005590.3).

In some embodiments, the HDR protein of the present invention, is CtIP (RBBP8), an endonuclease that cooperates with the MRE11-RAD50-NBN (MRN) complex in processing meiotic and mitotic double-strand breaks (DSBs) by ensuring both resection and intrachromosomal association of the broken ends. Sequences for CtIP polypeptides and nucleic acids encoding them for a number of species are known in the art, e.g. human CtIP (NCBI Gene ID: 5932) polypeptide (NCBI Ref Seq: NP_002885.1) and nucleic acid (NCBI Ref Seq: NM_002894.2).

In some embodiments, the HDR protein of the present invention is NBS1, a component of the MRE11-RAD50-NBN (MRN complex) which plays a critical role in the cellular response to DNA damage and the maintenance of chromosome integrity. The complex is involved in double-strand break (DSB) repair, DNA recombination, and maintenance of telomere integrity, cell cycle checkpoint control and meiosis. Sequences for NBS1 polypeptides and nucleic acids encoding them for a number of species are known in the art, e.g. human Nbs1 (NCBI Gene ID: 4683) polypeptide (NCBI Ref Seq: NP_001019859.1) and nucleic acid (NCBI Ref Seq: NM_001024688.2).

In some embodiments, the HDR protein of the present invention is EXD2, a protein that functionally interacts with the MRN complex to accelerate resection through its 3'-5' exonuclease activity, which efficiently processes double-stranded DNA substrates containing nicks. Sequences for EXD2 polypeptides and nucleic acids encoding them for a number of species are known in the art, e.g. human Exd2 (NCBI Gene ID: 55218) polypeptide (NCBI Ref Seq: NP_001180289.1) and nucleic acid (NCBI Ref Seq: NM_001193360.1).

DNA Binding Proteins and DNA Binding Nucleases

In certain embodiments, the DNA-binding domain comprises a zinc finger protein. Preferably, the zinc finger protein is non-naturally occurring in that it is engineered to bind to a target site of choice. See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061.

In certain embodiments, the DNA binding domain is an engineered zinc finger protein that typically includes at least one zinc finger but can include a plurality of zinc fingers (e.g., 2, 3, 4, 5, 6 or more fingers). Usually, the ZFPs include at least three fingers. Certain of the ZFPs include four, five or six fingers. The ZFPs that include three fingers typically recognize a target site that includes 9 or 10 nucleotides; ZFPs that include four fingers typically recognize a target site that includes 12 to 14 nucleotides; while ZFPs having six fingers can recognize target sites that include 18 to 21 nucleotides. The ZFPs can also be fusion proteins that include one or more regulatory domains, wherein these regulatory domains can be transcriptional activation or repression domains.

In other embodiments, the DNA binding domain comprises a TALE DNA binding domain (as a non-limiting example see, U.S. Pat. No. 8,586,526). The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like effectors (TALE) which mimic plant transcriptional activators and manipulate the plant transcriptome (see Kay et al (2007) Science 318:648-

651). These proteins contain a DNA binding domain and a transcriptional activation domain. One of the most well characterized TALEs is AvrBs3 from *Xanthomonas campestgris* pv. *Vesicatoria* (see Bonas et al (1989) Mol Gen Genet. 218: 127-136 and WO2010079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) J Plant Physiol 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) Appl and Envir Micro 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

Thus, in some embodiments, the DNA binding domain that binds to a target site in a target locus (e.g., globin or safe harbor) is an engineered domain from a TAL effector similar to those derived from the plant pathogens *Xanthomonas* (see Boch et al, (2009) Science 326: 1509-1512 and Moscou and Bogdanove, (2009) Science 326: 1501) and *Ralstonia* (see Heuer et al (2007) Applied and Environmental Microbiology 73(13): 4379-4384); U.S. Pat. Nos. 8,420,782 and 8,440,431 and 8,586,526.

An engineered zinc finger or TALE DNA binding domain can have a novel binding specificity, compared to a naturally-occurring zinc finger or TALE protein. Engineering methods include, but are not limited to, rational design and various types of selection.

Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. As non-limiting examples see U.S. Pat. Nos. 6,453,242 and 6,534,261.

Alternatively, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-PpoI, I-SceII, I-CreI, I-TevI, I-TevII and I-TevIII are known. See also U.S. Pat. Nos. 5,420,032; 6,833,252; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996) J. Mol. Biol. 263:163-180; Argast et al. (1998) J Mol. Biol. 280:345-353 and the New England Biolabs catalogue. In addition, the DNA-binding specificity of homing endonucleases and meganucleases can be engineered to bind non-natural target sites. See, for example, Chevalier et al. (2002) Molec. Cell 10:895-905; Epinat et al. (2003) Nucleic Acids Res. 31:2952-2962; Ashworth et al. (2006) Nature 441:656-659; Paques et al. (2007) Current Gene Therapy 7:49-66; U.S. Patent Publication No. 20070117128. DNA-binding domains from meganucleases may also exhibit nuclease activity.

Any nuclease may be operably linked to any HDR protein or HDR protein domain as described herein. The nuclease may comprise heterologous DNA-binding and cleavage domains (e.g., Cpf1, Cas9, zinc finger nucleases; TALENs, and meganuclease DNA-binding domains with heterologous cleavage domains) or, alternatively, the DNA-binding domain of a naturally-occurring nuclease may be altered to bind to a selected target site (e.g., a meganuclease that has been engineered to bind to site different than the cognate binding site). For example, engineering of homing endonucleases with tailored DNA-binding specificities has been described, see, Chames et al. (2005) Nucleic Acids Res 33(20):e178; Arnould et al. (2006) J. Mol. Biol. 355:443-458 and Grizot et al (2009) Nucleic Acids Res July 7 e publication. In addition, engineering of ZFPs has also been described. See, e.g., U.S. Pat. Nos. 6,534,261; 6,607,882; 6,824,978; 6,979,539; 6,933,113; 7,163,824; and 7,013,219.

In certain embodiments, the nuclease domain comprises a meganuclease (homing endonuclease) domain. Naturally-occurring meganucleases recognize 15-40 base-pair cleavage sites and are commonly grouped into four families: the LAGLIDADG family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-PpoI, I-SceII, I-CreI, I-TevI, I-TevII and I-TevIII. Their recognition sequences are known. See also U.S. Pat. Nos. 5,420,032; 6,833,252; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996) J. Mol. Biol. 263:163-180; Argast et al. (1998) J. Mol. Biol. 280:345-353 and the New England Biolabs catalogue. Thus, any meganuclease domain (or functional portion thereof) may be combined with any DNA-binding domain (e.g., ZFP, TALE) to form a nuclease. Furthermore, the nuclease domain may also bind to DNA.

DNA-binding domains from naturally-occurring meganucleases, primarily from the LAGLIDADG family, have been used to promote site-specific genome modification in plants, yeast, Drosophila, mammalian cells and mice, but this approach has been limited to the modification of either homologous genes that conserve the meganuclease recognition sequence (Monet et al. (1999), Biochem. Biophysics. Res. Common. 255: 88-93) or to pre-engineered genomes into which a recognition sequence has been introduced (Route et al. (1994), Mol. Cell. Biol. 14: 8096-106; Chilton et al. (2003), Plant Physiology. 133: 956-65; Puchta et al. (1996), Proc. Natl. Acad. Sci. USA 93: 5055-60; Rong et al. (2002), Genes Dev. 16: 1568-81; Gouble et al. (2006), J. Gene Med. 8(5):616-622). Accordingly, attempts have been made to engineer meganucleases to exhibit novel binding specificity at medically or biotechnologically relevant sites (Porteus et al. (2005), Nat. Biotechnol. 23: 967-73; Sussman et al. (2004), J. Mol. Biol. 342: 31-41; Epinat et al. (2003), Nucleic Acids Res. 31: 2952-62; Chevalier et al. (2002) Molec. Cell 10:895-905; Epinat et al. (2003) Nucleic Acids Res. 31:2952-2962; Ashworth et al. (2006) Nature 441:656-659; Paques et al. (2007) Current Gene Therapy 7:49-66; U.S. Patent Publication Nos. 20070117128; 20060206949; 20060153826; 20060078552; and 20040002092). In addition, naturally-occurring or engineered DNA-binding domains from meganucleases have also been operably linked with a cleavage domain from a heterologous nuclease (e.g., FokI) (also known as mega TALs).

In other embodiments, the nuclease is a zinc finger nuclease (ZFN). ZFNs comprise a zinc finger protein that has been engineered to bind to a target site in a gene of choice and cleavage domain or a cleavage half-domain.

As noted above, zinc finger binding domains can be engineered to bind to a sequence of choice. See, for example, Beerli et al. (2002) Nature Biotechnol. 20:135-141; Pabo et al. (2001) Ann. Rev. Biochem. 70:313-340;

Isalan et al. (2001) Nature Biotechnol. 19:656-660; Segal et al., (2001) Curr. Opin. Biotechnol. 12:632-637; Choo et al. (2000) Curr. Opin. Struct. Biol. 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,453,242 and 6,534,261.

In any of the nucleases described herein, the nuclease can comprise an engineered TALE DNA-binding domain and a nuclease domain (e.g., endonuclease and/or meganuclease domain), also referred to as TALENs. Methods and compositions for engineering these TALEN proteins for robust, site specific interaction with the target sequence of the user's choosing have been published (see U.S. Pat. No. 8,586,526). In some embodiments, the TALEN comprises a endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel et al., (2013) Nucl Acid Res: 1-13, doi: 10.1093/nar/gkt1224). In addition, the nuclease domain may also exhibit DNA-binding functionality.

In still further embodiments, the nuclease comprises a compact TALEN (cTALEN). These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley et al (2013) Nat Comm: 1-8 DOI: 10.1038/ncomms2782). Any TALENs may be used in combination with additional TALENs (e.g., one or more TALENs (cTALENs or FokI-TALENs) with one or more mega-TALs).

Thus, nucleases as described herein also comprise a nuclease (cleavage domain, cleavage half-domain). As noted above, the cleavage domain may be heterologous to the DNA-binding domain, for example a zinc finger or TALE DNA-binding domain and a cleavage domain from a nuclease or a meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) Nucleic Acids Res. 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains and cleavage half-domains Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

In some embodiments, a RNA-guided DNA nuclease may be used to induce a DNA break at a desired location in the genome of a cell. The most commonly used RNA-guided DNA nucleases are derived from CRISPR systems, however, other RNA-guided DNA nucleases are also contemplated for use in the genome editing compositions and methods described herein. For instance, see U.S. Patent Publication No. 2015/0211023, incorporated herein by reference.

In certain embodiments, the nuclease comprises a CRISPR/Cas system. The CRISPR (clustered regularly interspaced short palindromic repeats) locus, which encodes RNA components of the system, and the cas (CRISPR-associated) locus, which encodes proteins (Jansen et al., 2002. Mol. Microbiol. 43: 1565-1575; Makarova et al., 2002. Nucleic Acids Res. 30: 482-496; Makarova et al., 2006. Biol. Direct 1: 7; Haft et al., 2005. PLoS Comput. Biol. 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

CRISPR systems that may be used in the practice of the invention vary greatly. CRISPR systems can be a type I, a type II, or a type III system. Non-limiting examples of suitable CRISPR proteins include Cas3, Cas4, Cas5, Cas5e (or CasD), Cas6, Cas6e, Cas6f, Cas7, Cas8a1, Cas8a2, Cas8b, Cas8c, Cas9, Cas10, Cas1 Od, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cul966.

In some embodiments, the CRISPR protein (e.g., Cas9) is derived from a type II CRISPR system. The Cas9 protein may be derived from *Streptococcus pyogenes, Streptococcus thermophilus, Streptococcus* sp., *Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis,*

*Clostridium botulinum, Clostridium difficile, Finegoldia magna, Natranaerobius thermophilus, Pelotomaculumthermopropionicum, Acidithiobacillus caldus, Acidithiobacillus ferrooxidans, Allochromatium vinosum, Marinobacter sp., Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc sp., Arthrospira maxima, Arthrospira platensis, Arthrospira sp., Lyngbya sp., Microcoleus chthonoplastes, Oscillatoria sp., Petrotoga mobilis, Thermosipho africanus,* or *Acaryochloris marina.*

Thus, an RNA guided DNA nuclease of a Type II CRISPR System, such as a Cas9 protein or modified Cas9 or homolog or ortholog of Cas9, or other RNA guided DNA nucleases belonging to other types of CRISPR systems, such as Cpf1 and its homologs and orthologs, may be used in the fusion proteins of the present invention.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called "adaptation", (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

The term guide RNA (gRNA) refers to an RNA molecule capable of forming a complex with a Cas protein e.g., Cas9 and wherein said complex is capable of targeting a DNA sequence i.e., genomic DNA sequence having a nucleotide sequence which is complementary to said gRNA.

The term "guide RNA" (gRNA) is a 20bp RNA molecule that can form a complex with CRISPR-associated nuclease and serve as the DNA recognition module.

The term "single guide RNA" (sgRNA), is a 20bp RNA molecule that can form a complex with a CRISPR-associated nuclease and serve as the DNA recognition module. sgRNA is designed as a synthetic fusion of the CRISPR RNA (crRNA, or guide RNA) and the trans-activating crRNA (tracrRNA). However, sgRNA is not strictly required, as the use of separate guide RNA and tracrRNA molecules which connect to each other via basepairing may also be used to target the CRISPR-associated nuclease. With regard to Cas9, Cpf1 and other RNA guided DNA nucleases, the term "DNA binding DNA nuclease" encompasses a RNA guided DNA nuclease pre-assembled with or unbound to a gRNA or sgRNA. For methods which utilize a RNA-guided DNA nuclease-HDRP fusion protein for genome editing in a cell, a gRNA or sgRNA capable of targeting the RNA guided DNA nuclease to a DNA target site must be present in the cell to induce the desired double-strand break and subsequent genome edit.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

According to one aspect, a DNA binding protein having two or more nuclease domains may be modified or altered to inactivate all but one of the nuclease domains. Such a modified or altered DNA binding protein is referred to as a DNA binding protein nickase, to the extent that the DNA binding protein cuts or nicks only one strand of double stranded DNA. When guided by RNA to DNA, the DNA binding protein nickase is referred to as an RNA guided DNA binding protein nickase.

An exemplary DNA binding protein is an RNA guided DNA binding protein nuclease of a Type II CRISPR System, such as a Cas9 protein or modified Cas9 or homolog of Cas9. An exemplary DNA binding protein is a Cas9 protein nickase. An exemplary DNA binding protein is an RNA guided DNA binding protein of a Type II CRISPR System which lacks nuclease activity. An exemplary DNA binding protein is a nuclease-null Cas9 protein.

According to certain aspects of methods of RNA-guided genome regulation described herein, Cas9 is altered to reduce, substantially reduce or eliminate nuclease activity. According to one aspect, Cas9 nuclease activity is reduced, substantially reduced or eliminated by altering the RuvC nuclease domain or the HNH nuclease domain. According to one aspect, the RuvC nuclease domain is inactivated According to one aspect, the HNH nuclease domain is inactivated. According to one aspect, the RuvC nuclease domain and the HNH nuclease domain are inactivated. According to an additional aspect, Cas9 proteins are provided where the RuvC nuclease domain and the HNH nuclease domain are inactivated. According to an additional aspect, nuclease-null Cas9 proteins are provided insofar as the RuvC nuclease domain and the HNH nuclease domain are inactivated. According to an additional aspect, a Cas9 nickase is provided where either the RuvC nuclease domain or the HNH nuclease domain is inactivated, thereby leaving the remaining nuclease domain active for nuclease activity. In this manner, only one strand of the double stranded DNA is cut or nicked.

According to an additional aspect, nuclease-null Cas9 proteins are provided where one or more amino acids in Cas9 are altered or otherwise removed to provide nuclease-null Cas9 proteins. According to one aspect, the amino acids include D10 and H840. According to an additional aspect, the amino acids include D839 and N863. According to one aspect, one or more or all of D10, H840, D839 and H863 are substituted with an amino acid which reduces, substantially eliminates or eliminates nuclease activity. According to one aspect, one or more or all of D10, H840, D839 and H863 are substituted with alanine. According to one aspect, a Cas9 protein having one or more or all of D10, H840, D839 and H863 substituted with an amino acid which reduces, substantially eliminates or eliminates nuclease activity, such as alanine, is referred to as a nuclease-null Cas9 or dCas9 and exhibits reduced or eliminated nuclease activity, or nuclease activity is absent or substantially absent within, levels of detection. According to this aspect, nuclease activity for a dCas9 may be undetectable using known assays, i.e. below the level of detection of known assays.

According to one aspect, the Cas9 protein, Cas9 protein nickase or nuclease null Cas9 includes homologs and orthologs thereof which retain the ability of the protein to bind to the DNA and be guided by the RNA. According to one aspect, the Cas9 protein includes the sequence as set forth for naturally occurring Cas9 from *S. pyogenes* and protein sequences having at least 30%, 40%, 50%, 60%, 70%, 80%, 90%, 95%, 98% or 99% homology thereto and being a DNA binding protein, such as an RNA guided DNA binding protein. According to one aspect, an engineered Cas9-gRNA system is provided which enables RNA-guided genome regulation in cells by tethering transcriptional activation domains to either a nuclease-null Cas9 or to guide RNAs.

In some embodiments, the CAS protein is Cpf1, a putative class 2 CRISPR effector. Cpf1 mediates robust DNA interference with features distinct from Cas9. Cpf1 is a single RNA-guided endonuclease lacking tracrRNA, and it utilizes a T-rich protospacer-adjacent motif. Cpf1 cleaves DNA via a staggered DNA double-stranded break. two Cpf1 enzymes from Acidaminococcus and Lachnospiraceae have been shown to carry out efficient genome-editing activity in human cells. (Zetsche et al. Cell. 2015).

Target Sites

As described in detail above, DNA domains in the nucleases (ZFNs, TALENs and/or RNAs of CRISPR/Cas) can be engineered to bind to any sequence of choice in a locus. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual (e.g., zinc finger) amino acid sequences, in which each triplet or quadruplet nucleotide sequence is associated with one or more amino acid sequences of DNA binding domain which bind the particular triplet or quadruplet sequence.

In addition, a nuclease or a functional fragment thereof and a HDR protein or functional domain thereof may be linked together using any polypeptide linker, including for example, linkers of 5 amino acids or less, linkers of between 5 and 10 amino acids, linkers of between 10 and 20 amino acids, linkers of between 20 and 30 amino acids, linkers of between 10 and 100 amino acids, linkers of between 50 and 200 amino acids, linkers of between 100 and 300 amino acids, linkers of more than 300 amino acids.

Additionally, single guide RNAs can be engineered to bind to a target of choice in a genome by commonly known methods known in the art for creating specific RNA sequences. These single guide RNAs are designed to guide the Cas9 to any chosen target site.

Donors

As noted above, insertion of an exogenous sequence (also called a "donor sequence" or "donor"), for example for correction of a mutant gene or for increased expression of a wild-type gene also can be carried out. It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest. Depending on the mechanism of HDR used in response to the nuclease induced break, the desired sequence of the donor molecule may be inserted, copied, or otherwise introduced into the DNA target site.

The donor polynucleotide can be DNA or RNA, single-stranded and/or double-stranded and can be introduced into a cell in linear or circular form. See, e.g., U.S. Patent Publication Nos. 20100047805; 20110281361; and 20110207221. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) Proc. Natl. Acad. Sci. USA 84:4959-4963; Nehls et al. (1996) Science 272: 886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A donor sequence may also be an oligonucleotide and be used for gene correction or targeted alteration of an endogenous sequence. The oligonucleotide may be introduced to the cell on a vector, may be electroporated into the cell, or may be introduced via other methods known in the art. The oligonucleotide can be used to 'correct' a mutated sequence in an endogenous gene (e.g., the sickle mutation in beta globin), or may be used to insert sequences with a desired purpose into an endogenous locus.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

The donor is generally inserted so that its expression is driven by the endogenous promoter at the integration site, namely the promoter that drives expression of the endogenous gene into which the donor is inserted. However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. For example, a transgene as described herein may be inserted into an endogenous locus such that some (N-terminal and/or C-terminal to the transgene) or none of the endogenous sequences are expressed, for example as a fusion with the transgene. In other embodiments, the transgene (e.g., with or without additional coding sequences such as for the endogenous gene) is integrated into any endogenous locus, for example a safe-harbor locus, for example a CCR5 gene, a CXCR4 gene, a PPP1R12c (also known as AAVS1) gene, an albumin gene or a Rosa gene. See, e.g., U.S. Pat. Nos. 7,951,925 and 8,110,379; U.S. Publication Nos. 20080159996; 201000218264; 20100291048; 20120017290; 20110265198; 20130137104; 20130122591; 20130177983 and 20130177960 and U.S. Provisional Application No. 61/823,689).

When endogenous sequences (endogenous or part of the transgene) are expressed with the transgene, the endogenous sequences may be full-length sequences (wild-type or mutant) or partial sequences. Preferably the endogenous sequences are functional. Non-limiting examples of the function of these full length or partial sequences include increasing the serum half-life of the polypeptide expressed by the transgene (e.g., therapeutic gene) and/or acting as a carrier.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

In certain embodiments, the donor molecule comprises a sequence selected from the group consisting of a gene encoding a protein (e.g., a coding sequence encoding a protein that is lacking in the cell or in the individual or an alternate version of a gene encoding a protein), a regulatory sequence and/or a sequence that encodes a structural nucleic acid such as a microRNA or siRNA.

Delivery

The proteins (e.g., ZFPs, TALENs, CRISPR/Cas) and/or polynucleotides encoding same, any donor polynucleotides and HDR proteins or functional domains thereof used in the described herein may be delivered to a target cell by any suitable means.

Methods of delivering proteins comprising nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824.

Zinc finger, TALE or CRISPR/Cas proteins as described herein may also be delivered using vectors containing sequences encoding one or more of the zinc finger proteins, zinc finger nucleases, TAL-effector domain proteins, TALENs and/or CRISPR/Cas protein(s). Donor encoding polynucleotides may be similarly delivered. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 8,586,526; 6,534,261; 6,607,882; 6,824,978; 6,933,113; 6,979,539; 7,013,219; and 7,163,824. Furthermore, it will be apparent that any of these vectors may comprise one or more zinc finger protein-encoding sequences, one or more CRISPR/Cas-encoding sequences or one or more TALE-encoding sequences. Thus, when one or more nucleases or nuclease systems and/or donors are introduced into the cell, the nucleases or nuclease systems and/or donors may be carried on the same vector or on different vectors. When multiple vectors are used, each vector may comprise a sequence encoding one or multiple ZFPs, TALEs, nucleases comprising ZFPs and/or TALEs, CRISPR/Cas system and/or donors.

Conventional viral and non-viral based gene transfer methods can be used to introduce nucleic acids encoding engineered chimeras and/or donors in cells (e.g., mammalian cells) and target tissues. Such methods can also be used to administer nucleic acids encoding chimeras and/or donors to cells in vitro. In certain embodiments, nucleic acids encoding chimeras and/or donors are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, Science 256:808-813 (1992); Nabel & Feigner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bohm (eds.) (1995); and Yu et al., Gene Therapy 1:13-26 (1994).

Methods of non-viral delivery of nucleic acids include electroporation, lipofection, microinjection, biolistics, particle gun acceleration, virosomes, liposomes, immunoliposomes, polycation or lipid:nucleic acid conjugates, naked DNA, mRNA, artificial virions, and agent-enhanced uptake of DNA or can be delivered to plant cells by bacteria or viruses (e.g., Agrobacterium, Rhizobium sp. NGR234, Sinorhizoboiummeliloti, Mesorhizobium loti, tobacco mosaic virus, potato virus X, cauliflower mosaic virus and cassaya vein mosaic virus. See, e.g., Chung et al. (2006) Trends Plant Sci. 11(1):1-4. Sonoporation using, e.g., the Sonitron 2000 system (Rich-Mar) can also be used for delivery of nucleic acids. Cationic-lipid mediated delivery of proteins and/or nucleic acids is also contemplated as an in vivo or in vitro delivery method. See Zuris et al. (2015) Nat. Biotechnol. 33(1):73-80. See also Coelho et al. (2013) N. Engl. J. Med. 369, 819-829; Judge et al. (2006) Mol. Ther. 13, 494-505; and Basha et al. (2011) Mol. Ther. 19, 2186-2200. In one embodiment, one or more nucleic acids are delivered as mRNA. Also optional is the use of capped mRNAs to increase translational efficiency and/or mRNA stability.

Additional exemplary nucleic acid delivery systems include those provided by Amaxa®. Biosystems (Cologne, Germany), Maxcyte, Inc. (Rockville, Md.), BTX Molecular Delivery Systems (Holliston, Mass.) and Copernicus Therapeutics Inc., (see for example U.S. Pat. No. 6,008,336). Lipofection is described in e.g., U.S. Pat. Nos. 5,049,386, 4,946,787; and 4,897,355) and lipofection reagents are sold commercially (e.g., Transfectam™, Lipofectin™ and Lipofectamine™ RNAiMAX). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiamid et al (2009) Nature Biotechnology 27(7) p. 643).

The use of RNA or DNA viral based systems for the delivery of nucleic acids encoding engineered Cas, ZFPs, TALEs, ZFNs, TALENs and/or donors take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of chimeric proteins include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g. Buchscher et al., J. Virol. 66:2731-2739 (1992); Johann et al., J. Virol. 66:1635-1640 (1992); Sommerfelt et al., Virol. 176:58-59 (1990); Wilson et al., J. Virol. 63:2374-2378 (1989); Miller et al., J. Virol. 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors is described in a number of publications, including U.S. Pat. No. 5,173,414; Tratschin et al., Mol. Cell. Biol. 5:3251-3260 (1985); Tratschin et al., Mol. Cell. Biol. 4:2072-2081 (1984); Hermonat & Muzyczka, PNAS 81:6466-6470 (1984); and Samulski et al., J. Virol. 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., Blood 85:3048-305 (1995); Kohn et al., Nat. Med. 1:1017-102 (1995); Malech et al., PNAS 94:22 12133-12138 (1997)). PA317/pLASN was the first therapeutic vector used in a gene therapy trial. (Blaese et al., Science 270:475-480 (1995)). Transduction efficiencies of 50% or greater have been observed for MFG-S packaged vectors. (Ellem et al., Immunol Immunother. 44(1):10-20 (1997); Dranoff et al., Hum. Gene Ther. 1:111-2 (1997).

Recombinant adeno-associated virus vectors (rAAV) are a promising alternative gene delivery systems based on the defective and nonpathogenic parvovirus adeno-associated type virus. The vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., Lancet 351:9117 1702-3 (1998), Kearns et al., Gene Ther. 9:748-55 (1996)). Other AAV serotypes, including AAV1, AAV3, AAV4, AAV5, AAV6 and AAV8, AAV 8.2, AAV9, and AAV rh10 and pseudotyped AAV such as AAV2/8, AAV2/5 and AAV2/6 can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., Hum. Gene Ther. 7:1083-9 (1998)). Additional examples of the use of adenovirus vectors for gene transfer in clinical trials include Rosenecker et al., Infection 24:1 5-10 (1996); Sterman et al., Hum. Gene Ther. 9:7 1083-1089 (1998); Welsh et al., Hum. Gene Ther. 2:205-18 (1995); Alvarez et al., Hum. Gene Ther. 5:597-613 (1997); Topf et al., Gene Ther. 5:507-513 (1998); Sterman et al., Hum. Gene Ther. 7:1083-1089 (1998).

Packaging cells are used to form virus particles that are capable of infecting a host cell. Such cells include 293 cells, which package adenovirus, AAV, and .psi.2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additionally, AAV can be produced at clinical scale using baculovirus systems (see U.S. Pat. No. 7,479,554).

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., Proc. Natl. Acad. Sci. USA 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

In some embodiments, one or more polynucleotide of the present invention may be combined on the same construct. In some embodiments, one or more polynucleotide of the present invention may be on different constructs. In Some embodiments, one or more polynucleotide of the present invention may be packed in different viruses or vectors, and any polynucleotide may have a separate promotor controlling transcription of said polynucleotide. In some embodiments, one or more polynucleotides of the present invention may be expressed under the same promoter.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFP nucleic acid (gene or cDNA), and re-infused back into the subject organism (e.g., patient). Various cell types suitable for ex vivo transfection are well known to those of skill in the art (see, e.g., Freshney et al., Culture of Animal Cells, A Manual of Basic Technique (3rd ed. 1994)) and the references cited therein for a discussion of how to isolate and culture cells from patients).

Suitable cells include but not limited to eukaryotic and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NSO, SP2/0-Ag14, HeLa, HEK293 (e.g., HEK293-F, HEK293-H, HEK293-T), and perC6 cells, any plant cell (differentiated or undifferentiated) as well as insect cells such as *Spodopterafugiperda* (Sf), or fungal cells such as *Saccharomyces, Pichia* and *Schizosaccharomyces*. In certain embodiments, the cell line is a CHO-K1, MDCK or HEK293 cell line. Additionally, primary cells may be isolated and used ex vivo for reintroduction into the subject to be treated following treatment with the nucleases (e.g. ZFNs or TALENs) or nuclease systems (e.g. CRISPR/Cas). Suitable primary cells include peripheral blood mononuclear cells (PBMC), and other blood cell subsets such as, but not limited to, CD4+ T cells or CD8+ T cells. Suitable cells also include stem cells such as, by way of example, embryonic stem cells, induced pluripotent stem cells, hematopoietic stem cells (CD34+), neuronal stem cells and mesenchymal stem cells.

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-.gamma. and TNF-alpha are known (as a non-limiting example see, Inaba et al., J. Exp. Med. 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+(panB cells), GR-1 (granulocytes), and Iad (differentiated antigen presenting cells) (as a non-limiting example see Inaba et al., J. Exp. Med. 176: 1693-1702 (1992)).

Stem cells that have been modified may also be used in some embodiments. For example, stem cells that have been made resistant to apoptosis may be used as therapeutic compositions where the stem cells also contain the ZFPs, TALEs, ZFNs, TALENs, CRISPR/Cas systems and/or donors of the invention. Resistance to apoptosis may come about, for example, by knocking out BAX and/or BAK using BAX- or BAK-specific nucleases (see, U.S. Patent Publication No. 2010/0003756) in the stem cells, or those that are disrupted in a caspase, again using caspase-6 specific ZFNs for example. Alternatively, resistance to apoptosis can also be achieved by the use of caspase inhibitors like Z-VAD-FMK (carbobenzoxy-valyl-alanyl-aspartyl-[O-methyl]fluoromethylketone).

Vectors (e.g., retroviruses, adenoviruses, liposomes, etc.) containing therapeutic ZFPs, TALEs, ZFNs, TALENs, CRISPR/Cas system and/or donor nucleic acids can also be administered directly to an organism for transduction of cells in vivo. Alternatively, naked DNA or mRNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34.sup.+ cells, include adenovirus Type 35.

Vectors suitable for introduction of transgenes into immune cells (e.g., T-cells) include non-integrating lentivirus vectors. See, for example, U.S. Patent Publication No 20090117617.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., Remington's Pharmaceutical Sciences, 17th ed., 1989).

Applications

The disclosed fusion protein compositions may be used in methods for genome editing and increasing the rate of homology directed recombination at target site in the genome of a cell. Such methods utilizing the fusion protein compositions increase the rate of DNA insertion by homologous directed recombination at a target site by at least 10%, more preferably at least 20%, more preferably at least 30%, more preferably at least 40%, more preferably at least 50%, more preferably at least 100% compared to the DNA-binding DNA nuclease alone. Such methods also reduce the rate of off-target excision by at least 10%, more preferably at least 20%, more preferably at least 30%, more preferably at least 40%, more preferably at least 50%, more preferably at least 100% compared to the DNA-binding DNA nuclease alone. Thus, the disclosed compositions and methods can be used for any application in which it is desired to increase nuclease-mediated genomic modification in any cell type, including clinical applications nuclease-based therapies feasible in a clinical setting as well as agricultural (plant) applications. For example, the methods described herein will improve the therapeutic effect of ZFNs, TALENs, and/or CRISPR/Cas systems in the following scenarios: ex vivo and in vivo gene disruption (CCR5) in CD34+ cells (see, e.g., U.S. Pat. No. 7,951,925); ex vivo and in vivo gene correction of hemoglobinopathies in CD34+ cells (see, e.g., U.S. Application No. 61/694,693); and/or ex vivo and in vivo gene addition to albumin locus for therapy of lysosomal storage diseases and hemophilias (see, e.g., U.S. Patent Publication Nos. 20140017212 and 20130177983). The disclosed compositions and methods may also be used in the manufacture of a medicament or pharmaceutical composition for treating genetic diseases in a patient.

In addition, the methods and compositions described herein can be used to generate model organisms and cell lines, including the generation of stable knock-out cells in any given organism. While ZFN, TALENs and CRISPR/Cas systems offer the ability to knock-out any given gene in cell lines or model organism, in the absence of selection marker these events however can be very rare. Accordingly, the methods described herein, which significantly increase the rate of targeted gene correction, can be used to generate cell lines with new properties. This includes cell lines used for the production of biologicals like Hamster (CHO) cell lines or cell lines for the production of several AAV serotypes like human HEK 293 cells or insect cells like Sf9 or Sf21 genomically-modified plants and plant lines.

The methods and compositions of the invention can also be used in the production of non-human transgenic organisms. Transgenic animals can include those developed for disease models, as well as animals with desirable traits. Embryos may be treated using the methods and compositions of the invention to develop transgenic animals. In some embodiments, suitable embryos may include embryos from small mammals (e.g., rodents, rabbits, etc.), companion animals, livestock, and primates. Non-limiting examples of rodents may include mice, rats, hamsters, gerbils, and guinea pigs. Non-limiting examples of companion animals may include cats, dogs, rabbits, hedgehogs, and ferrets. Non-limiting examples of livestock may include horses, goats, sheep, swine, llamas, alpacas, and cattle. Non-limiting examples of primates may include capuchin monkeys, chimpanzees, lemurs, macaques, marmosets, tamarins, spider monkeys, squirrel monkeys, and vervet monkeys. In other embodiments, suitable embryos may include embryos from fish, reptiles, amphibians, or birds. Alternatively, suitable embryos may be insect embryos, for instance, a Drosophila embryo or a mosquito embryo.

Transgenic organisms contemplated by the methods and compositions of this invention also include transgenic plants and seeds. Examples of suitable transgenes for introduction include exogenous nucleic acid sequence that may comprise a sequence encoding one or more functional polypeptides (e.g., a cDNA), with or without one or more promoters and/or may produce one or more RNA sequences (e.g., via one or more shRNA expression cassettes), which impart desirable traits to the organism. Such traits in plants include, but are not limited to, herbicide resistance or tolerance; insect resistance or tolerance; disease resistance or tolerance (viral, bacterial, fungal, nematode); stress tolerance and/or resistance, as exemplified by resistance or tolerance to drought, heat, chilling, freezing, excessive moisture, salt stress; oxidative stress; increased yields; food content and makeup; physical appearance; male sterility; drydown; standability; prolificacy; starch quantity and quality; oil quantity and quality; protein quality and quantity; amino acid composition; and the like. Of course, any two or more exogenous nucleic acids of any description, such as those conferring herbicide, insect, disease (viral, bacterial, fungal, nematode) or drought resistance, male sterility, drydown, standability, prolificacy, starch properties, oil quantity and quality, or those increasing yield or nutritional quality may be employed as desired. In certain embodiments, the exogenous nucleic acid sequence comprises a sequence encoding a herbicide resistance protein (e.g., the AAD (aryloxyalkanoatedioxygenase) gene) and/or functional fragments thereof.

Kits

In another aspect, the invention provides kits that are useful for increasing gene disruption and/or targeted integration following nuclease-mediated cleavage of a cell's genome. (e.g. Cas9, ZFNs, TAL-effector domain nuclease fusion proteins, or engineered homing endonucleases or engineered guide RNAs with the CRISPR/Cas system). The kits typically include one or more nuclease-HDR protein chimera that bind to a target site and instructions for introducing the nuclease-HDR protein chimera into the cells such that nuclease-mediated gene disruption and/or targeted integration is enhanced.

Optionally, cells containing the target site(s) of the nuclease may also be included in the kits described herein.

In certain embodiments, the kits comprise at least one construct with the target gene and a known nuclease capable of cleaving within the target gene. Such kits are useful for optimization of cleavage conditions in a variety of varying host cell types.

Other kits contemplated by the invention may include a nuclease-HDR protein chimera capable of cleaving within a known target locus within a genome, and may additionally comprise a donor nucleic acid.

The kits typically contain polynucleotides encoding one or more nucleases and donor polynucleotides as described herein as well as instructions for introducing the nucleases and/or donor polynucleotide to cells. The kits can also contain cells, buffers for transformation of cells, culture media for cells, and/or buffers for performing assays. Typically, the kits also contain a label which includes any material such as instructions, packaging or advertising leaflet that is attached to or otherwise accompanies the other components of the kit.

EXAMPLES

Example 1: Genome Editing by Cas9-HDRP Increases the Rate of GFP Gene Correction An assay system for determining the recombination rates of donor DNA to a desired location in the genome is described. Specifically, an HDRP-Cas9 fusion protein system for enhanced CRISPR-Cas directed recombination at a desired location in the genome of a human cell. The system comprises:

1. pLeti6V5-iGFP2 lenti-viral expression vector SEQ ID NO: 01 harboring a GFP gene which comprises two stop codon mutations at locations 96-99 and 102-105 of the GFP coding sequence SEQ ID NO: 02. These stop codons lead to premature termination during translation and results in a truncated GFP protein comprising the first 31 amino acids of the GFP protein. This fragment alone lacks any fluorescence properties detectable by standard detection methods (e.g light microscopy Flow-cytometry and microplate reader). In addition, the vector also includes a Blasticidin resistance gene that enables viability-based selection towards cells in which the vector has been integrated in the genome. The pHAGE-iGFP vector contains the genetic elements required for packaging, transduction and stable integration of viral expression construct into genomic DNA as well as Puromycin resistance gene.
2. pLeti6V5-iGFP2 is transduced into human embryonic kidney 293T cells to produce stably expressing cell-line as follows:
   a. pLeti6V5-iGFP2 is delivered into 293T producer cells by simultaneous transfection with a mix of 3 packaging plasmids (pPACKH1TM, System Biosciences), using the transfection reagent Lipofectamine®3000 and following the protocol provided by the manufacturer.
   b. The resulting pseudo viral particles are collected after 48 hr and used to infect a fresh batch of human embryonic kidney 293T cells by applying 500 of viral particles containing medium directly on the cells.
   c. 48 hr after infection, the medium is replaced with Blaticidin containing medium at final concentration of 1 μg/ml.
   d. Blasticidin resistant cells are collected 10 days later. The collected cells harbor the inactive GFP construct in their genome and are referred to in this application as 293T-iGFP.
3. pGFP-GUID1 is an expression vector carrying a U6 promoter followed by DNA encoding a guide RNA that targets the inactive GFP gene at a location between the two premature stop codons and a trans-activating CRISPR RNA scaffold (SEQ ID NO: 03).
4. DD-GFP-C-88ss: (SEQ ID NO: 04) is a synthetic single stranded DNA of 88 nucleotides with partial homology to the inactive GFP site on piGFP. DD-GFP-ss also contains the correct GFP sequence segment that is missing from the inactive GFP. It is designed to be used as donor DNA in a genome editing reaction to restore the iGFP gene to its original GFP form.
5. pCDNA3.1 HA-Cas9 is a mammalian expression vector. It expresses a Cas9 protein fused to a HA tag at its N' terminal end (SEQ ID NO: 05).
6. pCDNA3.1 CtIP(on)-Cas9-HA is a mammalian expression vector. It expresses a Cas9 protein fused to the C' terminal end of a mutated human CtIP protein via short linker peptide. This fusion protein also contains HA tag at its C' terminal end (SEQ ID NO: 06). The 7 mutations along CtIP ORF sequence were shown to generate an activated CtIP variant, which is primed for HDR functionality in the absence of a global cellular DNA damage response signaling. The introduced mutations lead to the following changes in the protein sequence: S231D, S347D, T847D, T859D, K432R, K526R, K604R.
7. pCDNA3.1-HA-Cas9-CtIP(on) is a mammalian expression vector. It is expresses CtIP(on) (the same mutated human CtIP protein as pCDNA3.1 CtIP(on)-Cas9-HA) fused to the C' terminal end of Cas9 through a linker peptide. This fusion protein also contains HA tag at its N' terminal end (SEQ ID NO: 07).
8. pCDNA3.1-HA-Cas9-MRE11 is a mammalian expression vector. It is expresses the human MRE11 protein fused to the C' terminal end of Cas9 through a linker peptide. This fusion protein also contains HA tag at its N' terminal end (SEQ ID NO: 08).
9. pCDNA3.1-RAD51-linker1-Cas9-HA (also referred to as RAD51-CAS9) is a mammalian expression vector. It expresses the human Rad51 protein fused to the N' terminal end of Cas9 through a linker1 peptide (SEQ ID NO: 14). This fusion protein also contains an HA tag at its C' terminal end (SEQ ID NO: 09). This construct is utilized in this Example, as well as in Example 2 and Example 3, below.
10. pCDNA3.1-HA-RAD51 is a mammalian expression vector. It expresses the human Rad51 protein fused to HA tag at its N terminal end (SEQ ID NO: 10). This construct is utilized in Example 2, below.
11. pCDNA3.1-RAD51-linker2-Cas9-HA is a mammalian expression vector. It expresses the human Rad51 protein fused to the N' terminal end of Cas9 through a linker2 peptide, which is a rigid linker that contains a helix (SEQ ID NO: 15). This fusion protein also contains an HA tag at its C' terminal end (SEQ ID NO: 11). This construct is utilized in Example 3, below.
12. pCDNA3.1-RAD51-linker3-Cas9-HA is a mammalian expression vector. It expresses the human Rad51 protein fused to the N' terminal end of Cas9 through a linker3 peptide (SEQ ID NO: 16). This fusion protein also contains an HA tag at its C' terminal end (SEQ ID: 12). This construct is utilized in Example 3, below.

13. pCDNA3.1-CAS9-P2A-RAD51 is a mammalian expression vector for co-expression of CAS9 and Rad51. The P2A sequence was introduced between the sequences encoding CAS9 and Rad51 to generate two separate proteins (the Cas9 and Rad51) from one transcript (SEQ ID: 13). This construct is utilized in Example 3, below.

The effect of Cas9 or Cas9-HDRP fusions on HDR efficacy was determined as follows: 600 ng of an expression vector carrying one of the relevant expression cassettes (i.e., Cas9 with or without HDRP fusion, SEQ ID Nos: 05-09), was introduced into 293T-iGFP cells along with 20 pmol of the donor DNA oligo DD-GFP-C-88ss and 50 ng of the guide RNA expression vector pGFP-GUID1. Transfected cells were harvested from individual wells of 6-well plate at 48 hr post transfection. Cell suspensions of each sample were then transferred to a FACS compatible tube for measurement of GFP florescent intensity. Flow cytometry was performed on a BD-LSRII (Becton Dickinson) and Analysis was done using FlowJo FACS analysis software.

Since GFP signal ultimately requires the correction of the GFP ORF by HDR using the GFP correction donor DNA DD-GFP-C-88ss, the percentage of GFP positive events in the population directly correlates with HDR efficiency in this assay. To determine the contribution of HDRP's-Cas9 fusion proteins to the efficiency of CRISPR mediated HDR in the described assay, we tested several Cas9-HDRP fusion constructs and compare the fraction of GFP positive cells in each case to that obtained with Cas9 alone.

Following this experimental scheme, analysis of a population of cells expressing the Cas9-HDRP fusion protein determines the percentage of GFP positive cells is at least 10% higher, preferably at least 100% higher, compared to the population of cells expressing the native Cas9 protein alone and may reach a much higher increase of the rate of HR. Such increase in GFP positive cells reflects an increase of at least 10% in HDR driven genome-editing events or much higher, preferably at least 100% higher.

Example 2: Genome Editing by a Cas9-HDRP Fusion Protein Increases the Rate of GFP Gene Correction Greater than Co-Expression of Cas9 and a HDRP as Separate Polypeptides The effect of Cas9, Cas9 co-expressed with Rad51 as separate polypeptides and Rad51-Cas9 fusion protein on HDR efficiency was compared. To this end, an expression vector carrying one of the relevant expression cassettes (i.e., Cas9 with or without HDRP fusion, SEQ ID NO: 05 and SEQ ID NO: 09, and Rad51, SEQ ID NO: 10), were introduced into 293T-iGFP cells along with the donor DNA oligo DD-GFP-C-88ss (SEQ ID NO: 4) and the guide RNA expression vector pGFP-GUID1 (SEQ ID NO: 3). Transfected cells were harvested from individual wells of a 6-well plate at 48 hr post transfection. Cell suspensions of each sample were then transferred to a FACS compatible tube for measurement of GFP florescent intensity.

Flow cytometry was performed on a BD-LSRII (Becton Dickinson) and analysis was done using FlowJo FACS analysis software.

Surprisingly, results demonstrated a greater increase in HDR mediated repair efficiency in cells transfected with the Rad51-Cas9 fusion protein compared to cells transfected with Cas9 alone or cells transfected to co-express both Cas9 and Rad51 as unattached proteins. These results demonstrate the advantages of utilizing a fusion of Rad51 to Cas9 for increasing HDR mediated repair efficiency (FIG. 3A). Moreover, this increase in HDR mediated repair efficiency was achieved even though cells expressed the Rad51-Cas9 fusion protein at lower relative levels when compared to cells transfected with Cas9 alone or cells transfected to co-express Rad51 and Cas9 as unattached proteins (FIG. 3B).

These results indicate that the expression of a Rad51-Cas9 fusion protein in a cell increases HDR efficacy greater than co-expression of Rad51 and Cas9. Notably, Rad51, which is a homologous recombination protein, is not essential to ssDNA repair that is facilitated by an HDR mechanism. See for example, Wang et al., Molecular Therapy—Nucleic Acids (2016) 5, e396; and Bothmer et al., Nature Communications (2017) 8:13905.

Example 3: Genome Editing by a Cas9-HDRP Fusion Protein Increases the Rate of GFP Gene Correction and is Influenced by the Identity of the Linker Sequence The effect of Rad51-Cas9 fusion proteins having different linkers (SEQ ID NO: 9, SEQ ID NO: 11 or SEQ ID NO: 12), on HDR efficacy was evaluated as follows: 300 ng of an expression vector carrying one of the relevant expression cassettes i.e., Cas9 (SEQ ID NO: 05), CAS9-P2A-Rad51 (SEQ ID NO: 13), Rad51-Cas9 fusions including different linkers (SEQ ID NO: 9, SEQ ID NO: 11 or SEQ ID NO: 12), were introduced into 293T-iGFP cells via lipofectamine 3000 transfection along with 20 pmol of the donor DNA oligo DD-GFP-C-88ss and 50 ng of the guide RNA expression vector pGFP-GUID1. Transfected cells were harvested from individual wells of 6-well plate at 72 hr post-transfection. Cell suspensions of each sample were then transferred to a FACS compatible tube for measurement of GFP florescent intensity. Flow cytometry was performed on a BD-LSRII (Becton Dickinson) and analysis was done using FlowJo FACS analysis software.

Figure 4:
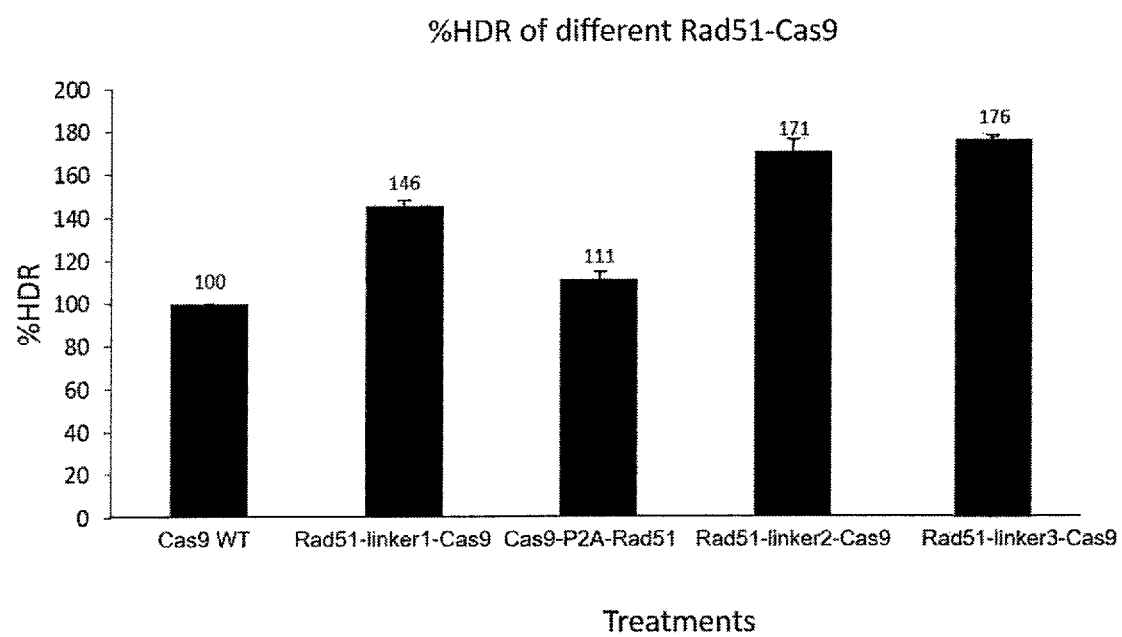
FIG. 4: Comparison of the effect of the linkers in Cas9-HDRP fusion proteins on HDR efficiency.

Results demonstrated an increase in HDR efficacy in cells transfected with Rad51-Cas9 fusion proteins compared to cells transfected with Cas9 wild type or with Cas9-P2A-Rad51 (co-expression of Cas9 and Rad51). These results further demonstrate the advantageousness of utilizing a fusion of an HDRP to a nuclease for increasing HDR efficacy (FIG. 4).

The examples provided above are to facilitate a more complete understanding of the invention. The examples illustrate embodiments of making and practicing the invention. However, the scope of the invention is not limited to specific embodiments disclosed in the examples, which are for purposes of illustration only.

REFERENCES

1. Ahmad et al., (1992) Cancer Res. 52:4817-4820
2. Alvarez et al., (1997)Hum. Gene Ther. 5:597-613
3. Anderson, (1992) Science 256:808-813
4. Argast et al. (1998) J Mol. Biol. 280:345-353
5. Arnould et al. (2006) J. Mol. Biol. 355:443-458
6. Ashworth et al. (2006) Nature 441:656-659
7. Basha et al. (2011) Mol. Ther. 19, 2186-2200
8. Beerli et al. (2002) Nature Biotechnol. 20:135-141
9. Behr et al., (1994) Bioconjugate Chem. 5:382-389
10. Belfort et al. (1997) Nucleic Acids Res. 25:3379-3388
11. Beurdeley et al (2013) Nat Comm: 1-8 DOI: 10.1038/ncomms2782
12. Blaese et al., (1995) Cancer Gene Ther. 2:291-297
13. Blaese et al., (1995) Science 270:475-480

14. Boch et al, (2009) Science 326: 1509-1512
15. Boissel et al., (2013) Nucl Acid Res: 1-13, doi: 10.1093/nar/gkt1224
16. Bonas et al., (1989) Mol Gen Genet. 218: 127-136
17. Bothmer et al., (2017) Nature Communications 8:13905
18. Broderick et al. (2016) Nat Cell Biol.
19. Buchscher et al., (1992) J. Virol. 66:2731-2739
20. Chames et al. (2005) Nucleic Acids Res 33(20):e178
21. Chang et al. (1987) Proc. Natl. Acad. Sci. USA 84:4959-4963
22. Chevalier et al. (2002) Molec. Cell 10:895-905
23. Chilton et al. (2003), Plant Physiology. 133: 956-65
24. Choo et al. (2000) Curr. Opin. Struct. Biol. 10:411-416
25. Chung et al. (2006) Trends Plant Sci. 11(1):1-4
26. Coelho et al. (2013) N. Engl. J. Med. 369, 819-829
27. Crystal, (1995) Science 270:404-410
28. Dillon, (1993) TIBTECH 11:167-175
29. Dranoff et al., (1997)Hum. Gene Ther. 1:111-2
30. Dujon et al. (1989) Gene 82:115-118
31. Dunbar et al., (1995) Blood 85:3048-305
32. Ellem et al., (1997) Immunol Immunother. 44(1):10-20
33. Epinat et al. (2003) Nucleic Acids Res. 31:2952-2962
34. Fields et al. (1989) Nature 340:245-246
35. Freshney et al., (1994) Culture of Animal Cells, A Manual of Basic Technique (3rd ed.)
36. Gao et al., (1995) Gene Therapy 2:710-722
37. Gimble et al. (1996) J. Mol. Biol. 263:163-180
38. Gouble et al. (2006), J. Gene Med. 8(5):616-622
39. Grizot et al (2009) Nucleic Acids Res July 7 e publication
40. Haddada et al., (1995) Current Topics in Microbiology and Immunology Doerfler and Bohm (eds.)
41. Haft et al., (2005) PLoS Comput. Biol. 1: e60
42. Han et al., (1995) Proc. Natl. Acad. Sci. USA 92:9747-9751
43. Hermonat & Muzyczka, (1984) PNAS 81:6466-6470
44. Heuer et al (2007) Applied and Environmental Microbiology 73(13): 4379-4384)
45. Inaba et al., (1992) J. Exp. Med. 176:1693-1702
46. Isalan et al. (2001) Nature Biotechnol. 19:656-660
47. Jansen et al., (2002) Mol. Microbiol. 43: 1565-1575
48. Jasin (1996) Trends Genet. 12:224-228
49. Johann et al., (1992) J. Virol. 66:1635-1640
50. Judge et al. (2006) Mol. Ther. 13, 494-505
51. Kay et al (2007) Science 318:648-651
52. Kearns et al., (1996) Gene Ther. 9:748-55
53. Kohn et al., (1995) Nat. Med. 1:1017-102
54. Kotin, (1994) Human Gene Therapy 5:793-801
55. Kremer & Perricaudet, (1995) British Medical Bulletin 51(1):31-44
56. Linn et al. (eds.) (1993) Nucleases, Cold Spring Harbor Laboratory Press
57. MacDiamid et al (2009) Nature Biotechnology 27(7) p. 643
58. Makarova et al., (2002). Nucleic Acids Res. 30: 482-496
59. Makarova et al., (2006). Biol. Direct 1: 7
60. Malech et al., (1997) PNAS 94:22 12133-12138
61. Miller et al., (1991) J. Virol. 65:2220-2224
62. Miller, (1992) Nature 357:455-460
63. Mitani & Caskey, (1993) TIBTECH 11:162-166
64. Monet et al. (1999), Biochem. Biophysics. Res. Common. 255: 88-93
65. Moscou and Bogdanove, (2009) Science 326: 1501
66. Muzyczka, (1994) J. Clin. Invest. 94:1351
67. Nabel & Feigner, (1993) TIBTECH 11:211-217
68. Nehls et al. (1996) Science 272:886-889
69. New England Biolabs 2002-2003 Catalogue, Beverly, Mass.
70. Pabo et al. (2001) Ann. Rev. Biochem. 70:313-340
71. Paques et al. (2007) Current Gene Therapy 7:49-66
72. Perler et al. (1994) Nucleic Acids Res. 22, 1125-1127
73. Porteus et al. (2005), Nat. Biotechnol. 23: 967-73
74. Puchta et al. (1996) Proc. Natl. Acad. Sci. USA 93: 5055-60
75. Remington's Pharmaceutical Sciences, (1989) 17th ed.
76. Remy et al., (1994) Bioconjugate Chem. 5:647-654
77. Rong et al. (2002) Genes Dev. 16: 1568-81
78. Rosenecker et al., (1996) Infection 24:1 5-10
79. Route et al. (1994) Mol. Cell. Biol. 14: 8096-106
80. Samulski et al. (1989) J. Virol. 63:03822-3828
81. Schornack S, et al (2006) J Plant Physiol 163(3): 256-272
82. Segal et al. (2001) Curr. Opin. Biotechnol. 12:632-637
83. Sommerfelt et al., (1990) Virol. 176:58-59
84. Sterman et al., (1998) Hum. Gene Ther. 9:7 1083-1089
85. Sussman et al. (2004), J. Mol. Biol. 342: 31-41
86. Topf et al., (1998) Gene Ther. 5:507-513
87. Tratschin et al., (1984) Mol. Cell. Biol. 4:2072-2081
88. Tratschin et al., (1985) Mol. Cell. Biol. 5:3251-3260
89. Van Brunt, (1988) Biotechnology 6(10):1149-1154
90. Vigne, (1995) Restorative Neurology and Neuroscience 8:35-36
91. Wagner et al., (1998) Lancet 351:9117 1702-3
92. Wang et al, (2016) Molecular Therapy—Nucleic Acids 5, e396
93. Welsh et al., (1995) Hum. Gene Ther. 2:205-18
94. West et al., (1987) Virology 160:38-47
95. Wilson et al., (1989) J. Virol. 63:2374-2378
96. Yu et al., (1994) Gene Therapy 1:13-26
97. Zetsche et al. (2015) Cell. 163(3):759-71
98. Zuris et al. (2015) Nat. Biotechnol. 33(1):73-80.
99. U.S. Pat. No. 4,186,183
100. U.S. Pat. No. 4,217,344
101. U.S. Pat. No. 4,235,871
102. U.S. Pat. No. 4,261,975
103. U.S. Pat. No. 4,485,054
104. U.S. Pat. No. 4,501,728
105. U.S. Pat. No. 4,774,085
106. U.S. Pat. No. 4,797,368
107. U.S. Pat. No. 4,837,028
108. U.S. Pat. No. 4,897,355
109. U.S. Pat. No. 4,946,787
110. U.S. Pat. No. 5,049,386
111. U.S. Pat. No. 5,173,414
112. U.S. Pat. No. 5,176,996
113. U.S. Pat. No. 5,420,032
114. U.S. Pat. No. 5,422,251
115. U.S. Pat. No. 5,585,245
116. U.S. Pat. No. 5,789,538
117. U.S. Pat. No. 5,925,523
118. U.S. Pat. No. 5,928,638
119. U.S. Pat. No. 6,007,988
120. U.S. Pat. No. 6,013,453
121. U.S. Pat. No. 6,140,081
122. U.S. Pat. No. 6,200,759
123. U.S. Pat. No. 6,453,242
124. U.S. Pat. No. 6,503,717
125. U.S. Pat. No. 6,534,261
126. U.S. Pat. No. 6,599,692
127. U.S. Pat. No. 6,607,882
128. U.S. Pat. No. 6,689,558
129. U.S. Pat. No. 6,794,136

130. U.S. Pat. No. 6,824,978
131. U.S. Pat. No. 6,833,252
132. U.S. Pat. No. 6,933,113
133. U.S. Pat. No. 6,979,539
134. U.S. Pat. No. 7,013,219
135. U.S. Pat. No. 7,030,215
136. U.S. Pat. No. 7,067,317
137. U.S. Pat. No. 7,070,934
138. U.S. Pat. No. 7,163,824
139. U.S. Pat. No. 7,253,273
140. U.S. Pat. No. 7,262,054
141. U.S. Pat. No. 7,361,635
142. U.S. Pat. No. 7,479,554
143. U.S. Pat. No. 7,914,796
144. U.S. Pat. No. 7,951,925
145. U.S. Pat. No. 8,034,598
146. U.S. Pat. No. 8,110,379
147. U.S. Pat. No. 8,420,782
148. U.S. Pat. No. 8,440,431
149. U.S. Pat. No. 8,586,526
150. U.S. Pat. No. 8,623,618
151. U.S. Patent Publication No. 2004/0002092
152. U.S. Patent Publication No. 2005/0064474
153. U.S. Patent Publication No. 2005/0267061
154. U.S. Patent Publication No. 2006/0078552
155. U.S. Patent Publication No. 2006/0153826
156. U.S. Patent Publication No. 2006/0206949
157. U.S. Patent Publication No. 2007/0117128
158. U.S. Patent Publication No. 2007/0218528
159. U.S. Patent Publication No. 2008/0159996
160. U.S. Patent Publication No. 2009/0117617
161. U.S. Patent Publication No. 2010/0218264
162. U.S. Patent Publication No. 2010/0291048
163. U.S. Patent Publication No. 2010/0003756
164. U.S. Patent Publication No. 2010/0047805
165. U.S. Patent Publication No. 2011/0201055
166. U.S. Patent Publication No. 2011/0207221
167. U.S. Patent Publication No. 2011/0265198
168. U.S. Patent Publication No. 2011/0281361
169. U.S. Patent Publication No. 2012/0017290
170. U.S. Patent Publication No. 2013/0122591
171. U.S. Patent Publication No. 2013/0137104
172. U.S. Patent Publication No. 2013/0177960
173. U.S. Patent Publication No. 2013/0177983
174. U.S. Patent Publication No. 2014/0017212
175. U.S. Patent Publication No. 2015/0211023
176. U.S. Provisional Application No. 61/823,689
177. U.S. Provisional Application No. 61/694,693
178. PCT International Publication No. WO/1991/016024
179. PCT International Publication No. WO/1991/017424
180. PCT International Publication No. WO/1993/024641
181. PCT International Publication No. WO/1995/019431
182. PCT International Publication No. WO/1996/06166
183. PCT International Publication No. WO/1998/044350
184. PCT International Publication No. WO/1998/053057
185. PCT International Publication No. WO/1998/053058
186. PCT International Publication No. WO/1998/053059
187. PCT International Publication No. WO/1998/053060
188. PCT International Publication No. WO/1998/054311
189. PCT International Publication No. WO/2000/027878
190. PCT International Publication No. WO/2001/060970
191. PCT International Publication No. WO/2001/088197
192. PCT International Publication No. WO/2002/016536
193. PCT International Publication No. WO/2002/099084
194. PCT International Publication No. WO/2003/016496
195. PCT International Publication No. WO/2010/079430
196. PCT International Application No. PCT/US94/05700

---

What is claimed is:

1. A composition comprising a fusion protein, the fusion protein comprising:
   a) an RNA-guided DNA nuclease, wherein the RNA-guided DNA nuclease is Cas9; and
   b) a homology directed repair (HDR) protein, wherein the HDR protein is Rad51.

2. The composition of claim 1, further comprising a linker, wherein said linker is attached to said RNA-guided DNA nuclease and to said HDR protein.

3. The composition of claim 2, wherein said linker is a polypeptide attached by polypeptide bonds to said RNA-guided DNA nuclease and to said HDR protein.

4. The composition of claim 3, wherein said linker has a length of 1-100 amino acids.

5. The composition of claim 4, wherein said linker has an amino acid sequence selected from the group consisting of SEQ ID NO: 14, SEQ ID NO: 15 and SEQ ID NO: 16.

6. The composition of claim 1, wherein the RNA-guided DNA nuclease is upstream of the HDR protein.

7. The composition of claim 1, wherein the RNA-guided DNA nuclease is downstream of the HDR protein.

8. A method for genome editing comprising introducing to a cell the fusion protein of claim 1 so as to induce genome editing in the cell.

9. The method of claim 8, further comprising introducing to the cell an exogenous donor DNA.

10. The method of claim 8 for increasing the rate of homology directed recombination at a target site in the genome of a cell, wherein the rate of homology directed recombination at the target site in the cell is improved compared to the rate of homology directed recombination at the target site in a cell containing the RNA-guided DNA nuclease alone.

11. The method of claim 8, wherein the cell is a eukaryotic cell.

12. The method of claim 8, further comprising introducing to the cell an additional HDR protein, or a polynucleotide encoding the additional HDR protein.

13. The method of claim 8, wherein the cell undergoing the genome editing is used for forming a transgenic organism.

14. A method of treating a genetic disease in a patient comprising administering to the patient the composition of claim 1.

15. The method of claim 8 for treating a genetic disease in a patient.

16. The composition of claim 1, wherein the Rad51 is encoded by the Rad51 nucleotide sequence of any one SEQ ID NOs: 9-13.

17. The composition of claim 1, wherein the Cas9 is encoded by the Cas9 nucleotide sequence of any one SEQ ID NOs: 5-9 or 11-13.

18. The composition of claim 1, wherein the fusion protein is encoded by any one of SEQ ID Nos: 9 or 11-13.

19. A polynucleotide encoding the fusion protein of claim 1.

20. The method of claim 8, wherein a polynucleotide encoding the fusion protein is introduced to the cell.

* * * * *